US012624039B2

(12) United States Patent
Zhou et al.

(10) Patent No.: US 12,624,039 B2
(45) Date of Patent: May 12, 2026

(54) BTK INHIBITORS

(71) Applicant: DIZAL (JIANGSU) PHARMACEUTICAL CO., LTD., Shanghai (CN)

(72) Inventors: Quan Zhou, Shanghai (CN); Changmao Shen, Shanghai (CN); Xiang Chen, Shanghai (CN); Wengeng Liu, Shanghai (CN); Rumin Wang, Shanghai (CN); Qingbei Zeng, Shanghai (CN); Honchung Tsui, Shanghai (CN); Zhenfan Yang, Shanghai (CN); Xiaolin Zhang, Shanghai (CN)

(73) Assignee: DIZAL (JIANGSU) PHARCEUTICAL CO., LTD., Shanghai (CN)

( * ) Notice: Subject to any disclaimer, the term of this patent is extended or adjusted under 35 U.S.C. 154(b) by 949 days.

(21) Appl. No.: 17/790,721

(22) PCT Filed: Dec. 29, 2020

(86) PCT No.: PCT/CN2020/140517
§ 371 (c)(1),
(2) Date: Jul. 1, 2022

(87) PCT Pub. No.: WO2021/136219
PCT Pub. Date: Jul. 8, 2021

(65) Prior Publication Data

US 2023/0122807 A1 Apr. 20, 2023

(30) Foreign Application Priority Data

Jan. 2, 2020 (WO) ................ PCT/CN2020/070034
Dec. 8, 2020 (WO) ................ PCT/CN2020/134601

(51) Int. Cl.
*C07D 487/04* (2006.01)

(52) U.S. Cl.
CPC ........ *C07D 487/04* (2013.01); *C07B 2200/09* (2013.01)

(58) Field of Classification Search
CPC .......................... C07D 487/04; C07B 2200/09
See application file for complete search history.

(56) References Cited

FOREIGN PATENT DOCUMENTS

| | | | | | |
|---|---|---|---|---|---|
| EP | 3480199 | A1 | | 5/2019 | |
| EP | 3912980 | A1 | | 11/2021 | |
| EP | 4186906 | A1 | | 5/2023 | |
| WO | WO-2009143051 | A1 | * | 11/2009 | ........... C07D 487/04 |
| WO | 2012158795 | A1 | | 11/2012 | |
| WO | 2015074138 | A1 | | 5/2015 | |
| WO | 2016106652 | A1 | | 7/2016 | |
| WO | 2016210165 | A1 | | 12/2016 | |
| WO | 2017025814 | A1 | | 2/2017 | |
| WO | 2018001331 | A1 | | 1/2018 | |
| WO | 2020147798 | A1 | | 7/2020 | |
| WO | 2020150681 | A1 | | 7/2020 | |
| WO | 2022012509 | A1 | | 1/2022 | |

OTHER PUBLICATIONS

Szklener, Katarzyna, et al. "Ibrutinib in the treatment of solid tumors: current state of knowledge and future directions." Cells 11.8 (2022): 1338. (Year: 2022).*
Tasso, Bruno, et al. "The development of BTK inhibitors: a five-year update." Molecules 26.23 (2021): 7411. (Year: 2021).*
Alu, Aqu, et al. "BTK inhibitors in the treatment of hematological malignancies and inflammatory diseases: mechanisms and clinical studies." Journal of Hematology & Oncology 15.1 (2022): 138. (Year: 2022).*
GarcÃ-a-Merino, Antonio. "Brutonâs tyrosine kinase inhibitors: a new generation of promising agents for multiple sclerosis therapy." Cells 10.10 (2021): 2560. (Year: 2021).*

(Continued)

*Primary Examiner* — James H Alstrum-Acevedo
*Assistant Examiner* — Justin Christopher Sanchez
(74) *Attorney, Agent, or Firm* — Junhe Law Office P.C.; Zhaohui Wang

(57) ABSTRACT

The invention relates to chemical compounds, or pharmaceutically acceptable salts thereof, of the formula (I) which possess BTK inhibitory activity and are accordingly useful in therapy and in methods of treatment of the human or animal body. The invention also relates to processes for the manufacture of said chemical compounds, to pharmaceutical compositions containing them, and to their use in the manufacture of medicaments for use in a therapeutic effect in a warm-blooded animal such as man.

(I)

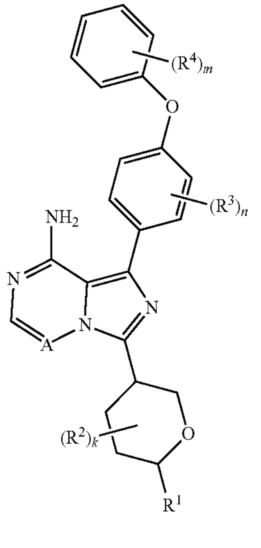

34 Claims, No Drawings

(56) References Cited

OTHER PUBLICATIONS

Ringheim, Garth E., Matthew Wampole, and Kinsi Oberoi. "Brutonas tyrosine kinase (BTK) inhibitors and autoimmune diseases: making sense of BTK inhibitor specificity profiles and recent clinical trial successes and failures." Frontiers in immunology 12 (2021): 662223. (Year: 2021).*

The extended European Search Report for EP application 20910897.6 mailed on Jan. 4, 2024.

The international search report of PCT application No. PCT/CN2020/140517, issued on Mar. 25, 2021.

* cited by examiner

BTK INHIBITORS

CROSS-REFERENCE TO RELATED APPLICATIONS

This application is a national phase application, filed pursuant to 35 U.S.C § 371 of PCT Application No. PCT/CN2020/140517 filed on Dec. 29, 2020, which claims foreign priorities of PCT Application No. PCT/CN2020/070034 filed on Jan. 2, 2020 and PCT Application No. PCT/CN2020/134601 filed on Dec. 8, 2020, both are now abandoned. Each of these applications is hereby incorporated by reference herein in its entirety.

FIELD

The present application is directed towards oxane substituted imidazopyrazine and imidazotriazine inhibitors of Bruton's Tyrosine Kinase (BTK), including mutant BTK, useful in the treatment of diseases or disorders associated with BTK kinase. These compounds have potential utility in the treatment of immune disorders, cancer, cardiovascular diseases, viral infections, inflammation, metabolism/endocrine function disorders, and neurological disorders.

Specifically, the application is directed towards compounds and compositions thereof which inhibit BTK, methods of treating diseases or disorders associated with BTK, and methods of synthesis of these compounds.

BACKGROUND

Bruton's Tyrosine Kinase (BTK), also known as tyrosine-protein kinase BTK, is a member of the Tec family of tyrosine kinases and plays an important role in the regulation of early B-cell development and mature B-cell activation and survival (Hunter, Cell, 87, 50, 823-829). The BTK enzyme is encoded by the BTK gene, and has been shown to initiate a number of cellular processes including cell proliferation, survival, differentiation, motility, angiogenesis, cytokine production, and antigen presentation.

BTK-deficient mouse models have shown that BTK plays a role in allergic disorders and/or autoimmune disease and/or inflammatory disease; and BTK inhibition has potential utility in the treatment of such diseases as systemic lupus erythematosus (SLE), Urticaria/Sjogren's syndrome, rheumatoid arthritis, vasculitis, idiopathic thrombocytopenic purpura (ITP), myasthenia gravis, allergic rhinitis, and asthma.

BTK's role in apoptosis also demonstrates the utility of inhibition of BTK activity for the treatment of cancers, for example B-cell lymphoma, leukaemia, and other haematological malignancies. In addition, BTK has a role in osteoclast function, so inhibition of BTK activity has potential utility in the treatment of bone disorders, such as osteoporosis.

Approved compounds that inhibit BTK include ibrutinib (B cell malignancies e.g. mantle cell lymphoma, chronic lymphocytic leukaemia (CLL), Waldenström's macroglobulinemia); acalabrutinib (mantle cell lymphoma and CLL); and zanubrutinib (mantle cell lymphoma). In addition there are several BTK inhibitors in clinical trials including evobrutinib (multiple sclerosis); ABBV-105 (systemic lupus erythematosus (SLE)); ONO-4059/GS-4059 (non-Hodgkin lymphoma and CLL); spebrutinib (relapsed or refractory B Cell Non-Hodgkin Lymphoma, CLL and Waldenström's Macroglobulinemia); and HM71224 (autoimmune diseases).

Despite major therapeutic advances in the treatment of B-cell malignancies using BTK inhibitors, cases of primary and secondary resistance have emerged with poor outcomes and limited treatment options.

Covalent (irreversible) BTK inhibitors such as ibrutinib and acalabrutinib bind with the C481 site of BTK rendering it kinase-inactive. This binding is permanent until the BTK protein degrades. The advantages of these irreversible inhibitors are that they are potent and usually only a short period of exposure will be efficacious. However, their clinical benefit is limited by off-target toxicity, leading to high rates of discontinuation, and acquired resistance due to BTK C481 mutations that disrupt covalent binding to BTK, reducing the compounds' binding affinity, and diminishing their ability to inhibit BTK enzymatic activity (Leukaemia 2015, April; 29(4):895-900). The majority (>50%) of CLL patients who progress on covalent BTK inhibitor therapy become resistant to treatment due to the development of a C481S mutation (N. Engl. J. Med. 370; 24, 2014; JAMA Oncol. 2015; 1(1):80-87; and J. Clin. Oncol. 35:1437-1443, 2017).

Primary central nervous system lymphoma (PCNSL) is a disease in which malignant (cancer) cells is form in the lymph tissue of the brain and/or spinal cord, and it accounts for approximately 1% of all lymphomas and 2% to 5% of all primary brain tumours. The vast majority (approximately 95%) of PCNSLs are diffuse large B-cell lymphomas (DLBCL). Mutation in the CD79B and MYD88 genes are frequently (~30-80%) coincident with PCNSL (Neuropathol. Appl. Neurobiol. 2016 April; 42(3):279-90). Although to date BTK inhibitors have not been approved for the treatment of DLBCL, data suggests that DLBCL with CD79B and MYD88 mutations are more sensitive to BTK inhibition (Nat. Med. 2015 August; 21(8):922-6).

Secondary CNS lymphoma (SCNSL) refers to central nervous system spread of a lymphoma that originated elsewhere (in contrast to primary CNS lymphoma). It is typically a non-Hodgkin lymphoma, and may be an isolated recurrence or may be part of a systemic disease at the time of presentation. Unlike primary CNS lymphoma, it more commonly involves the leptomeninges.

PRN2246 (SAR442168), a blood brain barrier (BBB) penetrable covalent BTK inhibitor, was well tolerated in phase I trial for multiple sclerosis (MS). In addition, some trials (Grommes C, et al., Cancer Discov. 2017 September; 7(9):1018-1029; Grommes C, et al., Blood. 2019433(5):436-445; Lionakis et al., 2017, Cancer Cell 31, 833-843 and Soussain C et al., Eur J Cancer. 2019 August; 117:121-130) have suggested that a high dose of ibrutinib (840 mg) would have efficacy in CNS lymphomas (both PCNSL and secondary nervous system lymphoma (SCNSL)), but to date, no BTK inhibitors have been approved that target a BTK-C481 mutation, or have activity in PCNSL. These both remain unmet medical needs.

WO 2009/143051 discloses certain substituted imidazopyrazines and imidazotriazines, including certain hexane substituted imidazopyrazines and imidazotriazines, as activated p21cdc42Hs-associated kinase (ACK1) inhibitors. However, the compounds of WO 2009/143051 exhibit high human hepatocyte clearance meaning the compounds potentially cannot reach enough sustained drug coverage even at the maximal absorbable dose (making the compounds ineffective); and/or very high doses are needed to inhibit the target, leading to a high maximal drug concentration (potentially leading to secondary pharmacological (i.e. adverse) effects and to toxicity issues).

WO2017111787A1 discloses a tetrahydropyranyl amino-pyrrolopyrimidinone that modulates the activity of BTK; WO2018039310A1 amino-pyrrolopyrimidinone compounds and methods of use thereof; WO2017103611A1 discloses compounds useful as inhibitors of BTK; and WO2011152351 discloses purinone derivatives having BTK-selective inhibitory activity. However, none of these compounds possess the combination of desired properties that the compounds of the present invention possess.

Disclosed herein are certain novel oxane substituted imidazopyrazines and imidazotriazines that are potent, selective inhibitors of BTK, both wild-type BTK, and BTK with a C481 mutation (for example a C481S, C481Y, C481R or C481F mutation). These compounds are non-covalent reversible inhibitors, exhibit low human hepatocyte clearance and have blood brain barrier (BBB) penetrating properties.

SUMMARY

Disclosed herein are compounds of formula (I):

(I)

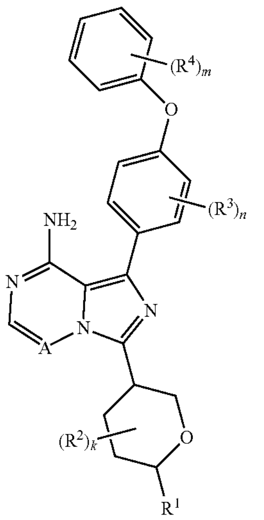

and pharmaceutically acceptable salt thereof, and their use as BTK inhibitors, particularly in therapy.

DETAILED DESCRIPTION OF THE INVENTION

Many embodiments of the invention are detailed throughout the specification and will be apparent to a reader skilled in the art. The invention is not to be interpreted as being limited to any of the recited embodiments, and claims are embodiments. It is appreciated that certain features of the present disclosure, which are, for clarity, described in the context of separate embodiments, can also be provided in combination in a single embodiment. Conversely, various features of the present disclosure, which are, for brevity, described in the context of a single embodiment, can also be provided separately or in any suitable sub combination.

Disclosed herein is a compound of formula (I):

(I)

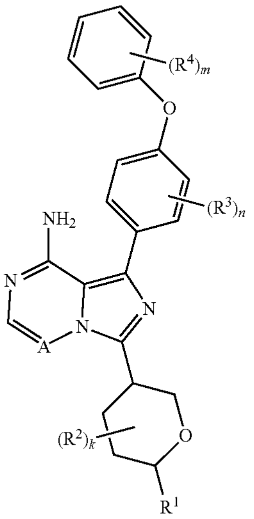

wherein:

$R^2$ is selected from hydrogen, $C_{1-6}$alkyl, $C_{1-6}$alkoxy, N—$C_{1-6}$alkylamino, N,N—$(C_{1-6}alkyl)_2$amino, carbocyclyl and heterocyclyl; wherein $R^1$ may be optionally substituted by one or more $R^5$;

$R^2$ is selected from halo, $C_{1-3}$alkyl, $C_{1-3}$alkoxy, carbocyclyl and heterocyclyl; or two $R^2$, either on the same atom or on adjoining atoms, may together with the atoms to which they are attached form a 3-7 membered ring;

k is 0-4;

$R^3$ is selected from halo, $C_{1-3}$alkyl and $C_{1-3}$alkoxy;

n is 0-4;

$R^4$ is selected from halo, $C_{1-3}$alkyl and $C_{1-3}$alkoxy;

m is 0-5;

A is =N— or =C($R^6$)—;

$R^5$ is selected from halo, hydroxy, $C_{1-6}$alkoxy, amino, N—$C_{1-6}$alkylamino, N,N—$(C_{1-6}alkyl)_2$amino, carbocyclyl and heterocyclyl; wherein $R^5$ may be independently optionally substituted by one or more $R^7$;

$R^6$ is selected from hydrogen and halo;

$R^2$ is selected from halo, hydroxy, amino, $C_{1-3}$alkyl and $C_{1-3}$alkoxy;

or a pharmaceutically acceptable salt thereof.

In one embodiment $R^1$ is selected from hydrogen and $C_{1-6}$alkyl; wherein $R^1$ may be optionally substituted by one $R^5$; wherein $R^5$ is selected from hydroxy, $C_{1-6}$alkoxy, N,N—$(C_{1-6}alkyl)_2$amino and heterocyclyl.

In one embodiment $R^1$ is selected from hydrogen and $C_{1-3}$alkyl; wherein $R^1$ may be optionally substituted by one $R^5$; wherein $R^5$ is selected from hydroxy, $C_{1-3}$alkoxy, N,N—$(C_{1-2}alkyl)_2$amino and azetidinyl.

In one embodiment $R^1$ is selected from hydrogen, methyl, hydroxymethyl, methoxymethyl, N,N-dimethylaminomethyl and azetidin-1-ylmethyl.

In one embodiment $R^1$ is hydroxymethyl.

In one embodiment $R^2$ is selected from halo or $C_{1-3}$alkoxy.

In one embodiment $R^2$ is selected from fluoro or methoxy.

In one embodiment or two $R^2$, either on the same atom or on adjoining atoms, may together with the atoms to which they are attached form a 3-7 membered ring.

In one embodiment or two $R^2$ on the same atom may together with the atom to which they are attached form a 3-7 membered ring.

In one embodiment or two $R^2$ on adjoining atoms may together with the atoms to which they are attached form a 3-7 membered ring.

In one embodiment k is 0.

In one embodiment k is 1.

In one embodiment k is 2.

In one embodiment k is 3.

In one embodiment k is 4.

In one embodiment $R^3$ is halo.

In one embodiment $R^3$ is fluoro.

In one embodiment n is 0-2.

In one embodiment n is 0.

In one embodiment n is 1.

In one embodiment n is 2.

In one embodiment n is 3.

In one embodiment n is 4.

In one embodiment $R^4$ is halo.

In one embodiment $R^4$ is fluoro.

In one embodiment m is 0-2.

In one embodiment m is 0.

In one embodiment m is 1.

In one embodiment m is 2.

In one embodiment m is 3.

In one embodiment m is 4.

In one embodiment m is 5.

In one embodiment A is ═N— or ═C(H)—.

In one embodiment A is ═N—.

In one embodiment A is ═C($R^6$)—.

In one embodiment A is ═C(H)—.

The compound of formula (I) (when R1≠hydrogen) contains two chiral centres (marked with an "*"):

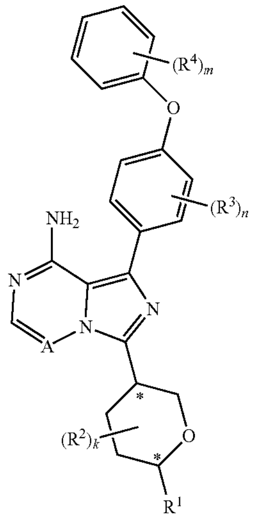

These chiral centres can exist in the "trans" configuration (meaning the two substituents on the oxane ring point to the opposite face of the oxane ring); and the "cis" configuration (meaning the two substituents on the oxane ring point to the same face of the oxane ring). Structures (IA) and (IB) hereinbelow show the cis isomers of compounds of formula (I), Structures (IC) and (ID) hereinbelow show the trans isomers of compounds of formula (I).

In one aspect of the invention, a compound of formula (I) is a trans compound of formula (I).

In one aspect of the invention, a compound of formula (I) is a cis compound of formula (I).

In one aspect of the invention, a compound of formula (I) is a compound of formula (IA):

(IA)

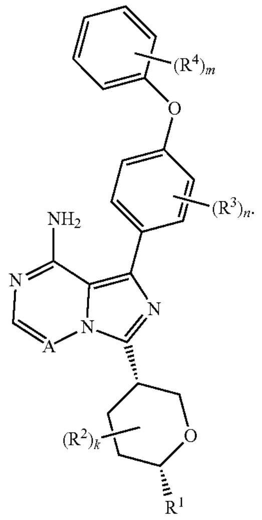

In one aspect of the invention, a compound of formula (I) is a compound of formula (IB):

(IB)

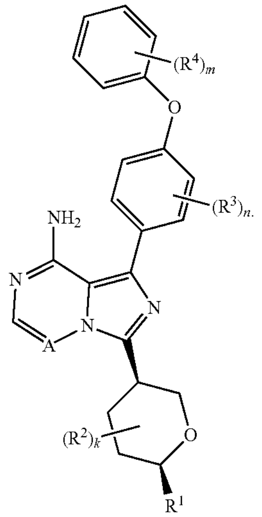

In one aspect of the invention, a compound of formula (I) is a compound of formula (IC):

(IC)

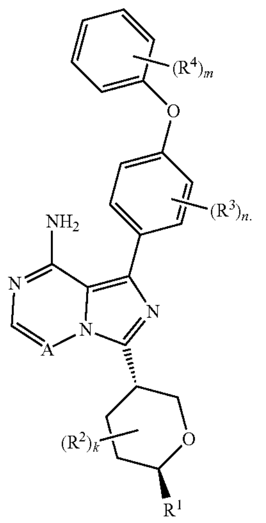

In one aspect of the invention, a compound of formula (I) is a compound of formula (ID):

(ID)

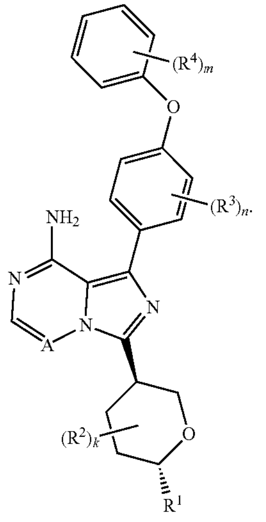

In one aspect of the invention, a compound of formula (I) is selected from (5-(8-amino-1-(4-phenoxyphenyl)imidazo[1,5-a]pyrazin-3-yl)tetrahydro-2H-pyran-2-yl)methanol;

(5-(8-amino-1-(2-fluoro-4-phenoxyphenyl)imidazo[1,5-a]pyrazin-3-yl)tetrahydro-2H-pyran-2-yl)methanol;

(5-(8-amino-1-(2,3-difluoro-4-phenoxyphenyl)imidazo[1,5-a]pyrazin-3-yl)tetra hydro-2H-pyran yl)methanol;

(5-(8-amino-1-(4-(2,3-difluorophenoxy)phenyl)imidazo[1,5-a]pyrazin-3-yl)tetrahydro-2H-pyran (5-(4-amino-5-(2-fluoro-4-phenoxyphenyl)imidazo[5,1-f][1,2,4]triazin-7-yl)tetrahydro-2H-pyran yl)methanol;

(5-(4-amino-5-(2-fluoro-4-phenoxyphenyl)imidazo[5,1-f][1,2,4]triazin-7-yl)tetrahydro-2H-pyran yl)methanol;

(5-(4-amino-5-(2,3-difluoro-4-phenoxyphenyl)imidazo[5,1-f][1,2,4]triazin-7-yl)tetrahydro-2H-pyran-2-yl)methanol;

(5-(4-amino-5-(4-(2,3-difluorophenoxy)phenyl)imidazo[5,1-f][1,2,4]triazin-7-yl)tetrahydro-2H-pyran-2-yl)methanol;

3-(6-((dimethylamino)methyl)tetrahydro-2H-pyran-3-yl)-1-(2-fluoro-4-phenoxyphenyl)imidazo[1,5-a]pyrazin-8-amine;

7-(6-((dimethylamino)methyl)tetrahydro-2H-pyran-3-yl)-5-(2-fluoro-4-phenoxyphenyl)imidazo[5,1-f][1,2,4]triazin-4-amine;

7-(6-(azetidin-1-ylmethyl)tetrahydro-2H-pyran-3-yl)-5-(2-fluoro-4-phenoxyphenyl)imidazo[5,1-f][1,2,4]triazin-4-amine;

5-(2-fluoro-4-phenoxyphenyl)-7-(6-(methoxymethyl)tetrahydro-2H-pyran-3-yl)imidazo[5,1-f][1,2,4]triazin-4-amine;

5-(2-fluoro-4-phenoxyphenyl)-7-(tetrahydro-2H-pyran-3-yl)imidazo[5,1-f][1,2,4]triazin-4-amine; and 5-(2-fluoro-4-phenoxyphenyl)-7-(6-methyltetrahydro-2H-pyran-3-yl)imidazo[5,1-f][1,2,4]triazin-4-amine.

In one aspect of the invention, a compound of formula (I) is selected from (5-(8-amino-1-(4-phenoxyphenyl)imidazo[1,5-a]pyrazin-3-yl)tetrahydro-2H-pyran-2-yl)methanol;

(5-(8-amino-1-(2-fluoro-4-phenoxyphenyl)imidazo[1,5-a]pyrazin-3-yl)tetrahydro-2H-pyran-2-yl)methanol;

(5-(8-amino-1-(2,3-difluoro-4-phenoxyphenyl)imidazo[1,5-a]pyrazin-3-yl)tetrahydro-2H-pyran-2-yl)methanol;

(5-(8-amino-1-(4-(2,3-difluorophenoxy)phenyl)imidazo[1,5-a]pyrazin-3-yl)tetrahydro-2H-pyran-2-yl)methanol;

(5-(4-amino-5-(2-fluoro-4-phenoxyphenyl)imidazo[5,1-f][1,2,4]triazin-7-yl)tetrahydro-2H-pyran-2-yl)methanol;

(5-(4-amino-5-(2-fluoro-4-phenoxyphenyl)imidazo[5,1-f][1,2,4]triazin-7-yl)tetrahydro-2H-pyran-2-yl)methanol;

(5-(4-amino-5-(2,3-difluoro-4-phenoxyphenyl)imidazo[5,1-f][1,2,4]triazin-7-yl)tetrahydro-2H-pyran-2-yl)methanol;

(5-(4-amino-5-(4-(2,3-difluorophenoxy)phenyl)imidazo[5,1-f][1,2,4]triazin-7-yl)tetrahydro-2H-pyran yl)methanol;

3-(6-((dimethylamino)methyl)tetrahydro-2H-pyran-3-yl)-1-(2-fluoro-4-phenoxyphenyl)imidazo[1,5-a]pyrazin-8-amine;

7-(6-((dimethylamino)methyl)tetrahydro-2H-pyran-3-yl)-5-(2-fluoro-4-phenoxyphenyl)imidazo[5,1-f][1,2,4]triazin-4-amine;

7-(6-(azetidin-1-ylmethyl)tetrahydro-2H-pyran-3-yl)-5-(2-fluoro-4-phenoxyphenyl)imidazo[5,1-f][1,2,4]triazin-4-amine;

5-(2-fluoro-4-phenoxyphenyl)-7-(6-(methoxymethyl)tetrahydro-2H-pyran-3-yl)imidazo[5,1-f][1,2,4]triazin-4-amine;

5-(2-fluoro-4-phenoxyphenyl)-7-(tetrahydro-2H-pyran-3-yl)imidazo[5,1-f][1,2,4]triazin-4-amine; and 5-(2-fluoro-4-phenoxyphenyl)-7-(6-methyltetrahydro-2H-pyran-3-yl)imidazo[5,1-f][1,2,4]triazin-4-amine;

or a pharmaceutically acceptable salt thereof.

In one aspect of the invention, a compound of formula (I) is selected from ((2R,5R)-5-(8-amino-1-(4-phenoxyphenyl)imidazo[1,5-a]pyrazin-3-yl)tetrahydro-2H-pyran-2-yl)methanol;

((2R,5R)-5-(8-amino-1-(2-fluoro-4-phenoxyphenyl)imidazo[1,5-a]pyrazin-3-yl)tetrahydro-2H-pyran-2-yl)methanol;

((2R,5R)-5-(8-amino-1-(2,3-difluoro-4-phenoxyphenyl)imidazo[1,5-a]pyrazin-3-yl)tetrahydro-2H-pyran-2-yl)methanol;

((2R,5R)-5-(8-amino-1-(4-(2,3-difluorophenoxy)phenyl)imidazo[1,5-a]pyrazin-3-yl)tetrahydro-2H-pyran-2-yl)methanol;

((2R,5R)-5-(4-amino-5-(2-fluoro-4-phenoxyphenyl)imidazo[5,1-f][1,2,4]triazin-7-yl)tetrahydro-2H-pyran-2-yl)methanol;

((2R,5R)-5-(4-amino-5-(2-fluoro-4-phenoxyphenyl)imidazo[5,1-f][1,2,4]triazin-7-yl)tetrahydro-2H-pyran-2-yl)methanol;

((2R,5R)-5-(4-amino-5-(2,3-difluoro-4-phenoxyphenyl)imidazo[5,1-f][1,2,4]triazin-7-yl)tetrahydro-2H-pyran-2-yl)methanol;

((2R,5R)-5-(4-amino-5-(4-(2,3-difluorophenoxy)phenyl)imidazo[5,1-f][1,2,4]triazin-7-yl)tetrahydro-2H-pyran-2-yl)methanol;

3-((3R,6R)-6-((dimethylamino)methyl)tetrahydro-2H-pyran-3-yl)-1-(2-fluoro-4-phenoxyphenyl)imidazo[1,5-a]pyrazin-8-amine;

7-((3R,6R)-6-((dimethylamino)methyl)tetrahydro-2H-pyran-3-yl)-5-(2-fluoro-4-phenoxyphenyl)imidazo[5,1-f][1,2,4]triazin-4-amine;

7-((3R,6R)-6-(azetidin-1-ylmethyl)tetrahydro-2H-pyran-3-yl)-5-(2-fluoro-4-phenoxyphenyl)imidazo[5,1-f][1,2,4]triazin-4-amine;

5-(2-fluoro-4-phenoxyphenyl)-7-((3R,6R)-6-(methoxymethyl)tetrahydro-2H-pyran-3-yl)imidazo[5,1-f][1,2,4]triazin-4-amine;

(R)-5-(2-fluoro-4-phenoxyphenyl)-7-(tetrahydro-2H-pyran-3-yl)imidazo[5,1-f][1,2,4]triazin-4-amine; and 5-(2-fluoro-4-phenoxyphenyl)-7-((3R,6R)-6-methyltetrahydro-2H-pyran-3-yl)imidazo[5,1-f][1,2,4]triazin-4-amine;

or a pharmaceutically acceptable salt thereof.

In one aspect of the invention, a compound of formula (I) is selected from ((2S,5S)-5-(8-amino-1-(4-phenoxyphenyl)imidazo[1,5-a]pyrazin-3-yl)tetrahydro-2H-pyran-2-yl)methanol;

((2S,5S)-5-(8-amino-1-(2-fluoro-4-phenoxyphenyl)imidazo[1,5-a]pyrazin-3-yl)tetrahydro-2H-pyran yl)methanol;

((2S,5S)-5-(8-amino-1-(2,3-difluoro-4-phenoxyphenyl)imidazo[1,5-a]pyrazin-3-yl)tetrahydro-2H-pyran-2-yl)methanol;

((2S,5S)-5-(8-amino-1-(4-(2,3-difluorophenoxy)phenyl)imidazo[1,5-a]pyrazin-3-yl)tetrahydro-2H-pyran-2-yl)methanol;

((2S,5S)-5-(4-amino-5-(2-fluoro-4-phenoxyphenyl)imidazo[5,1-f][1,2,4]triazin-7-yl)tetrahydro-2H-pyran-2-yl)methanol;

((2S,5S)-5-(4-amino-5-(2-fluoro-4-phenoxyphenyl)imidazo[5,1-f][1,2,4]triazin-7-yl)tetrahydro-2H-pyran-2-yl)methanol;

((2S,5S)-5-(4-amino-5-(2,3-difluoro-4-phenoxyphenyl)imidazo[5,1-f][1,2,4]triazin-7-yl)tetrahydro-2H-pyran-2-yl)methanol;

((2S,5S)-5-(4-amino-5-(4-(2,3-difluorophenoxy)phenyl)imidazo[5,1-f][1,2,4]triazin-7-yl)tetrahydro-2H-pyran-2-yl)methanol;

3-((3S,6S)-6-((dimethylamino)methyl)tetrahydro-2H-pyran-3-yl)-1-(2-fluoro-4-phenoxyphenyl)imidazo[1,5-a]pyrazin-8-amine;

7-((3S,6S)-6-((dimethylamino)methyl)tetrahydro-2H-pyran-3-yl)-5-(2-fluoro-4-phenoxyphenyl)imidazo[5,1-f][1,2,4]triazin-4-amine;

7-((3S,6S)-6-(azetidin-1-ylmethyl)tetrahydro-2H-pyran-3-yl)-5-(2-fluoro-4-phenoxyphenyl)imidazo[5,1-f][1,2,4]triazin-4-amine;

5-(2-fluoro-4-phenoxyphenyl)-7-((3S,6S)-6-(methoxymethyl)tetrahydro-2H-pyran-3-yl)imidazo[5,1-f][1,2,4]triazin-4-amine;

(S)-5-(2-fluoro-4-phenoxyphenyl)-7-(tetrahydro-2H-pyran-3-yl)imidazo[5,1-f][1,2,4]triazin-4-amine; and 5-(2-fluoro-4-phenoxyphenyl)-7-((3S,6S)-6-methyltetrahydro-2H-pyran-3-yl)imidazo[5,1-f][1,2,4]triazin-4-amine;

or a pharmaceutically acceptable salt thereof.

In one aspect of the invention, a compound of formula (I) is selected from ((2S,5R)-5-(8-amino-1-(4-phenoxyphenyl)imidazo[1,5-a]pyrazin-3-yl)tetrahydro-2H-pyran-2-yl)methanol;

((2S,5R)-5-(8-amino-1-(2-fluoro-4-phenoxyphenyl)imidazo[1,5-a]pyrazin-3-yl)tetrahydro-2H-pyran yl)methanol;

((2S,5R)-5-(8-amino-1-(2,3-difluoro-4-phenoxyphenyl)imidazo[1,5-a]pyrazin-3-yl)tetrahydro-2H-pyran yl)methanol;

((2S,5R)-5-(8-amino-1-(4-(2,3-difluorophenoxy)phenyl)imidazo[1,5-a]pyrazin-3-yl)tetrahydro-2H-pyran-2-yl)methanol;

((2S,5R)-5-(4-amino-5-(2-fluoro-4-phenoxyphenyl)imidazo[5,1-f][1,2,4]triazin-7-yl)tetrahydro-2H-pyran-2-yl)methanol;

((2S,5R)-5-(4-amino-5-(2-fluoro-4-phenoxyphenyl)imidazo[5,1-f][1,2,4]triazin-7-yl)tetrahydro-2H-pyran-2-yl)methanol;

((2S,5R)-5-(4-amino-5-(2,3-difluoro-4-phenoxyphenyl)imidazo[5,1-f][1,2,4]triazin-7-yl)tetrahydro-2H-pyran-2-yl)methanol;

((2S,5R)-5-(4-amino-5-(4-(2,3-difluorophenoxy)phenyl)imidazo[5,1-f][1,2,4]triazin-7-yl)tetrahydro-2H-pyran-2-yl)methanol;

3-((3S,6R)-6-((dimethylamino)methyl)tetrahydro-2H-pyran-3-yl)-1-(2-fluoro-4-phenoxyphenyl)imidazo[1,5-a]pyrazin-8-amine;

7-((3S,6R)-6-((dimethylamino)methyl)tetrahydro-2H-pyran-3-yl)-5-(2-fluoro-4-phenoxyphenyl)imidazo[5,1-f][1,2,4]triazin-4-amine;

7-((3S,6R)-6-(azetidin-1-ylmethyl)tetrahydro-2H-pyran-3-yl)-5-(2-fluoro-4-phenoxyphenyl)imidazo[5,1-f][1,2,4]triazin-4-amine;

5-(2-fluoro-4-phenoxyphenyl)-7-((3S,6R)-6-(methoxymethyl)tetrahydro-2H-pyran-3-yl)imidazo[5,1-f][1,2,4]triazin-4-amine; AND 5-(2-fluoro-4-phenoxyphenyl)-7-((3S,6R)-6-methyltetrahydro-2H-pyran-3-yl)imidazo[5,1-f][1,2,4]triazin-4-amine;

or a pharmaceutically acceptable salt thereof.

In one aspect of the invention, a compound of formula (I) is selected from ((2R,5S)-5-(8-amino-1-(4-phenoxyphenyl)imidazo[1,5-a]pyrazin-3-yl)tetrahydro-2H-pyran-2-yl)methanol;

((2R,5S)-5-(8-amino-1-(2-fluoro-4-phenoxyphenyl)imidazo[1,5-a]pyrazin-3-yl)tetrahydro-2H-pyran-2-yl)methanol;

((2R,5S)-5-(8-amino-1-(2,3-difluoro-4-phenoxyphenyl)imidazo[1,5-a]pyrazin-3-yl)tetrahydro-2H-pyran-2-yl)methanol;

((2R,5S)-5-(8-amino-1-(4-(2,3-difluorophenoxy)phenyl)imidazo[1,5-a]pyrazin-3-yl)tetrahydro-2H-pyran-2-yl)methanol;

((2R,5S)-5-(4-amino-5-(2-fluoro-4-phenoxyphenyl)imidazo[5,1-f][1,2,4]triazin-7-yl)tetrahydro-2H-pyran-2-yl)methanol;

((2R,5S)-5-(4-amino-5-(2-fluoro-4-phenoxyphenyl)imidazo[5,1-f][1,2,4]triazin-7-yl)tetrahydro-2H-pyran-2-yl)methanol;

((2R,5S)-5-(4-amino-5-(2,3-difluoro-4-phenoxyphenyl)imidazo[5,1-f][1,2,4]triazin-7-yl)tetrahydro-2H-pyran-2-yl)methanol;

((2R,5S)-5-(4-amino-5-(4-(2,3-difluorophenoxy)phenyl)imidazo[5,1-f][1,2,4]triazin-7-yl)tetrahydro-2H-pyran-2-yl)methanol;

3-((3R,6S)-6-((dimethylamino)methyl)tetrahydro-2H-pyran-3-yl)-1-(2-fluoro phenoxyphenyl)imidazo[1,5-a]pyrazin-8-amine;

7-((3R,6S)-6-((dimethylamino)methyl)tetrahydro-2H-pyran-3-yl)-5-(2-fluoro-4-phenoxyphenyl)imidazo[5,1-f][1,2,4]triazin-4-amine;

7-((3R,6S)-6-(azetidin-1-ylmethyl)tetrahydro-2H-pyran-3-yl)-5-(2-fluoro-4-phenoxyphenyl)imidazo[5,1-f][1,2,4]triazin-4-amine;

5-(2-fluoro-4-phenoxyphenyl)-7-((3R,6S)-6-methyltetrahydro-2H-pyran-3-yl)imidazo[5,1-f][1,2,4]triazin-4-amine;

or a pharmaceutically acceptable salt thereof.

In one aspect of the invention, there is provided any compound of formula (I) disclosed herein.

In one aspect of the invention, there is provided any compound of formula (I) disclosed herein, or a pharmaceutically acceptable salt thereof.

In one aspect of the invention, there is provided a synthetic intermediate used to prepare a compound of formula (I) as disclosed herein.

In one aspect of the invention, there is provided a synthetic intermediate used to prepare a compound of formula (I) as disclosed herein, or a pharmaceutically acceptable salt thereof.

At various places in the present disclosure, linking substituents are described. Where the structure clearly requires a linking group, the Markush variables listed for that group are understood to be linking groups. For example, if the structure requires a linking group and the Markush group definition for that variable lists "alkyl", then it is understood that the "alkyl" represents a linking alkylene group.

As used herein, the term "substituted", when refers to a chemical group, means the chemical group has one or more hydrogen atoms that is/are removed and replaced by substituents. As used herein, the term "substituent" has the ordinary meaning known in the art and refers to a chemical moiety that is covalently attached to, or if appropriate, fused to, a parent group. As used herein, the term "optionally substituted" or "optionally . . . substituted" means that the chemical group may have no substituents (i.e. unsubstituted) or may have one or more substituents (i.e. substituted). It is to be understood that substitution at a given atom is limited by valency.

As used herein, the term "$C_{i-j}$" indicates a range of the carbon atoms numbers, wherein i and j are integers and the range of the carbon atoms numbers includes the endpoints (i.e. i and j) and each integer point in between, and wherein j is greater than i. For examples, $C_{1-6}$ indicates a range of one to six carbon atoms, including one carbon atom, two carbon atoms, three carbon atoms, four carbon atoms, five carbon atoms and six carbon atoms. In some embodiments, the term "$C_{1-6}$" indicates 1 to 6, particularly 1 to 5, particularly 1 to 4, particularly 1 to 3 or particularly 1 to 2 carbon atoms.

As used herein, the term "alkyl", whether as part of another term or used independently, refers to a saturated hydrocarbon chain. The hydrocarbon chain mentioned above may be straight-chain or branched-chain. The term "$C_{i-j}$alkyl" refers to an alkyl having i to j carbon atoms. Examples of $C_{1-6}$alkyl include, but are not limited to, methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. Examples of "$C_{1-3}$alkyl" are methyl, ethyl, propyl and isopropyl.

As used herein the terms "halo" and "halogen" refer to an atom selected from fluorine, chlorine, bromine and iodine.

As used herein, the term "alkoxy", whether as part of another term or used independently, refers to a group of formula —O-alkyl. The term "$C_{i-j}$alkoxy" means that the alkyl moiety of the alkoxy group has i to j carbon atoms. Examples of alkoxy groups include, but are not limited to, methoxy, ethoxy, propoxy (e.g. n-propoxy and isopropoxy), t-butoxy, and the like. Examples of "$C_{1-6}$alkoxyl" are methoxy, ethoxy and propoxy. Examples of "$C_{1-3}$alkoxyl" are methoxy, ethoxy and propoxy.

Examples of "N—($C_{1-6}$alkyl)amino" are methylamino and ethylamino. Examples of "N,N—($C_{1-6}$alkyl)$_2$amino" are N,N-dimethylamino, N,N-diethylamino and N-ethyl-N-methylamino.

As used herein, the term "carbocyclyl", whether as part of another term or used independently, refers to a saturated, monocyclic ring in which all the ring atoms are carbon and which contains at least three ring forming carbon atoms. In some embodiments, the carbocyclyl may contain 3 to 7 ring forming carbon atoms or 3 to 6 ring forming carbon atoms. In some embodiments a ring —$CH_2$— group may be replaced by a ring —C(O)— group. Examples of carbocyclyl groups include, but are not limited to, cyclopropyl, cyclobutyl, cyclopentyl, cyclohexyl and cycloheptyl.

As used herein, the term "heterocyclyl" refers to a monocyclic, saturated carbocyclyl group wherein one or more (e.g. 1, 2 or 3) ring atoms are replaced by heteroatoms which include, but are not limited to, oxygen, sulfur, nitrogen, phosphorus, and the like. In some embodiments a ring —$CH_2$— group may be replaced by a ring —C(O)— group. In some embodiments a ring sulphur atom may be optionally oxidised to form the S-oxides. In some embodiments the heterocycyl is carbon linked. In some embodiments the heterocycyl is nitrogen linked. Exemplary heterocyclyl groups include, but are not limited to azetidinyl, piperidyl, pyrrolidinyl, tetrahydrofuryl, piperidinyl, piperazinyl, morpholinyl, and the like.

In one embodiment two $R^2$ on the same atom, together with the atom to which they are attached, form a 3-7 membered ring. The resultant "spiro rings" have two rings (one of which is the oxane of formula (I)) connected through one single common atom. The non-oxane ring may be a 3-7 membered carbocyclyl ring or a 3-7 membered heterocycle ring. Examples of two $R^2$ on the same atom together with the atom to which they are attached forming a 3-7 membered ring (depicted with the oxane of formula (I)) include:

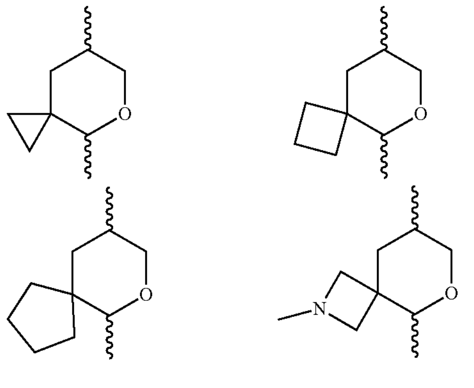

-continued

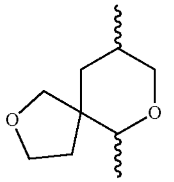

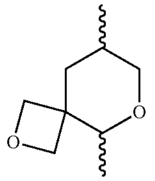

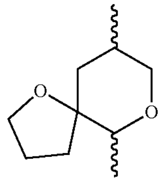

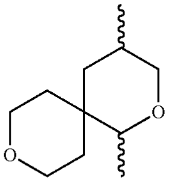

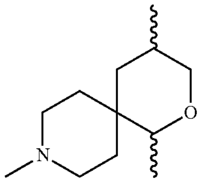

(wherein "〰" depicts the attachment to the rest of the molecule).

In one embodiment, two $R^2$ on adjoining atoms together with the atoms to which they are attached form a 3-7 membered ring. The resultant "fused rings" have two rings (one of which is the oxane of formula (I)) sharing two adjacent atoms. The non-oxane ring may be a 3-7 membered carbocyclyl ring or a 3-7 membered heterocycle ring. Examples of or two $R^2$ on adjoining atoms together forming a 3-7 membered ring (depicted with the oxane of formula (I)) include:

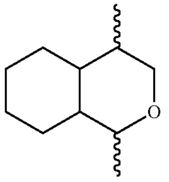

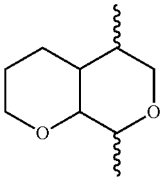

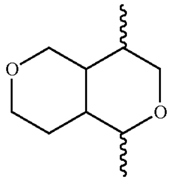

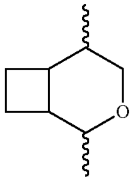

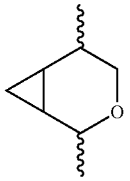

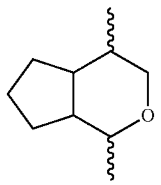

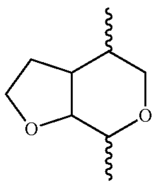

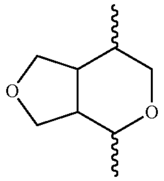

-continued

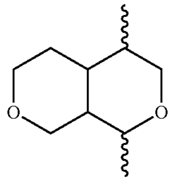

(wherein "〰" depicts the attachment to the rest of the molecule).

The "compound" of present disclosure is intended to encompass all stereoisomers, geometric isomers, and tautomers of the structures depicted unless otherwise specified.

The term "stereoisomer" refers to any of the various stereoisomeric configurations (e.g. enantiomers, diastereomers and racemates) of an asymmetric compound (e.g. those having one or more asymmetrically substituted carbon atoms or "asymmetric centers"). Compounds of the present disclosure that contain asymmetric centers can be isolated in optically active (enantiomers or diastereomers) or optically inactive (racemic) forms. The term "enantiomer" includes pairs of stereoisomers that are non-superimposable mirror images of each other. A 1:1 mixture of a pair of enantiomers is a "racemic mixture". The terms "diastereomers" or "diastereoisomers" include stereoisomers that have at least two asymmetric atoms, but which are not mirror images of each other. Certain compounds containing one or more asymmetric centres may give rise to enantiomers, diastereomers or other stereoisomeric forms that may be defined, in terms of absolute configuration, as (R)- or (S)- at each asymmetric centre according to the Cahn-Ingold-Prelog R-S system. Resolved compounds whose absolute configuration is unknown can be designated using the term "or" at the asymmetric centre. Methods on how to prepare optically active forms from racemic mixtures are known in the art, such as resolution by HPLC or stereoselective synthesis.

The terms "geometric isomers" or "cis and trans isomers" refer to compounds with same formula but their functional groups are rotated into a different orientation in three-dimensional space.

The term "tautomers" include prototropic tautomers that are isomeric protonation states of compounds having the same formula and total charge. Examples of prototropic tautomers include, but are not limited to, ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomers can be in equilibrium or sterically locked into one form by appropriate substitution. Compounds of the present disclosure identified by name or structure as one particular tautomeric form are intended to include other tautomeric forms unless otherwise specified.

The "compound" of the present disclosure is also intended to encompass all isotopes of atoms in the compounds. Isotopes of an atom include atoms having the same atomic number but different mass numbers. For example, unless otherwise specified, hydrogen, carbon, nitrogen, oxygen, phosphorous, sulphur, fluorine, chlorine, bromide or iodine in the "compound" of present disclosure are meant to also include their isotopes such as but are not limited to: $^{1}H$, $^{2}H$, $^{3}H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{19}F$, $^{35}Cl$, $^{37}Cl$, $^{79}Br$, $^{81}Br$, $^{127}I$ and $^{131}I$. In some embodiments, hydrogen includes protium, deuterium and tritium. In some embodiments, hydrogen refers to protium. In some embodiments, hydrogen refers to deuterium. In some embodiments, hydrogen refers to tritium. In some embodiments, the term "substituted by deuterium" or "deuterium substituted" to replace the other isoform of hydrogen (e.g. protium) in the chemical group with deuterium. In some embodiments, carbon includes $^{12}C$ and $^{13}C$.

It is also to be understood that the "compound" of present disclosure can exist in solvated as well as unsolvated forms, such as, for example, hydrated forms, solid forms, and the present disclosure is intended to encompass all such solvated and unsolvated forms.

It is further to be understood that the "compound" of present disclosure can exist in forms of pharmaceutically acceptable salts.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments, compounds, materials, compositions, and/or dosage forms that are pharmaceutically acceptable refer to those approved by a regulatory agency (such as U.S. Food and Drug Administration, China Food and Drug Administration or European Medicines Agency) or listed in generally recognized pharmacopoeia (such as U.S. Pharmacopoeia, China Pharmacopoeia or European Pharmacopoeia) for use in animals, and more particularly in humans.

As used herein, "pharmaceutically acceptable salts" refers to derivatives of the compounds of present disclosure wherein the parent compound is modified by converting an existing acidic moiety (e.g. carboxyl and the like) or base moiety (e.g. amine, alkali and the like) to its salt form. In many cases, compounds of present disclosure are capable of forming acid and/or base salts by virtue of the presence of amino and/or carboxyl groups or groups similar thereto. And the pharmaceutically acceptable salts are acid and/or base salts that retain biological effectiveness and properties of the parent compound, which typically are not biologically or otherwise undesirable. Suitable pharmaceutically acceptable salts of a compound of the present disclosure includes, for example, an acid-addition salt, which can be derived from for example an inorganic acid (for example, hydrochloric, hydrobromic, sulfuric, nitric, phosphoric acid and the like) or organic acid (for example, formic, acetic, propionic, glycolic, oxalic, maleic, malonic, succinic, fumaric, tartaric, trimesic, citric, lactic, phenylacetic, benzoic, mandelic, methanesulfonic, napadisylic, ethanesulfonic, toluenesulfonic, trifluoroacetic, salicylic, sulfosalicylic acids and the like).

Suitable pharmaceutically acceptable salts of a compound of the present disclosure also include, for example, an base-addition salt, which can be derived from for example an inorganic bases (for example, sodium, potassium, ammonium salts and hydroxide, carbonate, bicarbonate salts of metals from columns I to XII of the periodic table such as calcium, magnesium, iron, silver, zinc, copper and the like) or organic bases (for example, primary, secondary, and tertiary amines, substituted amines including naturally occurring substituted amines, cyclic amines, basic ion exchange resins, and the like). Certain organic amines include but are not limited to isopropylamine, benzathine, cholinate, diethanolamine, diethylamine, lysine, meglumine, piperazine and tromethamine. The skilled person would appreciate that adding acids or bases for forming acid/base-addition salts other than those shown in the examples may also be possible. Lists of additional suitable salts can be found, e.g. in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

We have found that the compounds defined in the present invention, or a pharmaceutically acceptable salt thereof, are effective BTK inhibitors, and may be used to produce a BTK inhibitory effect in a warm-blooded animal in need of such treatment. Accordingly, the compounds of the present invention are expected to be useful in the treatment of diseases or medical conditions mediated alone or in part by BTK.

Accordingly, the compounds of the present invention are expected to be useful in the treatment of immune disorders, cancer, cardiovascular diseases, viral infections, metabolism/endocrine function disorders, and neurological disorders, allergic disorders, autoimmune diseases, and inflammatory diseases including Urticaria/Sjogren's syndrome, rheumatoid arthritis, osteoporosis, vasculitis, idiopathic thrombocytopenic purpura (ITP), myasthenia gravis, allergic rhinitis, asthma, multiple sclerosis and systemic lupus erythematosus.

As a result of their BTK inhibitor properties, compounds of the invention are expected to possess a wide range of anti-cancer properties BTK mediated growth been observed in human cancers, including but not limited to, B cell malignancies. In particular such compounds of the invention are expected to be useful in the treatment of lymphomas and leukaemias. More particularly such compounds of the invention, or a pharmaceutically acceptable salt thereof, are expected to be useful in the treatment of small lymphocytic lymphoma (SLL), follicular lymphoma, Richter's transformation, mantle cell lymphoma, chronic lymphocytic leukaemia (CLL), Waldenström's macroglobulinemia, non-Hodgkin lymphoma, primary central nervous system lymphoma, secondary central nervous system is lymphoma or diffuse large B-cell lymphoma. Particularly the compounds of the present invention are useful in the treatment of diffuse large B-cell lymphoma that has metastasized to the brain, primary central nervous system lymphoma or secondary central nervous system lymphoma. Particularly the compounds of the present invention are useful in the treatment of chronic lymphocytic leukaemia. Particularly the compounds of the present invention are useful in the second line treatment of chronic lymphocytic leukaemia. Particularly the compounds of the present invention are useful in the first line treatment of chronic lymphocytic leukaemia. Particularly the compounds of the present invention are useful in the treatment of diffuse large B-cell lymphoma. Particularly the compounds of the present invention are useful in the treatment of primary central nervous system lymphoma.

In some embodiments, the compounds, or pharmaceutically acceptable salts thereof, of the present disclosure possess anti-cancer activity in early stage, actively progressing, metastatic and/or drug-resistant cancers. In some embodiments where cancer is referred to the cancer is locally advanced cancer. In some embodiments where cancer is referred to the cancer is locally advanced and/or metastatic cancer. In some embodiments where cancer is referred to the cancer is metastatic cancer. In some embodiments where cancer is referred to the cancer is invasive cancer. In some embodiments where cancer is referred to the cancer is ibrutinib resistant cancer.

In one embodiment of the invention, where BTK inhibition is mentioned, this refers to both wild-type BTK, and BTK with a C481 mutation (for example a C481S, C481Y, C481R or C481F mutation).

In one embodiment of the invention, where BTK inhibition is mentioned, this refers to wild-type BTK.

In one embodiment of the invention, where BTK inhibition is mentioned, this refers to BTK with a C481 mutation.

In one embodiment of the invention, where BTK inhibition is mentioned, this refers to BTK with a C481S mutation.

In one embodiment of the invention, where BTK inhibition is mentioned, this refers to BTK with a C481Y mutation.

In one embodiment of the invention, where BTK inhibition is mentioned, this refers to BTK with a C481R mutation.

In one embodiment of the invention, where BTK inhibition is mentioned, this refers to BTK with a C481F mutation.

Pharmaceutical Composition, Dose and Administration

The present disclosure provides pharmaceutical compositions comprising at least one compound of the present disclosure, or a pharmaceutically acceptable salt thereof. In some embodiments, the pharmaceutical composition comprises more than one compound of the present disclosure, or a pharmaceutically acceptable salt thereof. In some embodiments, the pharmaceutical composition comprises one or more compounds of the present disclosure, or a pharmaceutically acceptable salt thereof, and a pharmaceutical acceptable carrier.

In general, the pharmaceutically acceptable carriers are conventional medicinal carriers in the art which can be prepared in a manner well known in the pharmaceutical art. In some embodiments, the compounds of the present disclosure, or a pharmaceutically acceptable salt thereof, may be admixed with pharmaceutically acceptable carrier for the preparation of pharmaceutical composition.

The form of pharmaceutical compositions depends on a number of criteria, including, but not limited to, route of administration, extent of disease, or dose to be administered. The pharmaceutical compositions can be formulated for oral, nasal, rectal, percutaneous, intravenous, or intramuscular administration. In accordance to the desired route of administration, the pharmaceutical compositions can be formulated in the form of tablets, capsule, pill, powder, granule, sachets, cachets, lozenges, suspensions, emulsions, solutions, syrups, aerosols (as a solid or in a liquid medium), spray, ointment, paste, cream, lotion, gel, patch, inhalant, or suppository.

In certain embodiments, the pharmaceutical compositions comprise about 1 mg to about 500 mg of the compounds of the present disclosure, or a pharmaceutically acceptable salt thereof, particularly 1 mg to about 200 mg. The pharmaceutical composition may also be administered once, twice, three times or even four times a day. However, the daily dose will necessarily be varied depending upon the host treated, the particular route of administration, and the severity of the illness being treated. Accordingly the optimum dosage may be determined by the practitioner who is treating any particular patient.

The therapeutically effective amount of a compound or a pharmaceutically acceptable salts thereof as provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g. physician or veterinarian) as indicated by these and other circumstances or requirements.

In a further aspect of the invention there is provided a pharmaceutical composition which comprises a compound of formula (I) or a pharmaceutically acceptable salt thereof, as defined herein in association with a pharmaceutically-acceptable diluent or carrier.

In a further aspect of the invention there is provided a pharmaceutical composition which comprises a compound of formula (I) or a pharmaceutically acceptable salt thereof, as defined herein in association with a pharmaceutically-acceptable diluent or carrier for use in the production of a BTK inhibitory effect in a warm-blooded animal such as man.

In a further aspect of the invention there is provided a pharmaceutical composition which comprises a compound of formula (I) or a pharmaceutically acceptable salt thereof, as defined herein in association with a pharmaceutically-acceptable diluent or carrier for use in the production of an anti-cancer effect in a warm-blooded animal such as man.

In a further aspect of the invention there is provided a pharmaceutical composition which comprises a compound of formula (I) or a pharmaceutically acceptable salt thereof, as defined herein in association with a pharmaceutically-acceptable diluent or carrier for use in the treatment of small lymphocytic lymphoma (SLL), follicular lymphoma, Richter's transformation, mantle cell lymphoma, chronic lymphocytic leukaemia (CLL), Waldenström's macroglobulinemia, non-Hodgkin lymphoma, primary central nervous system lymphoma, secondary central nervous system lymphoma or diffuse large B-cell lymphoma in a warm-blooded animal such as man.

In a further aspect of the invention there is provided a pharmaceutical composition which comprises a compound of formula (I) or a pharmaceutically acceptable salt thereof, as defined herein in association with a pharmaceutically-acceptable diluent or carrier for use in the treatment of diffuse large B-cell lymphoma that has metastasized to the brain, primary central nervous system lymphoma or secondary central nervous system lymphoma.

Combinations

In some embodiments, the pharmaceutical compositions comprise one or more compounds of the present disclosure, or a pharmaceutically acceptable salt thereof, as a first active ingredient, and further comprise a second active ingredient. The second active ingredient can be any anti-tumour agent known in the art, for examples, PI3K inhibitors, anti CD20 antibodies, anti PD-1/L1 antibodies, and other approved drug or drug combination for Non-Hodgkin lymphoma. Representative examples of the second active ingredient anti tumour agents include, but are not limited to, idelalisib, duvelisib, obinutuzumab, ofatumumab, rituximab, alemtuzumab, bleomycin, brentuximab, vedotin, carmustine, cyclophosphamide, chlorambucil, dacarbazine, dexamethasone, doxorubicin, lomustine, mechlorethamine, procarbazine, prednisone, bendamustine, venetoclax, prednisone, CVP (a combination treatment of C—Cyclophosphamide, a chemotherapy drug, V—Vincristine, a chemotherapy drug and P—Prednisolone, a steroid), midostaurin and vinblastine.

Herein, where the term "combination" is used it is to be understood that this refers to simultaneous, separate or sequential administration. In one aspect of the present disclosure, "combination" refers to simultaneous administration. In another aspect of the present disclosure, "combination" refers to separate administration. In a further aspect of the present disclosure, "combination" refers to sequential administration. Where the administration is sequential or separate, the delay in administering the second component should not be such as to lose the beneficial effect of the combination.

Therefore in a further aspect of the present disclosure, there is provided a compound of formula (I) or a pharmaceutically acceptable salt thereof, as defined herein in combination with an anti-tumour is agent selected from one listed herein above.

Therefore in a further aspect of the present disclosure, there is provided a compound of formula (I) or a pharmaceutically acceptable salt thereof, as defined herein in combination with an anti-tumour agent selected from one listed herein above for use in producing an anti-cancer effect.

Therefore in a further aspect of the present disclosure, there is provided a compound of formula (I) or a pharmaceutically acceptable salt thereof, as defined herein in combination with an anti-tumour agent selected from one listed herein above for use in treating small lymphocytic lymphoma (SLL), follicular lymphoma, Richter's transformation, mantle cell lymphoma, chronic lymphocytic leukaemia (CLL), Waldenström's macroglobulinemia, non-Hodgkin lymphoma, primary central nervous system lymphoma, secondary central nervous system lymphoma or diffuse large B-cell lymphoma.

Therefore in a further aspect of the present disclosure, there is provided a compound of formula (I) or a pharmaceutically acceptable salt thereof, as defined herein in combination with an anti-tumour agent selected from one listed herein above for use in treating diffuse large B-cell lymphoma that has metastasized to the brain, primary central nervous system lymphoma or secondary central nervous system lymphoma.

According to this aspect of the present disclosure, there is provided a combination suitable for use in the treatment of cancer comprising a compound of formula (I) or a pharmaceutically acceptable salt thereof, as defined herein and any one of the anti-tumour agents listed above.

According to a further aspect of the present disclosure, there is provided a pharmaceutical composition which comprises a compound of formula (I) or a pharmaceutically acceptable salt thereof, as defined herein in combination with an anti-tumour agent selected from one listed herein above, in association with a pharmaceutically acceptable diluent or carrier.

According to a further aspect of the present disclosure, there is provided a pharmaceutical composition which comprises a compound of formula (I) or a pharmaceutically acceptable salt thereof, as defined herein in combination with an anti-tumour agent selected from one listed herein above, in association with a pharmaceutically acceptable diluent or carrier for use in producing an anti-cancer effect.

According to a further aspect of the present disclosure, there is provided a pharmaceutical composition which comprises a compound of formula (I) or a pharmaceutically acceptable salt thereof, as defined herein in combination with an anti-tumour agent selected from one listed herein above, in association with a pharmaceutically acceptable diluent or carrier for use in treating small lymphocytic lymphoma (SLL), follicular lymphoma, Richter's transformation, mantle cell lymphoma, chronic lymphocytic leukaemia (CLL), Waldenström's macroglobulinemia, non-Hodgkin lymphoma, primary central nervous system lymphoma, secondary central nervous system lymphoma or diffuse large B-cell lymphoma.

According to a further aspect of the present disclosure, there is provided a pharmaceutical composition which comprises a compound of formula (I) or a pharmaceutically acceptable salt thereof, as defined herein in combination with an anti-tumour agent selected from one listed herein above, in association with a pharmaceutically acceptable diluent or carrier for use in treating diffuse large B-cell lymphoma that has metastasized to the brain, primary central nervous system lymphoma or secondary central nervous system lymphoma.

According to a further aspect of the present disclosure, there is provided a kit comprising a compound of formula (I) or a pharmaceutically acceptable salt thereof, as defined herein in combination with an anti-tumour agent selected from one listed herein above.

According to a further aspect of the present disclosure, there is provided a kit comprising:

a) a compound of formula (I) or a pharmaceutically acceptable salt thereof, as defined herein in a first unit dosage form;
b) an anti-tumour agent selected from one listed herein above; in a second unit dosage form; and
c) container means for containing said first and second dosage forms.

Pharmacological Tools

In addition to their use in therapeutic medicine, the compounds of formula (I), or a pharmaceutically acceptable salt thereof, are also useful as pharmacological tools in the development and standardisation of in vitro and in vivo test systems for the evaluation of the effects of BTK inhibition in laboratory animals such as cats, dogs, rabbits, monkeys, rats and mice, as part of the search for new therapeutic agents.

Method of Treatment

According to a further aspect of the present invention there is provided a compound of formula (I) or a pharmaceutically acceptable salt thereof, as defined herein for use in a method of treatment of the human or animal body by therapy.

According to a further feature of this aspect of the invention there is provided a method of producing a BTK inhibitory effect in a warm-blooded animal, such as man, which comprises administering to said animal an effective amount of a compound of formula (I) or a pharmaceutically acceptable salt thereof, as defined herein.

According to a further feature of this aspect of the invention there is provided a method of treating cancer in a warm-blooded animal, such as man, which comprises administering to said animal an effective amount of a compound of formula (I) or a pharmaceutically acceptable salt thereof, as defined herein.

According to an additional feature of this aspect of the invention there is provided a method of treating small lymphocytic lymphoma (SLL), follicular lymphoma, Richter's transformation, mantle cell is lymphoma, chronic lymphocytic leukaemia (CLL), Waldenström's macroglobulinemia, non-Hodgkin lymphoma, primary central nervous system lymphoma, secondary central nervous system lymphoma or diffuse large B-cell lymphoma, in a warm-blooded animal, such as man, which comprises administering to said animal an effective amount of a compound of formula (I) or a pharmaceutically acceptable salt thereof, as defined herein.

According to an additional feature of this aspect of the invention there is provided a method of treating diffuse large B-cell lymphoma that has metastasized to the brain, primary central nervous system lymphoma or secondary central nervous system lymphoma, in a warm-blooded animal, such as man, which comprises administering to said animal an effective amount of a compound of formula (I) or a pharmaceutically acceptable salt thereof, as defined herein.

As used herein, the terms "treatment" and "treat" refer to reversing, alleviating, delaying the onset of, or inhibiting the progress of a disease or disorder, or one or more symptoms thereof, as described herein. In some embodiments, treatment may be conducted after one or more symptoms have developed. In other embodiments, treatment may be conducted in the absence of symptoms. For example, treatment may be conducted to a susceptible individual prior to the onset of symptoms (e.g. in light of a history of symptoms and/or in light of genetic or other susceptibility factors). Treatment may also be continued after symptoms have resolved, for example to present or delay their recurrence.

The present disclosure also provides a method of screening a patient suitable for treating with a compound of formula (I) or a pharmaceutically acceptable salt thereof, as defined herein. The method includes sequencing the tumour samples from patients and detecting the accumulation of BTK or the presence of BTK mutations.

According to a further feature of this aspect of the present disclosure, there is provided a method of treating cancer in a warm-blooded animal, such as man, which comprises (1) determining whether or not the warm blooded animal has a cancer receptive to BTK inhibition and (2) if so administering to said animal an effective amount of a compound of formula (I) or a pharmaceutically acceptable salt thereof, as defined herein.

Use of Compounds

In certain embodiments, the present disclosure provides use of the compounds, pharmaceutically acceptable salts thereof, or pharmaceutical composition of the present disclosure in the manufacture of medicaments for the treatment of BTK mediated or dependent diseases or conditions.

Thus according to this aspect of the invention there is provided a compound of formula (I) or a pharmaceutically acceptable salt thereof, as defined herein for use as a medicament.

Thus according to this aspect of the invention there is provided the use of a compound of is formula (I) or a pharmaceutically acceptable salt thereof, as defined herein as a medicament.

Thus according to this aspect of the invention there is provided a compound of formula (I) or a pharmaceutically acceptable salt thereof, as defined herein for use in therapy.

According to a further aspect of the invention there is provided the use of a compound of formula (I) or a pharmaceutically acceptable salt thereof, as defined herein in the manufacture of a medicament for the production of a BTK inhibitory effect in a warm-blooded animal such as man.

According to this aspect of the invention there is provided the use of a compound of formula (I) or a pharmaceutically acceptable salt thereof, as defined herein in the manufacture of a medicament for the production of an anti-cancer effect in a warm-blooded animal such as man.

According to a further feature of the invention, there is provided the use of a compound of formula (I) or a pharmaceutically acceptable salt thereof, as defined herein in the manufacture of a medicament for the treatment of small lymphocytic lymphoma (SLL), follicular lymphoma, Richter's transformation, mantle cell lymphoma, chronic lymphocytic leukaemia (CLL), Waldenström's macroglobulinemia, non-Hodgkin lymphoma, primary central nervous system lymphoma, secondary central nervous system lymphoma or diffuse large B-cell lymphoma.

According to a further feature of the invention, there is provided the use of a compound of formula (I) or a pharmaceutically acceptable salt thereof, as defined herein in the manufacture of a medicament for the treatment of diffuse large B-cell lymphoma that has metastasized to the brain, primary central nervous system lymphoma or secondary central nervous system lymphoma.

According to a further aspect of the invention there is provided the use of a compound of formula (I) or a pharmaceutically acceptable salt thereof, as defined herein for use in the production of a BTK inhibitory effect in a warm-blooded animal such as man.

According to this aspect of the invention there is provided the use of a compound of formula (I) or a pharmaceutically acceptable salt thereof, as defined herein for use in the production of an anti-cancer effect in a warm-blooded animal such as man.

According to a further feature of the invention, there is provided a compound of formula (I) or a pharmaceutically acceptable salt thereof, as defined herein for use in the treatment of small lymphocytic lymphoma (SLL), follicular lymphoma, Richter's transformation, mantle cell lymphoma, chronic lymphocytic leukaemia (CLL), Waldenström's macroglobulinemia, non-Hodgkin lymphoma, primary central nervous system lymphoma, secondary central nervous system lymphoma or diffuse large B-cell lymphoma.

According to a further feature of the invention, there is provided a compound of formula (I) or a pharmaceutically acceptable salt thereof, as defined herein for use in the treatment of diffuse large B-cell lymphoma that has metastasized to the brain, primary central nervous system lymphoma or secondary central nervous system lymphoma.

In the above pharmaceutical compositions, methods, uses and medicament manufacture is features, the alternative and preferred embodiments of the compounds of the present disclosure, described herein also apply.

EXAMPLES

General Experimental

Abbreviations

| Abbreviations | Full name |
|---|---|
| NBS | N-bromosuccinimide |
| PTFE | polytetrafluoro ethylene |
| DMSO | dimethyl sulfoxide |
| TFA | trifluoroacetic acid |
| WB | Western Blot |
| HATU | Hexafluorophosphate azabenzotriazole tetramethyl uronium |
| DIEA | Diisopropylethylamine |
| LAH | Lithium aluminum hydride |
| DMF | N,N-Dimethylformamide |
| THF | Tetrahydrofuran |
| IPA | 2-Propanol |
| NMM | N-methylmorpholine |
| EDTA | Ethylenediaminetetraacetic acid |
| ATP | Adenosine-5'-triphosphate |
| DMEM | Dulbecco's Modified Eagle Medium |
| dppf | 1,1'-Bis(diphenylphosphino)ferrocene |

Synthesis of the compounds provided herein, including pharmaceutically acceptable salts thereof, are illustrated in the synthetic schemes in the examples. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Methods are for better illustration and can be changed as appropriate. The embodiments of the compounds in examples were synthesized for the purposes of research and potentially submission to regulatory agencies.

The reactions for preparing compounds of the present disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g. temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by a skilled artisan.

Preparation of compounds of the present disclosure can involve the protection and is deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g. $^1$H or $^{13}$C), infrared spectroscopy, spectrophotometry (e.g. UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety), supercritical fluid chromatography (SFC), and normal phase silica chromatography.

The structures of the compounds in the examples are characterized by nuclear magnetic resonance (NMR) or/and liquid chromatography-mass spectrometry (LC-MS). NMR chemical shift (5) is given in the unit of $10^{-6}$ (ppm). $^1$H-NMR spectra is recorded in dimethyl sulfoxide-$d_6$ (DMSO-$d_6$) or $CDCl_3$ or $CD_3OD$ or $D_2O$ or acetone-$d_6$ or $CD_3CN$ (from Aldrich or Cambridge Isotope Lab., Inc.) on Bruker AVANCE NMR (400 MHz) spectrometers using ICON-NMR (under TopSpin program control), or Varian 400MR NMR or Varian VNMR400 NMR (400 MHz) spectrometers (under VnmrJ program control) with tetramethylsilane as an internal standard.

MS measurement is carried out using Shimadzu 2010 Mass Spectrometer or Agilent 6110A MSD or 1969A TOF mass spectrometer using electrospray, chemical and electron impact ionization methods from a range of instruments. The detailed methods used in this invention include: LC-MS Method A: 10-80AB_7 min_220 &254_Shimadzu.lcm Mobile Phase: 1.5 mL/4 L TFA in water (solvent A) and 0.75 mL/4 L TFA in acetonitrile (solvent B), using the elution gradient 10%-80% (solvent B) over 6 minutes and holding at 80% for 0.5 minutes at a flow rate of 0.8 mL/min;

Column: Xtimate C18 2.1*30 mm, 3 μm;

Wavelength: UV 220 nm, 254 nm;

Column temperature: 50° C.;

MS ionization: ESI

LC-MS Method B: 10-80AB_4 min_220 &254_Shimadzu.lcm

Mobile Phase: 1.5 mL/4 L TFA in water (solvent A) and 0.75 mL/4 L TFA in acetonitrile (solvent B), using the elution gradient 10%-80% (solvent B) over 3 minutes and holding at 80% for 0.5 minutes at a flow rate of 0.8 mL/min;

Column: Xtimate C18 2.1*30 mm, 3 μm;

Wavelength: UV 220 nm, 254 nm;

Column temperature: 50° C.;

MS ionization: ESI

LC-MS Method C: 10-80CD_7 min_220 &254_Agilent.lcm

Mobile Phase: 0.2 mL/1 L $NH_3 \cdot H_2O$ in water (solvent A) and acetonitrile (solvent B), using the elution gradient 10%-80% (solvent B) over 6 minutes and holding at 80% for 0.5 minutes at a flow rate of 0.8 mL/min;

Column: Xbrige Shield RP-18, 5 μm, 2.1*50 mm;

Wavelength: UV 220 nm & 254 nm;

Column temperature: 30° C.;

MS ionization: ESI

High Performance Liquid Chromatography (HPLC) measurement is carried out on Shimadzu LC-20A systems or Shimadzu LC-2010HT series, or Agilent 1200 LC or Agilent 1100 series using Ultimate XB—C18 column (3.0*50 mm, 3 μm or 3.0*150 mm, 3 μm), or Xbridge shieldRP18 column (5 μm, 50 mm*2.1 mm), or Xtimate C18 column (3 μm, 2.1*30 mm), or MERCK RP18 2.5-2 mm etc. The detailed methods used in this invention include:

HPLC Method A: 10-80AB_8 min.met

Mobile Phase: 2.75 mL/4 L TFA in water (solvent A) and 2.5 mL/4 L TFA in acetonitrile (solvent B), using the elution gradient 10%-80% (solvent B) over 6 minutes and holding at 80% for 2 minutes at a flow rate of 1.2 mL/min;

Column: Ultimate C18 3.0*50 mm, 3 μm

Wavelength: UV220 nm, 215 nm, 254 nm;

Column temperature: 40° C.;

HPLC Method B: 10-80CD_8 min.met

Mobile Phase: 2.0 mL/4 L $NH_3H_2O$ in water (solvent A) and acetonitrile (solvent B), using the elution gradient 10%-80% (solvent B) over 4 minutes and holding at 80% for 2 minutes at a flow rate of 1.2 mL/min;

Column: Xbrige Shield RP-18, 2.1*50 mm, 5 μm;

Wavelength: UV 220 nm, 215 nm, 254 nm;

Column temperature: 40° C.;

Supercritical fluid chromatography (SFC) measurement is carried out on out on Agilent 1260 series, or Waters UPCC series, or Shimadzu LC-20AB series using ChiralPak AD-3 column (3 μm, 150×4.6 mm), or Chiralcel OJ-3 column (3 μm, 150×4.6 mm), or Chiralpak IG-3 column (3 μm, 50 mm*4.6 mm) etc. The detailed methods used in this invention include:

SFC Method A: Mobile phase: A: $CO_2$ B: Ethanol (0.05% DEA), Gradient: from 5% to 40% of B in 5.5 min and hold 40% for 3 min, then 5% of B for 1.5 min, Flow rate: 2.5 mL/min;

Column: ChiralPak AD-3 150×4.6 mm I.D., 3 μm;

Column temp.: 40° C.;

Back pressure: 100 bar.

SFC Method B: Mobile phase: A: $CO_2$ B: methanol (0.05% DEA) Gradient: from 5% to 40% of B in 5 min and from 40% to 5% of B in 0.5 min, hold 5% of B for 1.5 min Flow rate: 2.5 mL/min Column: Chiralcel OJ-3 150×4.6 mm I.D., 3 μm;

Column temp.: 35° C.;

ABPR: 1500 psi.

SFC Method C: Mobile phase: A: $CO_2$ B: methanol (0.05% DEA), Isocratic: 40% B, Flow rate: 4 mL/min;

Column: Chiralpak IG-3 50 mm*4.6 mm I.D., 3 μm;

Column temp.: 35° C.;

ABPR: 1500 psi.

Thin layer chromatography is carried out using Yantai Huanghai HSGF254 silica gel or Anhui Liang Chen Gui Yuan plates. The silica gel plates used for thin layer chromatography (TLC) are 0.15 mm~0.2 mm. The silica gel plates used for separating and purifying products by TLC are 0.4 mm~0.5 mm.

Purified chromatographic column uses the silica gel as the carrier (100~200, 200~300 or 300~400 mesh, produced by Yantai Huanghai co., or Anhui Liang Chen Gui Yuan co., etc.), or flash column (silica-CS flash column 40-60 μm, or reversed phase C18 column 20-35 μm, produced by Agela Technologies, etc.) or flash column silica-CS (40-60 μm) or C18 column (20-40 μm) by Agela Technologies in the Teledyne ISCO combi-flash or Biotage flash system. The size of columns are adjusted according to the amount of compounds.

The known starting materials of the present disclosure can be synthesized by using or according to the known methods in the art, or can be purchased from Alfa Aesar, TCI, Aldrich, Bepharm, and Scochem (or PharmaBlock, Bide, Amatek, Stru Chem, Firster Pharmaceutical, Titan (Adamas) etc.).

Unless otherwise specified, the reactions are all carried out under argon or nitrogen atmosphere. Argon or nitrogen atmosphere refers to that the reaction flask is connected to an argon or nitrogen balloon with a volume of about 1 L. Hydrogenation is usually carried out under pressure. Unless otherwise specified, the reaction temperature in the examples is ambient temperature, which is 10° C.~30° C.

The reaction progress is monitored by TLC or/and LC-MS. The eluent systems used for the reactions include dichloromethane-methanol system and petroleum ether-ethyl acetate system. The volume ratios of the solvents are adjusted according to the different polarities of compounds.

The elution system of column chromatography used for purifying compounds and eluent system is of TLC include dichloromethane-methanol system and petroleum ether-ethyl acetate system. The volume ratios of the solvents are adjusted according to the different polarities of compounds. A small amount of alkaline or acidic agents (0.1%~1%) such as formic acid, or acetic acid, or TFA, or ammonia can be added for adjustment.

Compounds of the Invention

TABLE 1

| Compounds of the Invention | |
|---|---|
| Cpd. No. | Compound Structure and Name |
| 1 | 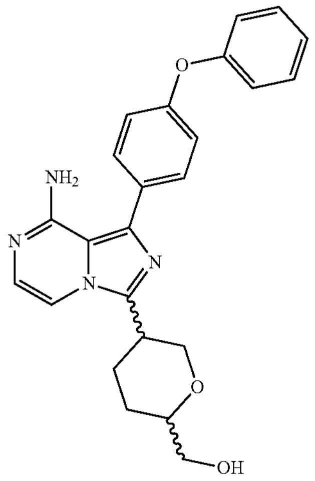 Trans isomer 1 & 2 (5-(8-amino-1-(4-phenoxyphenyl)imidazo[1,5-a]pyrazin-3-yl)tetrahydro-2H-pyran-2-yl)methanol |
| 2 | 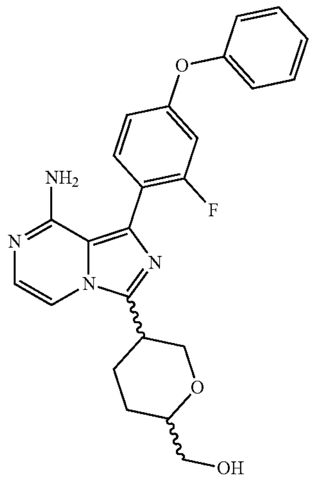 Trans isomer 1 (5-(8-amino-1-(2-fluoro-4-phenoxyphenyl)imidazol[1,5-a]pyrazin-3-yl)tetrahydro-2H-pyran-2-yl)methanol |

TABLE 1-continued

| Compounds of the Invention | |
|---|---|
| Cpd. No. | Compound Structure and Name |
| 3 | 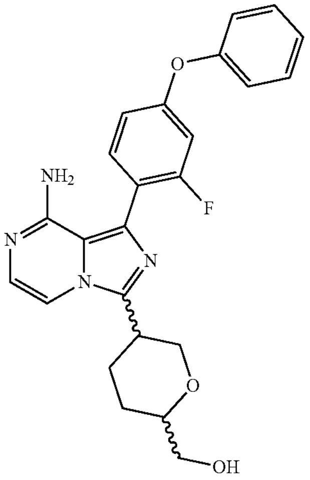 Trans isomer 2 (5-(8-amino-1-(2-fluoro-4-phenoxyphenyl) imidazol[1,5-a]pyrazin-3-yl)tetrahydro-2H-pyran-2-yl)methanol |
| 4 | 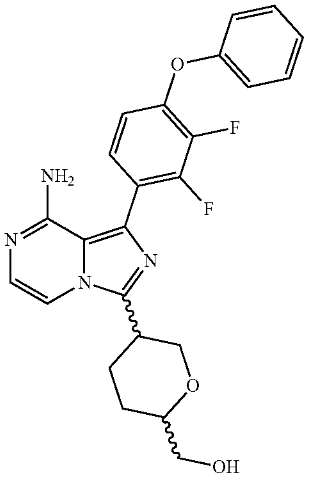 Trans isomer 1 (5-(8-amino-1-(2,3-difluoro-4-phenoxyphenyl) imidazo[1,5-a]pyrazin-3-yl)tetrahydro-2H-pyran-2-yl)methanol |

TABLE 1-continued

| Compounds of the Invention | |
|---|---|
| Cpd. No. | Compound Structure and Name |
| 5 | 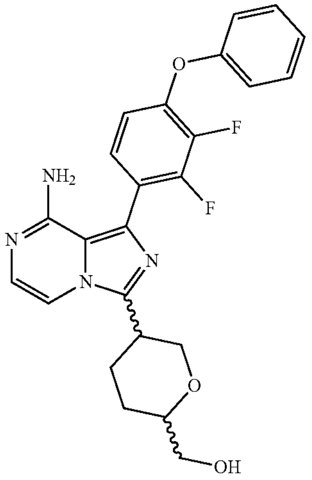 Trans isomer 2 (5-(8-amino-1-(2,3-difluoro-4-phenoxyphenyl) imidazo[1,5-a]pyrazin-3-yl)tetrahydro-2H-pyran-2-yl)methanol |
| 6 | 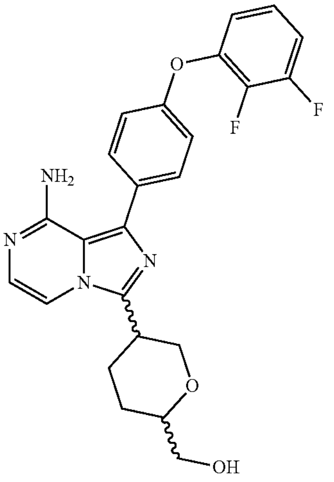 Trans isomer 1 (5-(8-amino-1-(4-(2,3-difluorophenoxy) phenyl)imidazo[1,5-a]pyrazin-3-yl)tetrahydro-2H-pyran-2-yl)methanol |

TABLE 1-continued

| Compounds of the Invention | |
|---|---|
| Cpd. No. | Compound Structure and Name |
| 7 | 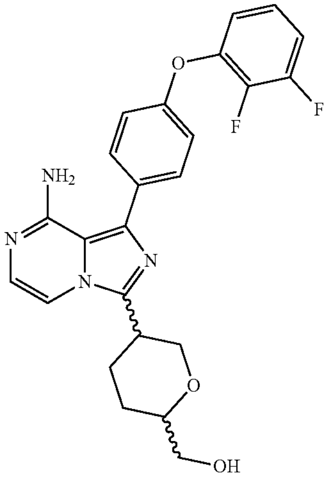 Trans isomer 2<br>(5-(8-amino-1-(4-(2,3-difluorophenoxy) phenyl)imidazo[1,5-a]pyrazin-3-yl)tetrahydro-2H-pyran-2-yl)methanol |
| 8 | 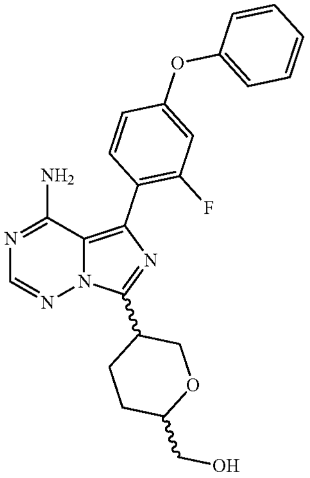 Cis isomer 1<br>(5-(4-amino-5-(2-fluoro-4-phenoxyphenyl) imidazo[5,1-f][1,2,4]triazin-7-yl) tetrahydro-2H-pyran-2-yl)methanol |
| 9 | 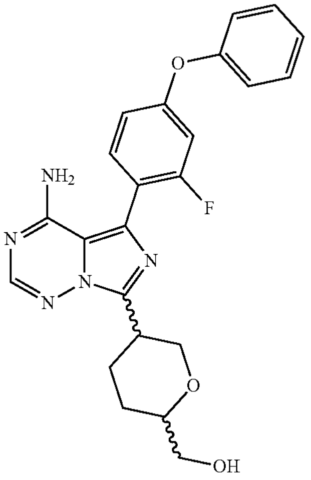 Cis isomer 2<br>(5-(4-amino-5-(2-fluoro-4-phenoxyphenyl) imidazo[1,5-a][1,2,4]triazin-7-yl) tetrahydro-2H-pyran-2-yl)methanol |
| 10 | 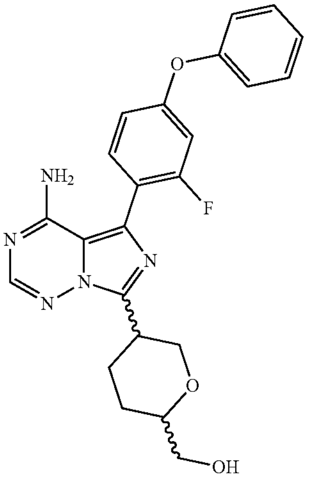 Trans isomer 1<br>(5-(4-amino-5-(2-fluoro-4-phenoxyphenyl) imidazo[5,1-f][1,2,4]triazin-7-yl) tetrahydro-2H-pyran-2-yl)methanol |

TABLE 1-continued

| Compounds of the Invention | |
|---|---|
| Cpd. No. | Compound Structure and Name |
| 11 | 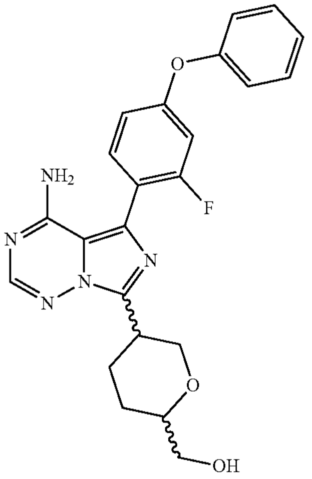<br>Trans isomer 2<br>(5-(4-amino-5-(2-fluoro-4-phenoxyphenyl)imidazo[5,1-f][1,2,4]triazin-7-yl)tetrahydro-2H-pyran-2-yl)methanol |
| 12 | 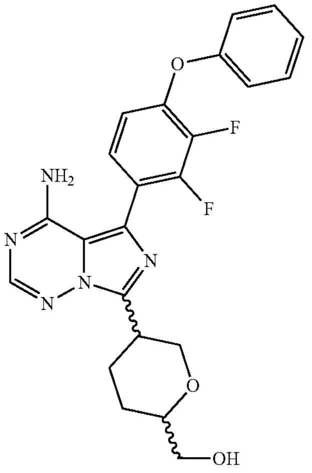<br>Trans isomer 1<br>(5-(4-amino-5-(2,3-difluoro-4-phenoxyphenyl)imidazo[1,5-f][1,2,4]triazin-7-yl)tetrahydro-2H-pyran-2-yl)methanol |

TABLE 1-continued

| Compounds of the Invention | |
|---|---|
| Cpd. No. | Compound Structure and Name |
| 13 | 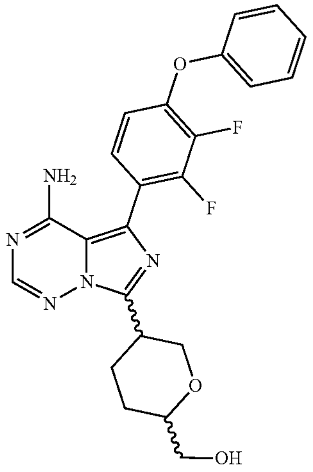<br>Trans isomer 2<br>(5-(4-amino-5-(2,3-difluoro-4-phenoxyphenyl)imidazo[5,1-f][1,2,4]triazin-7-yl)tetrahydro-2H-pyran-2-yl)methanol |
| 14 | 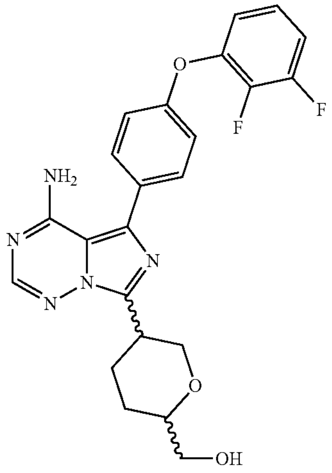<br>Trans isomer 1<br>(5-(4-amino-5-(4-(2,3-difluorophenoxy)phenyl)imidazo[5,1-f][1,2,4]triazin-7-yl)tetrahydro-2H-pyran-2-yl)methanol |

TABLE 1-continued

Compounds of the Invention

| Cpd. No. | Compound Structure and Name |
|---|---|
| 15 | 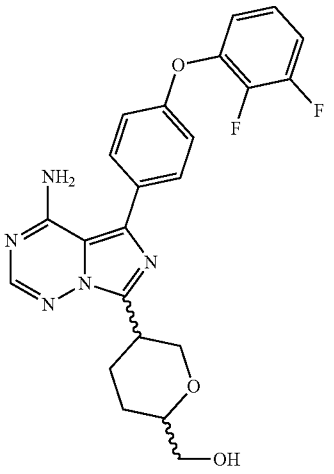<br>Trans isomer 2<br>(5-(4-amino-5-(4-(2,3-difluorophenoxy)phenyl)imidazo[5,1-f][1,2,4]triazin-7-yl)tetrahydro-2H-pyran-2-yl)methanol |
| 16 | 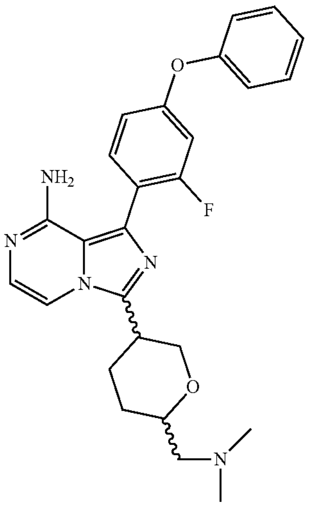<br>Trans isomer 1<br>3-(6-((dimethylamino)methyl)tetrahydro-2H-pyran-3-yl)-1-(2-fluoro-4-phenoxyphenyl)imidazo[1,5-a]pyrazin-8-amine |
| 17 | 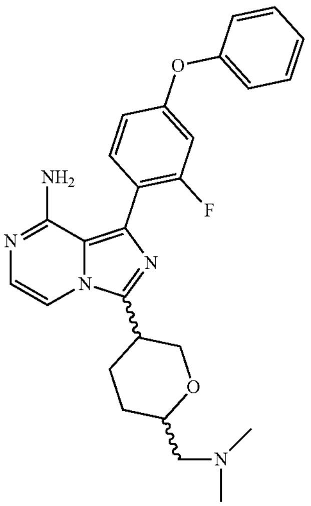 [SMILES: COCC1CCC(c2nc(-c3ccc(Oc4ccccc4)cc3F)c3c(N)ncnn23)CO1]<br>Trans isomer 2<br>3-(6-((dimethylamino)methyl)tetrahydro-2H-pyran-3-yl)-1-(2-fluoro-4-phenoxyphenyl)imidazo[1,5-a]pyrazin-8-amine |
| 18 | 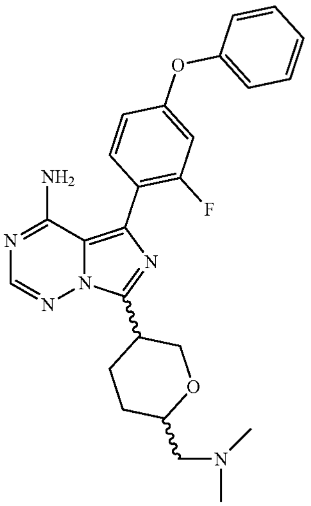 [SMILES: COCC1CCC(c2nc(-c3ccc(Oc4ccccc4)cc3F)c3c(N)ncnn23)CO1]<br>Trans isomer 1<br>7-(6-((dimethylamino)methyl)tetrahydro-2H-pyran-3-yl)-5-(2-fluoro-4-phenoxyphenyl)imidazo[5,1-f][1,2,4]triazin-4-amine |

TABLE 1-continued

| Compounds of the Invention | |
|---|---|
| Cpd. No. | Compound Structure and Name |
| 19 | 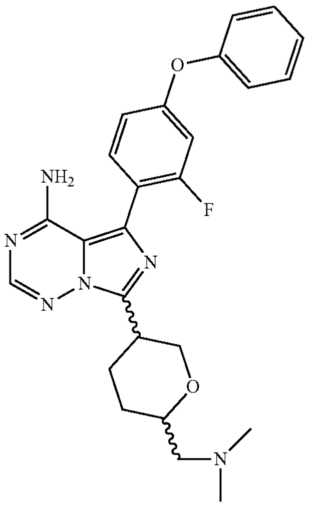<br>Trans isomer 2<br>7-(6-((dimethylamino)methyl)tetrahydro-2H-pyran-3-yl)-5-(2-fluoro-4-phenoxyphenyl) imidazo[5,1-f][1,2,4]triazin-4-amine |
| 20 | 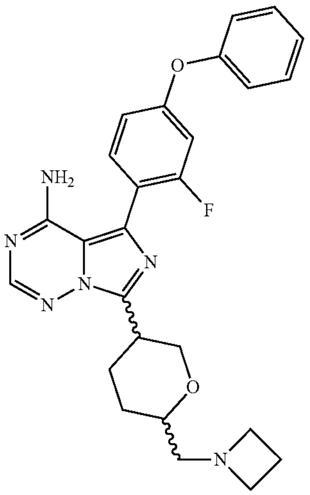<br>Trans isomer 1<br>7-(6-(azetidin-1-ylmethyl)tetrahydro-2H-pyran-3-yl)-5-(2-fluoro-4-phenoxyphenyl) imidazo[5,1-f][1,2,4]triazin-4-amine |

TABLE 1-continued

| Compounds of the Invention | |
|---|---|
| Cpd. No. | Compound Structure and Name |
| 21 | 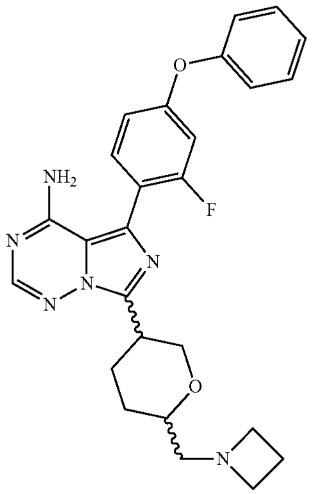<br>Trans isomer 2<br>7-(6-(azetidin-1-ylmethyl)tetrahydro-2H-pyran-3-yl)-5-(2-fluoro-4-phenoxyphenyl)imidazo [5,1-f][1,2,4]triazin-4-amine |
| 22 | 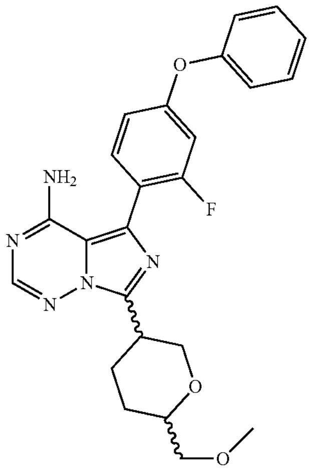<br>Trans isomer 1<br>5-(2-fluoro-4-phenoxyphenyl)-7-(6-(methoxymethyl)tetrahydro-2H-pyran-3-yl)imidazo[5,1-f][1,2,4]triazin-4-amine |

TABLE 1-continued

| Cpd. No. | Compound Structure and Name |
|---|---|
| 23 | 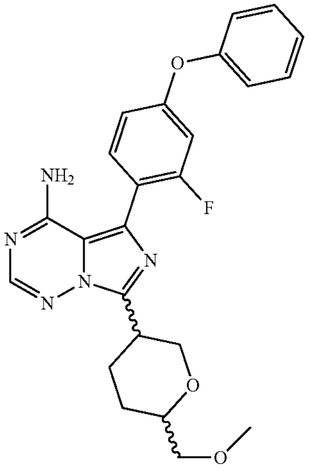 Trans isomer 2 5-(2-fluoro-4-phenoxyphenyl)-7-(6-(methoxymethyl)tetrahydro-2H-pyran-3-yl)imidazo[5,1-f][1,2,4]triazin-4-amine |
| 24 | 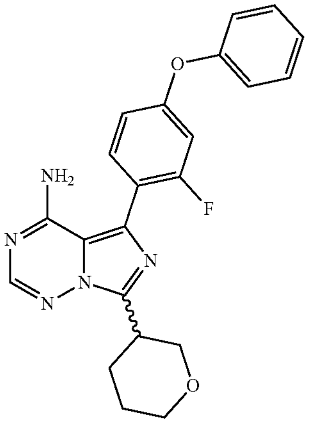 Trans isomer 1 5-(2-fluoro-4-phenoxyphenyl)-7-(tetrahydro-2H-pyran-4-yl)imidazo[5,1-f][1,2,4]triazin-4-amine |

TABLE 1-continued

| Cpd. No. | Compound Structure and Name |
|---|---|
| 25 | 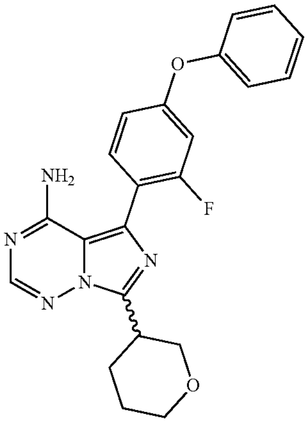 Trans isomer 2 5-(2-fluoro-4-phenoxphenyl)-7-(tetrahydro-2H-pyran-3-yl)imidazo[5,1-f][1,2,4]triazin-4-amine |
| 26 | 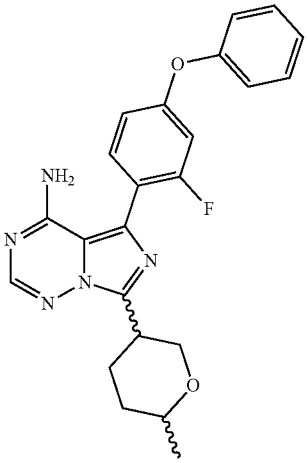 Trans isomer 1 5-(2-fluoro-4-phenoxyphenyl)-7-(6-methyl-tetrahydro-2H-pyran-3-yl)imidazo[5,1-f][1,2,4]triazin-4-amine |

TABLE 1-continued
| Compounds of the Invention | |
|---|---|
| Cpd. No. | Compound Structure and Name |
| 27 | 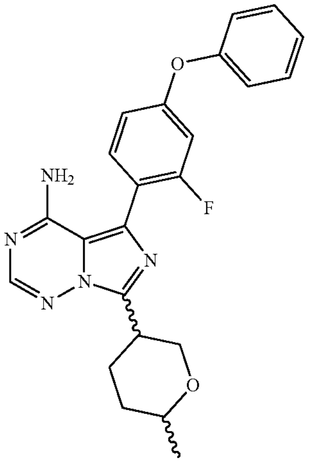 Trans isomer 2<br>5-(2-fluoro-4-phenoxyphenyl)-7-(6-methyl-tetrahydro-2H-pyran-3-yl)imidazo[5,1-f][1,2,4]triazin-4-amine |
Synthetic Methods
Compounds of the invention can be prepared according to the following two synthetic methods.
Method A
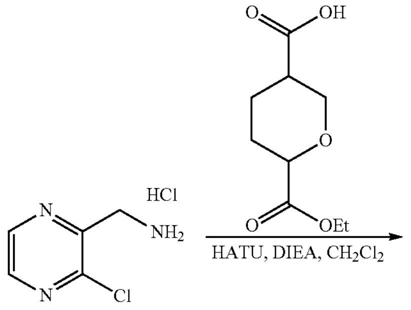
1A
-continued
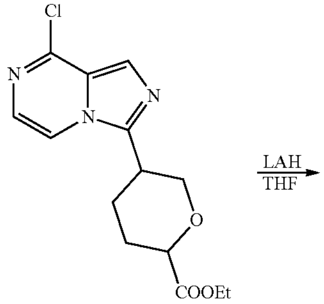
3A
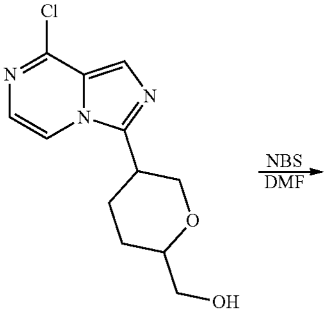
4A
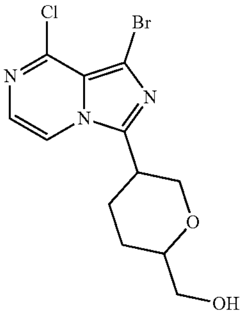
5A
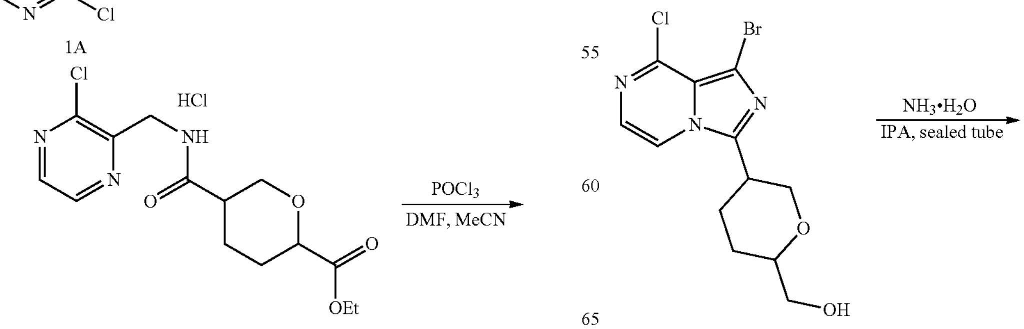
2A
5A -continued
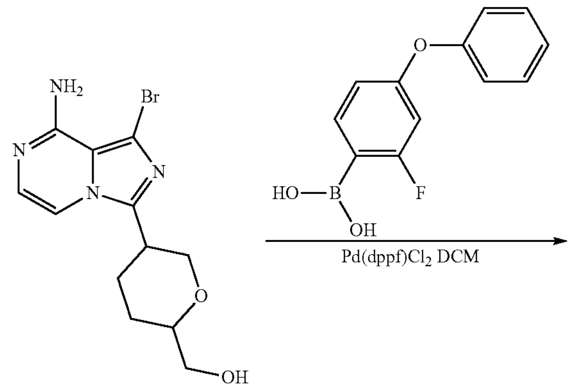
6A
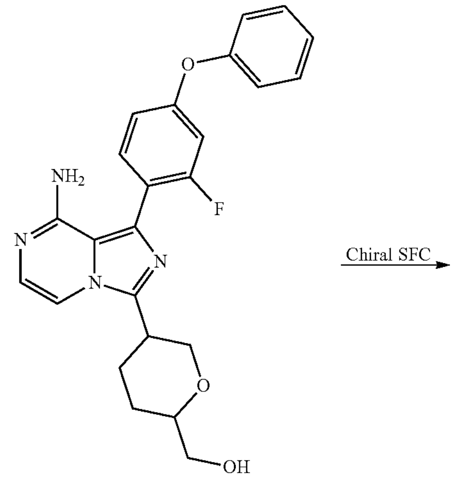
7A
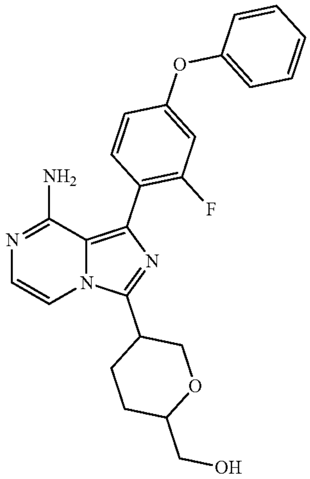
Trans isomer 1
Compound 2
-continued
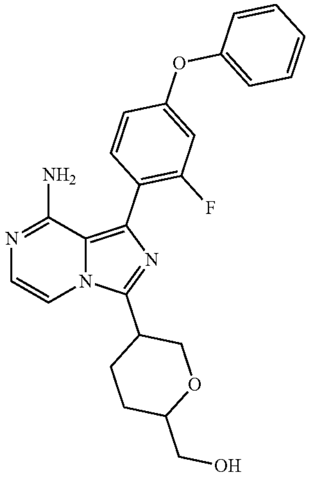
Trans isomer 2
Compound 3
Method B
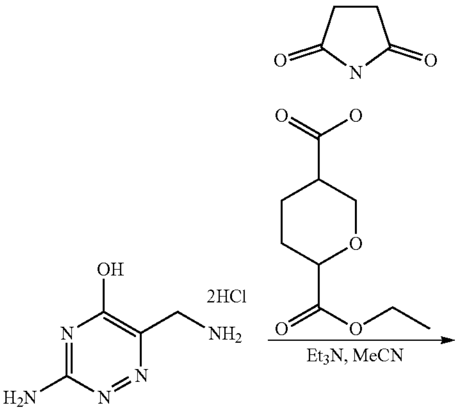
1B
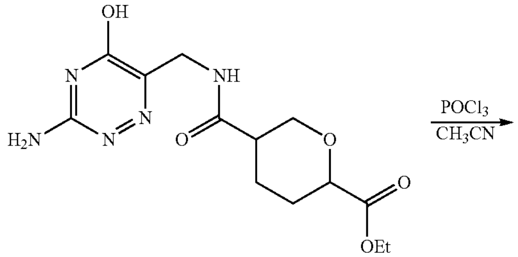
2B
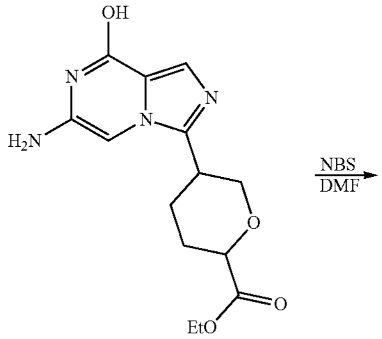
3B -continued
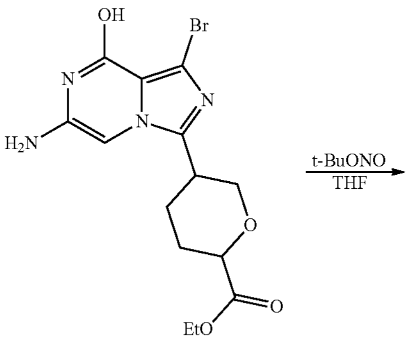
4B
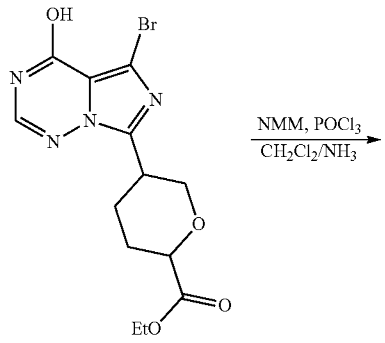
5B
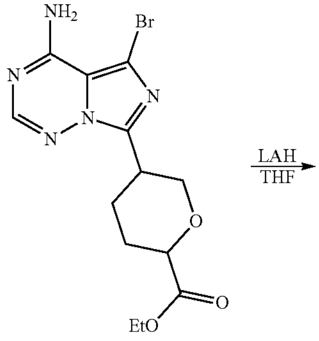
6B
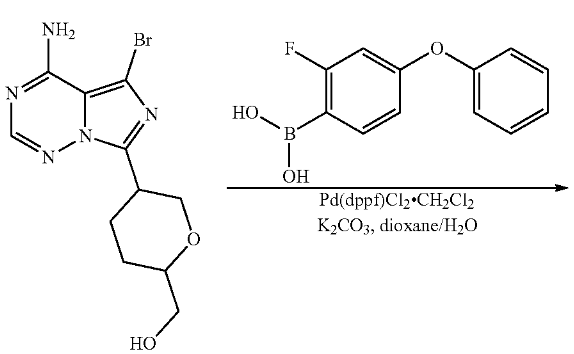
7B
-continued
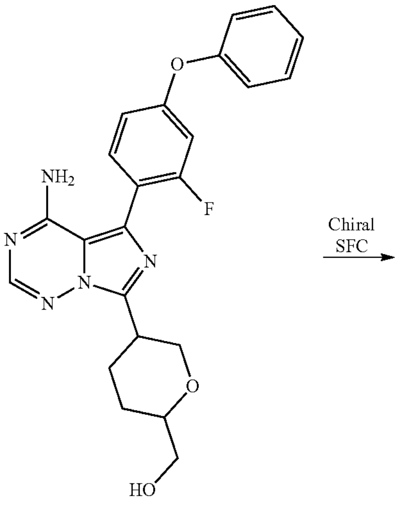
8B
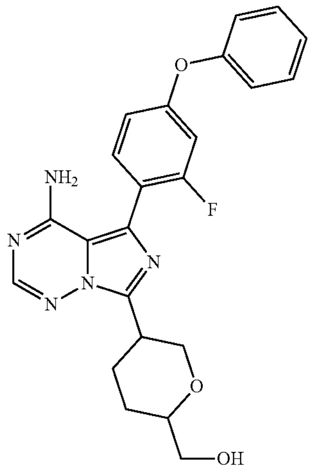
Cis isomer 1
Compound 8
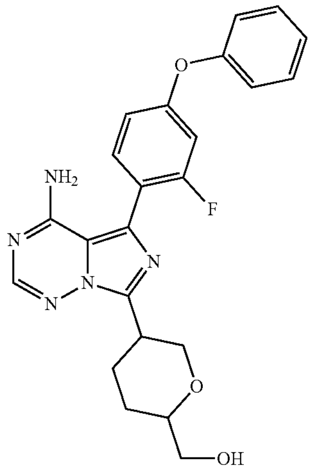
Cis isomer 2
Compound 9

-continued

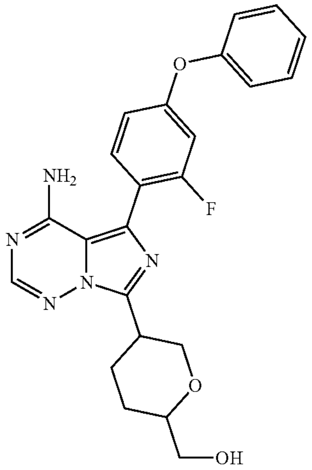

Trans isomer 1
Compound 10

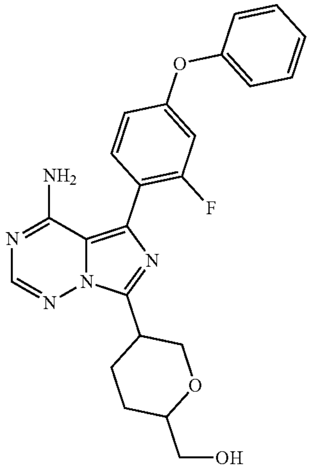

Trans isomer 2
Compound 11

Method A

Compound 2A: ethyl 5-(((3-chloropyrazin-2-yl) methyl)carbamoyl)tetrahydro-2H-pyran-2-carboxylate

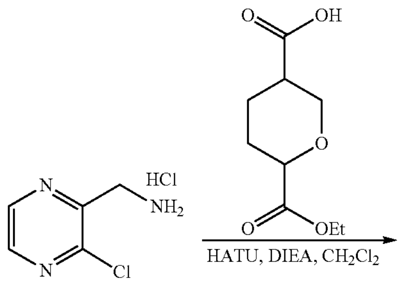

1A

-continued

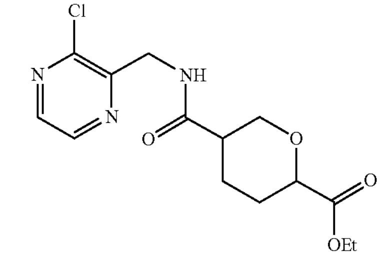

2A

To a mixture of 6-(ethoxycarbonyl)tetrahydro-2H-pyran-3-carboxylic acid (see WO2019001420A1) (5.90 g, 29.17 mmol) and compound 1A (5.25 g, 29.17 mmol) in dichloromethane (150 mL) was added HATU (16.64 g, 43.76 mmol) and DIEA (11.31 g, 87.51 mmol). The mixture was stirred at room temperature (18-22° C.) for 12 hours. The reaction was concentrated and diluted with water (100 mL), extracted with ethyl acetate (200 mL*3). The combined organic layers were washed with brine (200 mL*4), dried over anhydrous sodium sulfate, filtered and concentrated to give the crude product. The crude product was purified by column chromatography on silica gel (2.5-3.5% methanol in dichloromethane) to give the compound 2A (9.0 g, 94.0% yield) as yellow oil.

LCMS: tR=0.689 min in 5-95AB_1.5 min_220 &254_Shimadzu.lcm chromatography (Agilent Pursuit 5 C18 20*2.0 mm), MS (ESI) m/z=328.2 $[M+H]^+$ Compound 3A: ethyl 5-(8-chloroimidazo[1,5-c] pyrazin-3-yl)tetrahydro-2H-pyran-2-carboxylate

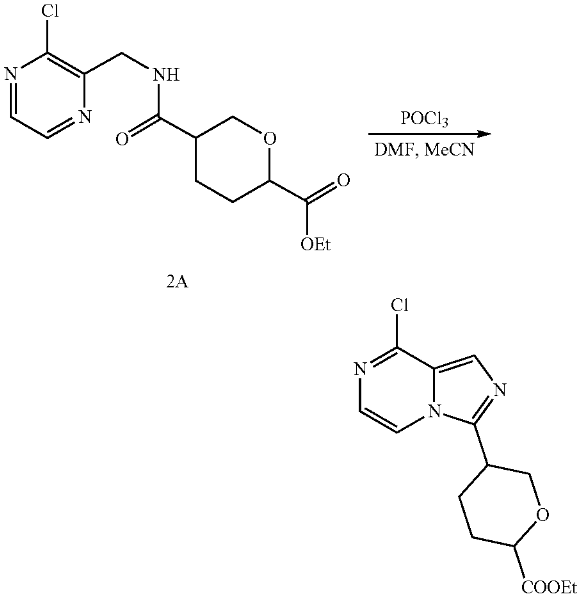

2A

3A

To a mixture of compound 2A (9.0 g, 27.46 mmol) and DMF (600 μL) in MeCN (150 mL) was added $POCl_3$ (21.05 g, 137.30 mmol). The mixture was stirred at 70° C. for 1 hour. The reaction was concentrated and washed with water (50 mL) and saturated $NaHCO_3$ (50 mL), extracted with ethyl acetate (100 mL*3). The combined organic layers were washed with brine (200 mL), dried over anhydrous sodium sulfate, filtered and concentrated to give the crude product. The crude product was purified by column chromatography on silica gel (52~62% ethyl acetate in petroleum ether) to give the compound 3A (3.5 g, 41.2% yield) as yellow oil.

LCMS: $t_R$=0.742 min in 5-95AB_1.5 min_220 &254_Shimadzu.lcm chromatography (Agilent Pursuit 5 C18 20*2.0 mm), MS (ESI) m/z=310.2 $[M+H]^+$ $^1$H NMR (400 MHz, $CDCl_3$): δ=7.80 (d, J=0.4 Hz, 1H), 7.70-7.64 (m, 1H), 7.37 (d, J=4.8 Hz, 0.3H), 7.35 (d, J=4.8 Hz, 0.7H), 4.44 (t, J=4.4 Hz, 0.7H), 4.30-4.25 (m, 2H), 4.23-4.14 (m, 1H), 4.00 (dd, J=3.2, 12.0 Hz, 1H), 3.79 (t, J=11.2 Hz, 0.4H), 3.42-3.19 (m, 1H), 2.47-2.37 (m, 0.8H), 2.29-2.06 (m, 3H), 1.91-1.77 (m, 0.4H), 1.35-1.31 (m, 3H).

Compound 4A: (5-(8-chloroimidazo[1,5-c]pyrazin-3-yl)tetrahydro-2H-pyran-2-yl)methanol

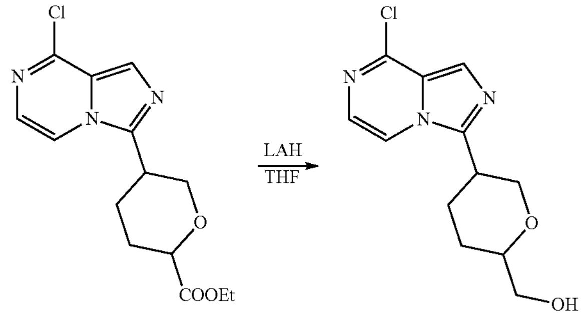

3A

4A

To a mixture of $LiAlH_4$ (860 mg, 22.60 mmol) in THF (20 mL) was added compound 3A (3.5 g, 11.30 mmol) in THF (20 mL) at 0° C. The mixture was stirred at 0° C. for 1 hour. The reaction was quenched with water (860 μL), 15% NaOH (860 μL), and water (2580 μL). The mixture was dried over anhydrous sodium sulfate and stirred at room temperature for 0.5 hour, filtered and concentrated to give compound 4A (2.7 g, 89.4% yield) as yellow solid.

LCMS: $t_R$=0.635 min in 5-95AB_1.5 min_220 &254_Shimadzu.lcm chromatography (Agilent Pursuit 5 C18 20*2.0 mm), MS (ESI) m/z=267.8 $[M+H]^+$ Compound 5A: (5-(1-bromo-8-chloroimidazo[1,5-a]pyrazin-3-yl)tetrahydro-2H-pyran-2-yl)methanol

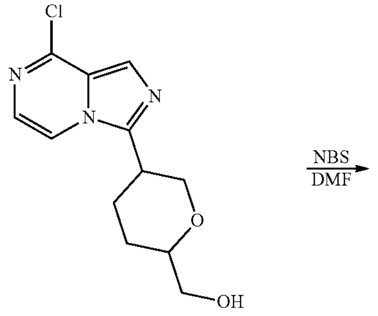

4A

-continued

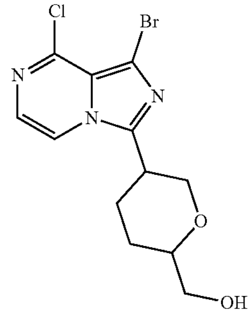

5A

To a mixture of compound 4A (2.7 g, 10.11 mmol) in MeCN (100 mL) was added NBS (2.34 g, 13.14 mmol). The mixture was stirred at room temperature (16-20° C.) for 1 hour. The reaction was concentrated to give the crude product which was purified by column chromatography on silica gel (2.2% methanol in dichloromethane) to give compound 5A (2.5 g, 71.63% yield) as yellow solid.

LCMS: $t_R$=0.717 min in 5-95AB_1.5 min_220 &254_Shimadzu.lcm chromatography (Agilent Pursuit 5 C18 20*2.0 mm), MS (ESI) m/z=347.8 $[M+H]^+$ Compound 6A: (5-(8-amino-1-bromoimidazo[1,5-a]pyrazin-3-yl)tetrahydro-2H-pyran-2-yl)methanol

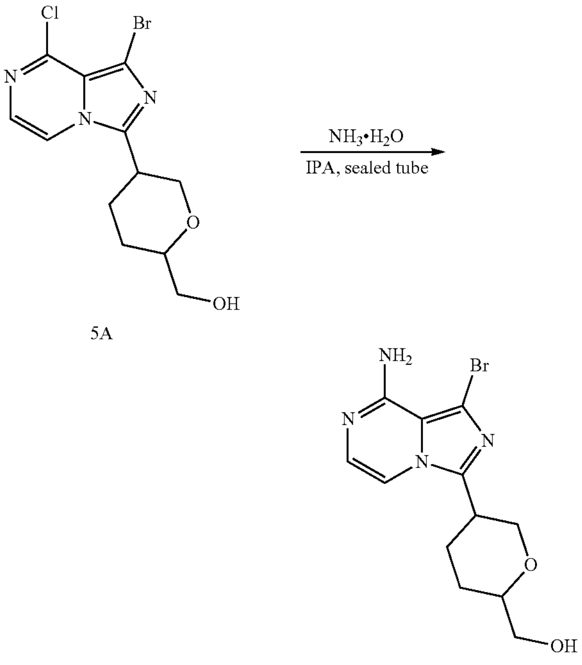

6A

To a mixture of compound 5A (2.5 g, 7.21 mmol) in IPA (15 mL) was added $NH_3 \cdot H_2O$ (15 mL). The mixture was stirred at 100° C. for 12 hours in a 100 mL sealed tube. The reaction was concentrated to give compound 6A (2.4 g, 98.0% purity) as yellow oil.

LCMS: $t_R$=0.436 min in 10-80AB_3 min_220 &254_Shimadzu.lcm chromatography (Xtimate C18 2.1*30 mm), MS (ESI) m/z=327.1 $[M+H]^+$ Compound 7A: (5-(8-amino-1-(2-fluoro-4-phenoxyphenyl)imidazo[1,5-a]pyrazin-3-yl)tetrahydro-2H-pyran-2-yl)methanol

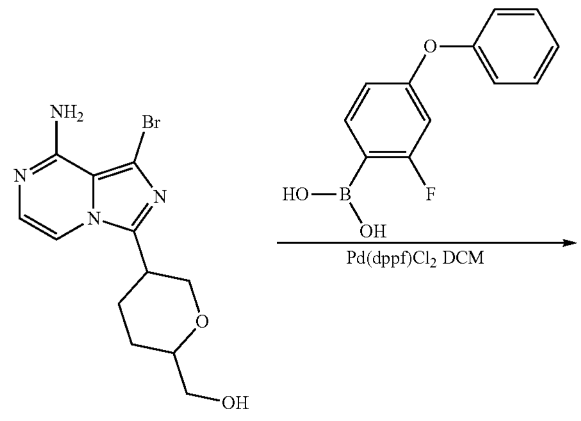

6A

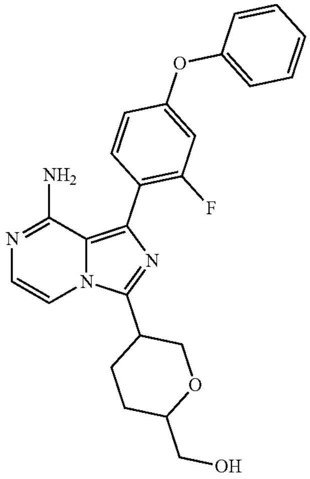

7A

To a mixture of compound 6A (500 mg, 1.31 mmol, 97.99% purity) and (2-fluoro-4-phenoxyphenyl)boronic acid (450 mg, 1.95 mmol) in 1,4-dioxane (15 mL)/$H_2O$ (5 mL) was added Pd(dppf)$Cl_2$·$CH_2Cl_2$ (32 mg, 0.04 mmol) and $K_2CO_3$ (375 mg, 2.62 mmol) under nitrogen. The mixture was stirred at 100° C. for 12 hours under nitrogen. The reaction was diluted with water (20 mL), extracted with ethyl acetate (50 mL*3). The combined organic layers were washed with brine (100 mL), dried over anhydrous sodium sulfate, filtered and concentrated to give the crude product. The crude product was purified by column chromatography on silica gel (2.2% methanol in dichloromethane) to give compound 7A (a mixture of cis/trans racemate) (150 mg, 26.4% yield) as yellow solid.

LCMS: $t_R$=0.723 min in 5-95AB_1.5 min_220 &254_Shimadzu.Icm chromatography (Agilent Pursuit 5 C18 20*2.0 mm), MS (ESI) m/z=435.1 $[M+H]^+$ 2-fluoro-4-phenoxyphenyl)boronic acid

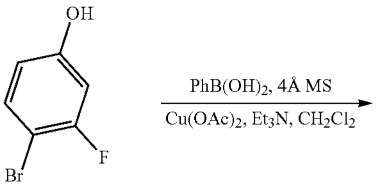

1a

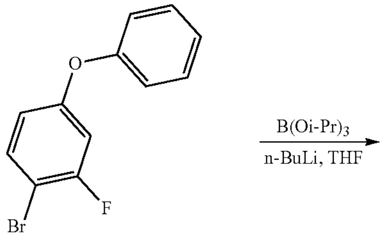

2a

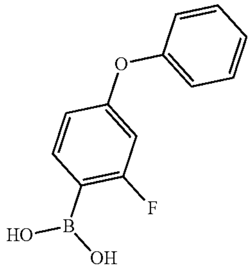

A mixture of compound 1a (10 g, 52.35 mmol) in $CH_2Cl_2$ (480 mL), PhB(OH)2 (12.8 g, 104.71 mmol), $Cu(OAc)_2$ (9.5 g, 52.35 mmol), $NEt_3$ (21 mL, 151.05 mmol) and 4 Å Ms (5 g) were added at room temperature (25-30° C.). The mixture was stirred at room temperature (25-30° C.) for 16 hours under air. The mixture was filtered through a Celite Pad. The filtrate was concentrated in vacuum to give the crude, which was purified by column chromatography on silica gel (petroleum ether) to obtain compound 2a (11.3 g, 80.8% yield) as colorless oil.

$^1H$ NMR (400 MHz, $CDCl_3$): δ=7.47 (t, J=8.4 Hz, 1H), 7.42-7.36 (m, 2H), 7.19 (t, J=8.4 Hz, 1H), 7.05 (d, J=8.0 Hz, 2H), 6.78 (dd, J=10.0, 2.8 Hz, 1H), 6.71 (dd, J=8.8, 2.0 Hz, 1H).

To a solution of compound 2a (11.3 g, 42.30 mmol) in THF (150 mL) at −65° C., n-BuLi (19 mL, 46.53 mmol, 2.5 N in n-hexane) was added at −65° C. The mixture was stirred at −65° C. for 0.5 hour. Then the $B(Oi\text{-}Pr)_3$ (9.5 g, 50.76 mmol) was added at −65° C. The mixture was stirred at −65° C. for 2 hours. The mixture was quenched with saturated ammonium chloride solution (50 mL), extracted with ethyl acetate (50 mL*3), washed with brine (100 mL*2). The combined organic layer was dried over anhydrous sodium sulfate, filtered and concentrated to afford the crude, which was triturated from petroleum ether (100 mL), filtered and the filtered cake was concentrated to give 2-fluoro-4-phenoxyphenyl)boronic acid (4.3 g) as yellow oil. The filtrate was concentrated and purified by column chromatography on silica gel (0~20% ethyl acetate in petroleum ether) to afford 2-fluoro-4-phenoxyphenyl)boronic acid (3 g) as yellow oil.

$^1H$ NMR (400 MHz, DMSO-d6): δ=8.10 (s, 2H), 7.58 (t, J=8.0 Hz, 1H), 7.47-7.41 (m, 2H), 7.22 (t, J=7.6 Hz, 1H), 7.09 (d, J=7.6 Hz, 2H), 6.78-6.68 (m, 2H).

Trans isomer 1, Compound 2: Trans-(5-(8-amino-1-(2-fluoro-4-phenoxyphenyl)imidazo[1,5-a]pyrazin-3-yl)tetrahydro-2H-pyran-2-yl)methanol Trans isomer 2, Compound 3: Trans-(5-(8-amino-1-(2-fluoro-4-phenoxyphenyl)imidazo[1,5-a]pyrazin-3-yl)tetrahydro-2H-pyran-2-yl)methanol

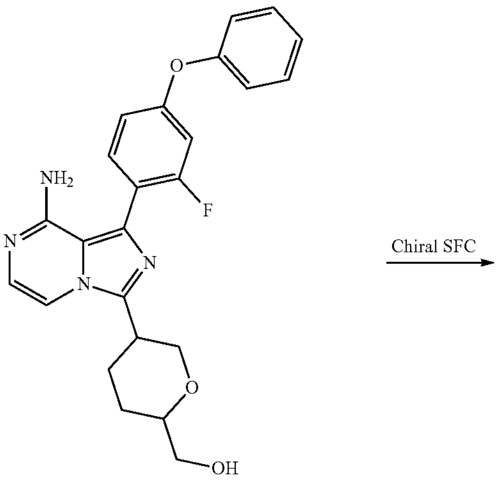

7A

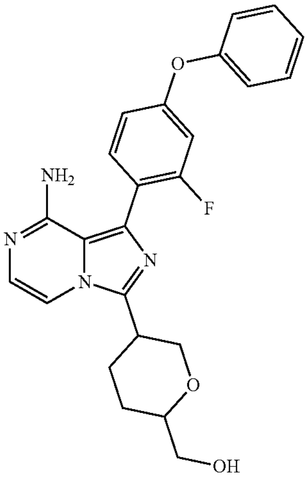

Trans isomer 1
Compound 2

-continued

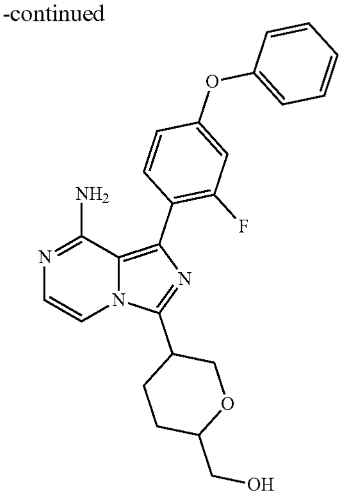

Trans isomer 2
Compound 3

The mixture 7A (150 mg, 0.35 mmol) was purified by chiral SFC (Column: DAICEL CHIRALPAK AD-H) (250 mm*30 mm, 10 μm), Condition: 0.1% $NH_3 \cdot H_2O$ in EtOH, 40%, Flow rate 80 mL/min). Fractions containing the desired compounds were concentrated, diluted with $H_2O$ (10 mL) and $CH_3CN$ (10 mL), lyophilized to give compound 2 (34.8 mg, 23.2% yield) as white solid and compound 3 (29.4 mg, 19.6%) as white solid. The two cis enantiomers were not collected.

The Spectra of Compound 2:

LCMS $t_R$=2.037 min in 10-80AB_7 min_220 &254_Shimadzu.lcm chromatography (Xtimate C18 2.1*30 mm), MS (ESI) m/z=435.3 $[M+H]^+$.

HPLC $t_R$=3.03 min in 10-80AB_8 min.met (HPLC-BJ Ultimate 3.0*50 mm 3 μm).

SFC $t_R$=6.119 min, optical purity: 96.3%. Method Comments: Column: ChiralPak AD-3 150×4.6 mm I.D., 3 μm, Mobile phase: A: $CO_2$ B: Ethanol (0.05% DEAL Gradient: from 5% to 40% of B in 5.5 min and hold 40% for 3 min, then 5% of B for 1.5 min, Flow rate: 2.5 mL/min, Column temp.: 40° C., Back pressure: 100 bar.

$^1H$ NMR (400 MHz, $CD_3OD$) δ=7.63 (d, J=5.2 Hz, 1H), 7.54-7.36 (m, 3H), 7.27-7.18 (m, 1H), 7.14 (dd, J=8.8, 0.8 Hz, 2H), 7.02 (d, J=4.8 Hz, 1H), 6.98-6.82 (m, 2H), 4.23-4.07 (m, 1H), 3.75 (t, J=11.2 Hz, 1H), 3.62-3.51 (m, 3H), 3.46-3.36 (m, 1H), 2.25-2.15 (m, 1H), 2.13-1.96 (m, 1H), 1.79 (d, J=13.6 Hz, 1H), 1.66-1.49 (m, 1H).

$^{19}F$ NMR ($CD_3OD$) δ=−112.240

The Spectra of Compound 3:

LCMS $t_R$=2.030 min in 10-80AB_7 min_220 &254_Shimadzu.lcm chromatography (Xtimate C18 2.1*30 mm), MS (ESI) m/z=435.3 $[M+H]^+$.

HPLC $t_R$=3.02 min in 10-80AB_8 min.met (HPLC-BJ Ultimate 3.0*50 mm 3 μm).

SFC $t_R$=7.334, optical purity: 92.7%. Method Comments: Column: ChiralPak AD-3 150×4.6 mm I.D., 3 μm, Mobile phase: A: $CO_2$ B: Ethanol (0.05% DEAL Gradient: from 5% to 40% of B in 5.5 min and hold 40% for 3 min, then 5% of B for 1.5 min, Flow rate: 2.5 mL/min, Column temp.: 40° C., Back pressure: 100 bar.

$^1H$ NMR (400 MHz, $CD_3OD$) δ=7.65 (d, J=5.2 Hz, 1H), 7.52-7.37 (m, 3H), 7.29-7.21 (m, 1H), 7.20-7.11 (m, 2H), 7.04 (d, J=4.8 Hz, 1H), 6.99-6.84 (m, 2H), 4.24-4.13 (m, 1H), 3.77 (t, J=11.2 Hz, 1H), 3.62-3.51 (m, 3H), 3.48-3.77 (m, 1H), 2.31-2.17 (m, 1H), 2.15-2.01 (m, 1H), 1.91-1.74 (m, 1H), 1.69-1.51 (m, 1H).

$^{19}F$ NMR (400 MHz, $CD_3OD$) δ=−112.258.

The following compounds were synthesized according to method A:

| Cpd No. | LC-MS method | LC-MS retention time ($t_R$, min) | HPLC method | HPLC retention time ($t_R$, min) |
|---|---|---|---|---|
| 1 | A | 2.092 | A | 3.01 |
| 2 | A | 2.037 | A | 3.03 |
| 3 | A | 2.030 | A | 3.02 |
| 4 | A | 2.125 | A | 3.16 |
| 5 | A | 2.107 | A | 3.16 |
| 6 | A | 2.142 | A | 3.17 |
| 7 | A | 2.137 | A | 3.17 |

| Cpd No. | Analytical SFC method | SFC retention time ($t_R$, min) | HNMR |
|---|---|---|---|
| 1 | Not performed | N.A. | $^1$H NMR (400 MHz, $CD_3OD$): δ = 7.64-7.57 (m, 3H), 7.45-7.38 (m, 2H), 7.20-7.07 (m, 5H), 7.02 (d, J = 5.2 Hz, 1H), 4.18-4.11 (m, 1H), 3.77 (t, J = 11.2 Hz, 1H), 3.61-3.51 (m, 3H), 3.45-3.37 (m, 1H), 2.25-2.16 (m, 1H), 2.13-2.00 (m, 1H), 1.84-1.74 (m, 1H), 1.67-1.51 (m, 1H). |
| 2 | A | 6.119 | $^1$H NMR (400 MHz, $CD_3OD$) δ = 7.63 (d, J = 5.2 Hz, 1H), 7.54-7.36 (m, 3H), 7.27-7.18 (m, 1H), 7.14 (dd, J = 8.8, 0.8 Hz, 2H), 7.02 (d, J = 4.8 Hz, 1H), 6.98-6.82 (m, 2H), 4.23-4.07 (m, 1H), 3.75 (t, J = 11.2 Hz, 1H), 3.62-3.51 (m, 3H), 3.46-3.36 (m, 1H), 2.25-2.15 (m, 1H), 2.13-1.96 (m, 1H), 1.79 (d, J = 13.6 Hz, 1H), 1.66-1.49 (m, 1H). |
| 3 | A | 7.344 | $^1$H NMR (400 MHz, $CD_3OD$) δ =7.65 (d, J = 5.2 Hz, 1H), 7.52-7.37 (m, 3H), 7.29-7.21 (m, 1H), 7.20-7.11 (m, 2H), 7.04 (d, J = 4.8 Hz, 1H), 6.99-6.84 (m, 2H), 4.24-4.13 (m, 1H), 3.77 (t, J = 11.2 Hz, 1H), 3.62-3.51 (m, 3H), 3.48-3.77 (m, 1H), 2.31-2.17 (m, 1H), 2.15-2.01 (m, 1H), 1.91-1.74 (m, 1H), 1.69-1.51 (m, 1H). |
| 4 | A | 5.622 | $^1$HNMR (400 MHz, $CD_3OD$) δ = 7.66 (d, J = 5.2 Hz, 1H), 7.47-7.39 (m, 2H), 7.30-7.17 (m, 2H), 7.16-7.09 (m, 2H), 7.06 (d, J = 5.2 Hz, 1H), 7.00-6.91 (m, 1H), 4.27-4.04 (m, 1H), 3.75 (t, J = 11.2 Hz, 1H), 3.62-3.49 (m, 3H), 3.48-3.36 (m, 1H), 2.28-2.17 (m, 1H), 2.14-1.98 (m, 1H), 1.86-1.74 (m, 1H), 1.69-1.49 (m, 1H). $^{19}$FNMR (400 MHz, $CD_3OD$) δ = −137.837, −156.987. |
| 5 | A | 6.448 | $^1$HNMR (400 MHz, $CD_3OD$) δ = 7.66 (d, J = 5.2 Hz, 1H), 7.47-7.36 (m, 2H), 7.30-7.16 (m, 2H), 7.13 (d, J = 8.0 Hz, 2H), 7.06 (d, J = 5.2 Hz, 1H), 7.01-6.88 (m, 1H), 4.25-4.07 (m, 1H), 3.75 (t, J = 11.2 Hz, 1H), 3.62-3.51 (m, 3H), 3.47-3.39 (m, 1H), 2.32-2.15 (m, 1H), 2.13-1.98 (m, 1H), 1.84-1.74 (m, 1H), 1.70-1.47 (m, 1H). $^{19}$FNMR (400 MHz, $CD_3OD$) δ = −137.784, −156.934. |
| 6 | A | 1.906 | $^1$HNMR (400 MHz, $CD_3OD$) δ = 7.66-7.57 (m, 3H), 7.26-7.08 (m, 4H), 7.05-6.98 (m, 2H), 4.20-4.07 (m, 1H), 3.77 (t, J = 11.2 Hz, 1H), 3.62-3.51 (m, 3H), 3.46-3.36 (m, 1H), 2.25-2.15 (m, 1H), 2.12-2.00 (m, 1H), 1.80 (br d, J = 13.6 Hz, 1H), 1.66-1.51 (m, 1H). $^{19}$FNMR (400 MHz, $CD_3OD$) δ = −138.700, −157.737. |
| 7 | A | 2.217 | $^1$HNMR (400 MHz, $CD_3OD$) δ = 7.70-7.57 (m, 3H), 7.26-7.08 (m, 4H), 7.05-6.98 (m, 2H), 4.20-4.07 (m, 1H), 3.77 (t, J = 11.2 Hz, 1H), 3.62-3.51 (m, 3H), 3.46-3.36 (m, 1H), 2.25-2.15 (m, 1H), 2.12-2.00 (m, 1H), 1.80 (br d, J= 13.8 Hz, 1H), 1.66-1.51 (m, 1H). $^{19}$FNMR (400 MHz, $CD_3OD$) δ = −138.655, −157.692. |

Method B

Compound 28: ethyl 5-(((3-amino-5-hydroxy-1,2,4-triazin-6-yl)methyl)carbamoyl)tetrahydro-2H-pyran-2-carboxylate

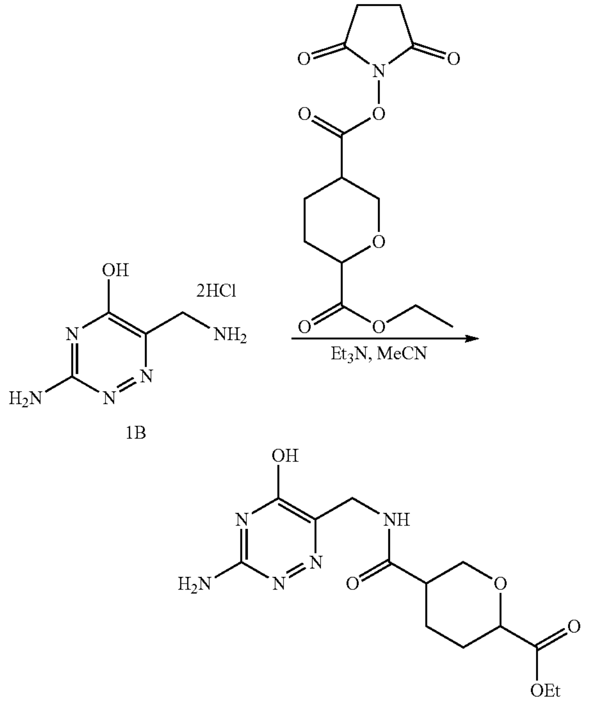

1B

2B

To a mixture of 5-(2,5-dioxopyrrolidin-1-yl) 2-ethyl tetrahydro-2H-pyran-2,5-dicarboxylate (20 g crude, 60.88 mmol) in acetonitrile (30 mL), compound 1B (13 g, 60.88 mmol) and triethylamine (25 mL, 182.6 mmol) were added. The mixture was stirred at 50° C. for 16 hours. The mixture was concentrated to afford compound 2B (35 g crude) as a brown solid.

LCMS: $t_R$=0.582 min in 5-95AB_1.5 min_220 &254_Shimadzu.lcm chromatography (Merck RP18 25-3 mm), MS (ESI) m/z=325.9 $[M+H]^+$ 5-(2,5-dioxopyrrolidin-1-yl) 2-ethyl tetrahydro-2H-pyran-2,5-dicarboxylate

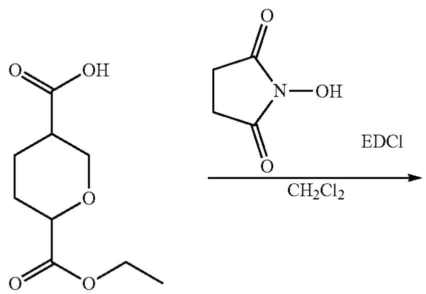

-continued

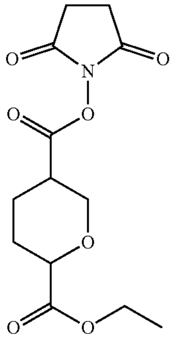

To a solution of 6-(ethoxycarbonyl)tetrahydro-2H-pyran-3-carboxylic acid (1.4 g, 6.92 mmol) in $CH_2Cl_2$ (30 mL), 1-hydroxypyrrolidine-2,5-dione (877 mg, 7.61 mmol) and EDCI (1.6 g, 8.30 mmol) were added. The mixture was stirred at 22-26° C. for 1.5 hours. The mixture was diluted with dichloromethane (30 mL), washed with brine (50 mL×3). The organic layer was dried over anhydrous sodium sulfate, filtered and concentrated to afford 5-(2,5-dioxopyrrolidin-1-yl) 2-ethyl tetrahydro-2H-pyran-2,5-dicarboxylate as colorless oil which is used directly.

Compound 38: ethyl 5-(2-amino-4-hydroxyimidazo[5,1-f][1,2,4]triazin-7-yl)tetrahydro-2H-pyran-2-carboxylate

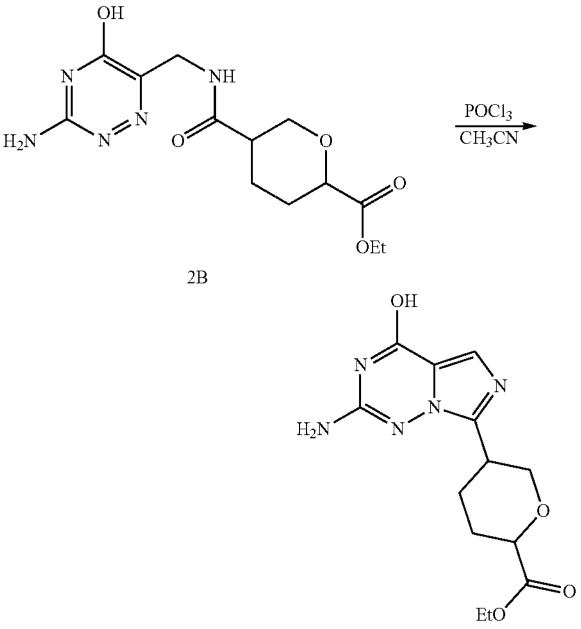

2B

3B

To a solution of compound 2B (35 g crude, 60.88 mmol) in acetonitrile (300 mL), phosphorus oxychloride (23 mL, 243.52 mmol) was added. Then the mixture was stirred at 70° C. for 16 hours. The mixture was concentrated, the residue was diluted with dichloromethane (150 mL), poured into cooled is saturated solution of sodium bicarbonate (300 mL) to pH=8, extracted with dichloromethane/methanol (10:1, 200 mL*4), followed by IPA/$CHCl_3$ (150 mL*4). The combined organic layer was dried over anhydrous sodium sulfate, filtered and concentrated to afford compound 3B (45 g crude) as black oil.

LCMS: $t_R$=0.13 min in 5-95AB_1.5 min_220 &254_Shimadzu.lcm chromatography (Merck RP18 25-3 mm), MS (ESI) m/z=308.0 $[M+H]^+$ Compound 48: ethyl 5-(2-amino-5-bromo-4-hydroxyimidazo[5,1-f][1,2,4]triazin-7-yl)tetrahydro-2H-pyran-2-carboxylate

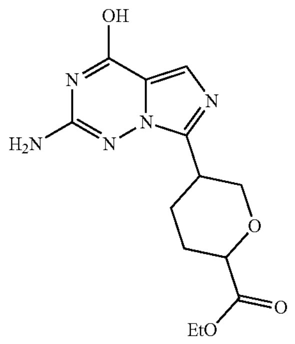

3B

NBS
DMF

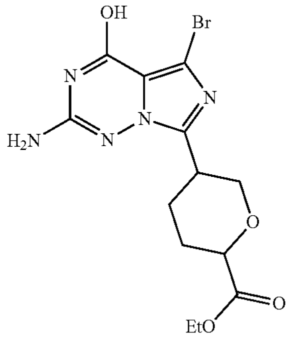

4B

To a solution of compound 3B (45 g crude, 60.88 mmol) in N,N-dimethylformamide (200 mL), NBS (11.8 g, 66.96 mmol) was added. The mixture was stirred at room temperature (16-21° C.) for 0.5 hour. The mixture was poured into water (300 mL), extracted with ethyl acetate (300 mL*4), washed with brine (500 mL*4). The combined organic layer was dried over anhydrous sodium sulfate, filtered and concentrated to afford compound 4B (19 g crude) as black oil.

LCMS: $t_R$=0.602 min in 5-95AB_1min_220 &254_Agilent chromatography (Agilent Poroshell 120 EC-C18 2.7 µm 3.0*30 mm), MS (ESI) m/z=388.0 $[M+H+2]^+$ (Bromide isotope).

Compound 5B: ethyl 5-(5-bromo-4-hydroxyimidazo[5,1-f][1,2,4]triazin-7-yl)tetrahydro-2H-pyran-2-carboxylate

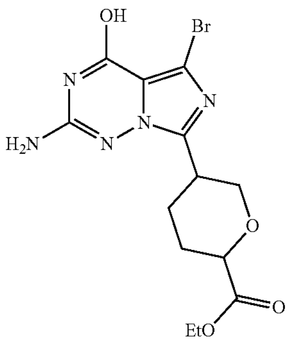

4B t-BuONO
THF

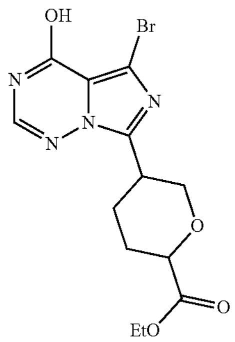

5B

To a solution of compound 4B (19 g impure, 49.19 mmol) in tetrahydrofuran (300 mL), tert-butyl nitrite (12 mL, 98.39 mmol) was added at 0-5° C., and the mixture was stirred at room temperature (16-21° C.) for 16 hours. The mixture was combined with another batch (7.2 g crude of compound 4B), and concentrated afford the crude material which was purified by column chromatography on silica gel (0~60% ethyl acetate in petroleum ether) to afford compound 5B (14.3 g, 44% yield for 5 steps) as a yellow solid.

LCMS: $t_R$=0.753 min in 5-95AB_1.5 min_220 &254_Shimadzu.lcm chromatography (Agilent Pursuit 5 C18 20*2.0 mm), MS (ESI) m/z=370.9 $[M+H]^+$ $^1$H NMR (400 MHz, $CD_3OD$): δ=7.74 (s, 0.3H), 7.72 (s, 0.5H), 4.37 (t, J=4.8 Hz, 0.7H), 4.29-4.16 (m, 3H), 4.12 (dd, J=11.6, 2.0 Hz, 0.3H), 3.92 (dd, J=11.6, 4.0 Hz, 0.7H), 3.70 (t, J=11.2 Hz, 0.4H), 3.57-3.45 (m, 1H), 2.35-1.92 (m, 4H), 1.33-1.27 (m, 3H).

Compound 6B: ethyl 5-(4-amino-5-bromoimidazo[5,1-f][1,2,4]triazin-7-yl)tetrahydro-2H-pyran carboxylate

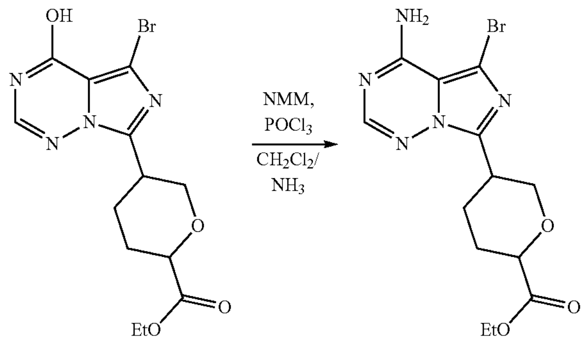

5B 6B

To a solution of 1,2,4-triazole (28 g, 404.1 mmol) in acetonitrile (200 mL), $POCl_3$ (12.5 mL, 134.7 mol) was added below 10° C. followed by trimethylamine (56 mL, 404.1 mmol). The mixture was stirred for 20 min at 10° C., compound 5B (5 g, 13.47 mmol) was added, and the reaction mixture was stirred for 1.5 hours at 90° C. The mixture was cooled to 10° C., ammonia (30 mL, 28%) was added keeping the temperature below 20° C. and stirred for 0.5 hour at 10° C. Another batch with same scale was carried out. The mixtures were combined and diluted with water (200 mL) and extracted with ethyl acetate (500 mL*3), washed with brine (500 mL*3), dried over anhydrous sodium sulfate, filtered and concentrated in vacuo, which was purified by column chromatography on silica gel (2~4% methanol in dichloromethane) to afford compound 6B (9 g, 90% yield) as a yellow solid.

LCMS: $t_R$=0.614 min in \5-95AB_1 min_220 &254_Agilent chromatography (Agilent Poroshell 120 EC-C18 2.7 μm 3.0*30 mm), MS (ESI) m/z=372.0 [M+H+2]+(Bromide isotope).

$^1$H NMR (400 MHz, $CD_3OD$): δ=7.81 (s, 0.3H), 7.79 (s, 0.6H), 4.36 (t, J=5.2 Hz, 0.6H), 4.29-4.19 (m, 3H), 4.12 (dd, J=11.6, 2.0 Hz, 0.3H), 3.93 (dd, J=11.6, 4.0 Hz, 0.7H), 3.71 (t, J=11.2 Hz, 0.3H), 3.63-3.48 (m, 1H), 2.35-2.20 (m, 1H), 2.17-1.94 (m, 2.7H), 1.79-1.68 (m, 0.3H), 1.34-1.26 (m, 3H).

Compound 7B: (5-(4-amino-5-bromoimidazo[5,1-f][1,2,4]triazin-7-yl)tetrahydro-2H-pyran-2-yl)methanol

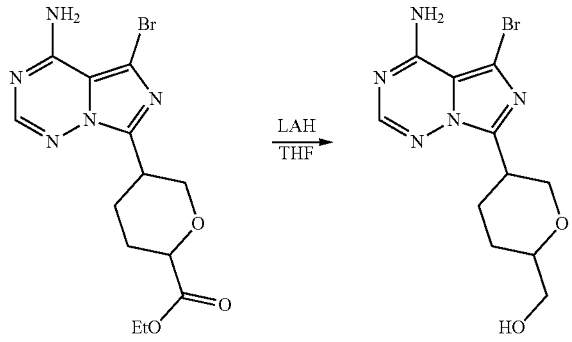

6B 7B

To a solution of compound 6B (6.1 g, 16.48 mmol) in tetrahydrofuran (120 mL) cooled at 0-5° C., $LiAH_4$ (1.20 g, 32.95 mmol) was added keeping the temperature below 10° C. The mixture was stirred at 0-10° C. for 1.5 hours. To the mixture was added 25 g of $Na_2SO_4 \cdot 10H_2O$ at 0-5° C. and stirred for 2 hours and filtered. The filter cake was suspended with dichloromethane/methanol (100 mL of 10:1 mixture) twice and filtered. The combined filtration was concentrated in vacuo, the residue was purified by column chromatography on silica (0~10% methanol in dichloromethane) to afford compound 7B (3.9 g, 72% yield) as white solid and 0.6 g of debromination by product as yellow solid.

LCMS: $t_R$=1.958 and 2.016 min in \0-60AB_7 min_220 &254_Shimadzu.lcm chromatography (Xtimate C18 2.1*30 mm, 3 μm), MS (ESI) m/z=328.1 $[M+H]^+$.

$^1$H NMR (400 MHz, Methanol_$d_4$): δ=7.80 (s, 0.3H), 7.78 (s, 0.6H), 4.47 (dt, J=10.0, 2.0 Hz, 0.6H), 4.20-4.13 (m, 0.3H), 3.84 (dd, J=11.6, 3.2 Hz, 0.6H), 3.64 (t, J=10.8 Hz, 0.4H), 3.60-3.38 (m, 4H), 2.45-2.36 (m, 0.6H), 2.22-2.13 (m, 0.3H), 2.09-1.96 (m, 1H), 1.93-1.73 (m, 1H), 1.62-1.45 (m, 1H).

Compound 8B: (5-(4-amino-5-(2-fluoro-4-phenoxyphenyl)imidazo[5,1-f][1,2,4]triazin-7-yl)tetrahydro-2H-pyran-2-yl)methanol

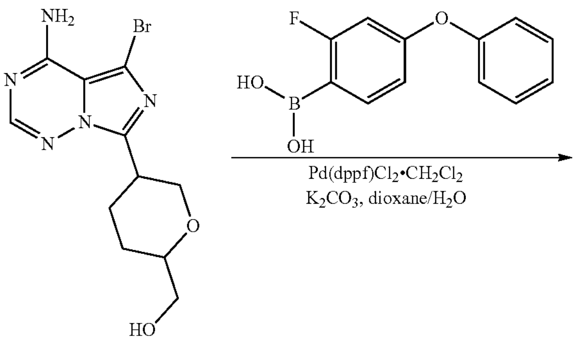

7B

-continued

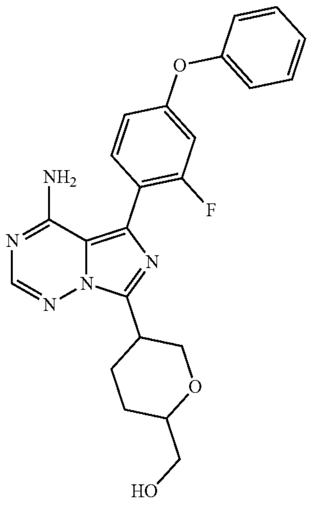 [SMILES: CC1CCC(c2nc(-c3ccc(Oc4ccccc4)cc3F)c3c(N)ncnn23)CO1]

8B

Compound 7B (106 mg, 0.457 mmol), Pd(dppf) $Cl_2CH_2Cl_2$ (25 mg, 0.0304 mmol) and potassium carbonate (84 mg, 0.608 mmol) were placed in a reaction tube and purged with nitrogen for 3 times, and (2-fluoro-4-phenoxy-phenyl)boronic acid (100 mg, 0.304 mmol) in 1,4-dioxane (3 mL) and water (1 mL) were added. The resulting mixture was stirred at 100° C. under nitrogen for 2 hours. The mixture was concentrated to obtain the crude, which was purified by column chromatography on silica gel (0~100% ethyl acetate in petroleum ether) to afford compound 8B (80 mg impure, a mixture of trans/cis racemates) as yellow oil.

LCMS: $t_R$=2.274 min & 2.340 min in 10-80AB_7 min_220 &254_Shimadzu.lcm chromatography (Xtimate C18 2.1*30 mm), MS (ESI) m/z=436.2 [M+H]+.

SFC: $t_R$=4.171 min, 4.286 min, 4.454 min and 5.581 min. Method: Column: Chiralcel OJ-3 150×4.6 mm I.D., 3 μm Mobile phase: A: $CO_2$ B: methanol Gradient: from 5% to 40% of B in 5 min and from 40% to 5% of B in 0.5 min, hold 5% of B for 1.5 min Flow rate: 2.5 mL/min, Column temp.: 35° C. ABPR: 1500 psi.

Cis Isomer 1, Compound 8: Cis-(5-(4-amino-5-(2-fluoro-4-phenoxyphenyl)imidazo[5,1-f][1,2,4]triazin yl)tetrahydro-2H-pyran-2-yl)methanol Cis Isomer 2, Compound 9: Cis-(5-(4-amino-5-(2-fluoro-4-phenoxyphenyl)imidazo[5,1-f][1,2,4]triazin yl)tetrahydro-2H-pyran-2-yl)methanol Trans Isomer 1, Compound 10: Trans-(5-(4-amino-5-(2-fluoro-4-phenoxyphenyl)imidazo[5,1-f][1,2,4]triazin-7-yl)tetrahydro-2H-pyran-2-yl)methanol Trans Isomer 2, Compound 11: Trans-(5-(4-amino-5-(2-fluoro-4-phenoxyphenyl)imidazo[5,1-f][1,2,4]triazin-7-yl)tetrahydro-2H-pyran-2-yl)methanol

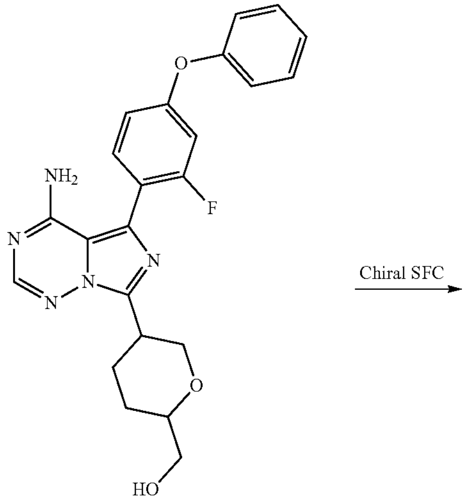

8B

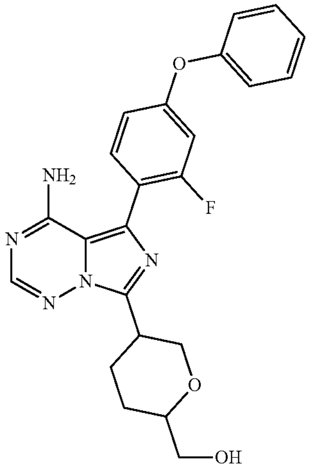

Cis isomer 1
Compound 8

-continued

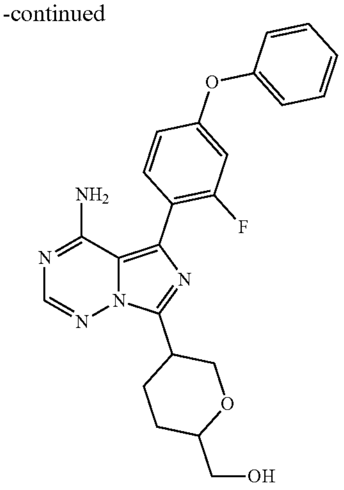

Cis isomer 2
Compound 9

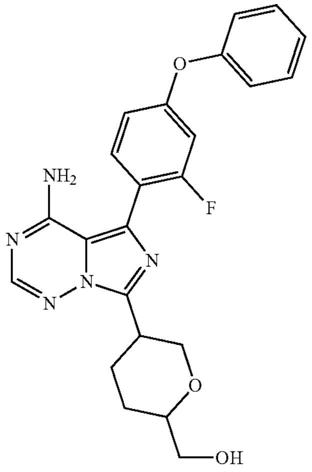

Trans isomer 1
Compound 10

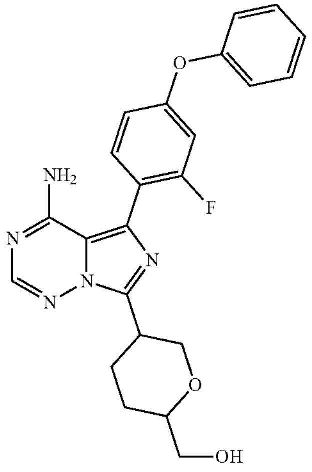

Trans isomer 2
Compound 11

The compound 8B (80 mg) was further separated by prep-SFC (Column: DAICEL CHIRALCEL OJ-H (250 mm*30 mm, 5 μm); Condition: 30% MeOH (0.1% $NH_3H_2O$) in $CO_2$; Flowrate: 60 mL/min) to afford 6.8 mg of impure compound 11 which was further purified by prep-HPLC (Column: Welch Xtimate C18 100*40 mm*3 μm, Condition: 25-55% (A: water (0.225% FA), B: $CH_3CN$), flow rate: 25 mL/min) to afford compound 11 (1.7 mg, 1% yield for 2 steps) as a white solid. After SFC, the mixture of others three peaks is (40 mg) was further purified by chiral SFC (Column: DAICEL CHIRALPAK IG (250 mm*30 mm, 10 μm); Condition: 55% MeOH (0.1% $NH_3H_2O$) in $CO_2$; Flowrate: 80 mL/min) to afford compound 8 (8.6 mg, 6.4% yield for 2 steps) as a white solid, compound 9 (6.7 mg, 5% yield for 2 steps) as a white solid and compound 10 (5.4 mg, 4% yield for 2 steps) as a white solid.

The Spectra of Compound 8:

LCMS: $t_R$=2.356 min in 10-80AB_7 min_220 &254_Shimadzu.lcm chromatography (Xtimate C18 2.1*30 mm), MS (ESI) m/z=436.2 $[M+H]^+$.

HPLC: $t_R$=3.00 min in 10-80CD_8 min.met.chromatography (XBridge Shield RP 18 2.1*50 mm 5 μm).

$^1H$ NMR (400 MHz, $CD_3OD$): δ=7.84 (s, 1H), 7.54 (t, J=8.4 Hz, 1H), 7.47-7.41 (m, 2H), 7.26-7.20 (m, 1H), 7.17-7.12 (m, 2H), 6.94 (dd, J=8.0, 2.0 Hz, 1H), 6.88 (dd, J=10.8, 2.4 Hz, 1H), 4.56-4.51 (m, 1H), 3.89 (dd, J=11.6, 3.6 Hz, 1H), 3.65-3.48 (m, 4H), 2.51-2.42 (m, 1H), 2.12-2.02 (m, 1H), 1.99-1.85 (m, 1H), 1.64-1.55 (m, 1H).

SFC: $t_R$=4.059 min, 99.94% optical purity.

Method: Column: Chiralcel OJ-3 150×4.6 mm I.D., 3 μm Mobile phase: A: $CO_2$ B: methanol (0.05% DEA) Gradient: from 5% to 40% of B in 5 min and from 40% to 5% of B in 0.5 min, hold 5% of B for 1.5 min Flow rate: 2.5 mL/min Column temp.: 35° C. ABPR: 1500 psi.

The Spectra of Compound 9:

LCMS: $t_R$=2.340 min in 10-80AB_7 min_220 &254_Shimadzu.lcm chromatography (Xtimate C18 2.1*30 mm), MS (ESI) m/z=436.3 $[M+H]^+$.

HPLC: $t_R$=2.99 min in 10-80CD_8 min.met.chromatography (XBridge Shield RP 18 2.1*50 mm 5 μm).

$^1H$ NMR (400 MHz, $CD_3OD$): δ=7.84 (s, 1H), 7.53 (t, J=8.4 Hz, 1H), 7.47-7.41 (m, 2H), 7.25-7.19 (m, 1H), 7.17-7.12 (m, 2H), 6.94 (dd, J=8.4, 2.0 Hz, 1H), 6.87 (dd, J=11.2, 2.4 Hz, 1H), 4.56-4.50 (m, 1H), 3.88 (dd, J=12.0, 3.6 Hz, 1H), 3.65-3.48 (m, 4H), 2.50-2.41 (m, 1H), 2.12-2.02 (m, 1H), 1.97-1.86 (m, 1H), 1.64-1.55 (m, 1H).

SFC: $t_R$=4.161 min, 100% optical purity.

Method: Column: Chiralcel OJ-3 150×4.6 mm I.D., 3 μm Mobile phase: A: $CO_2$ B: methanol (0.05% DEA) Gradient: from 5% to 40% of B in 5 min and from 40% to 5% of B in 0.5 min, hold 5% of B for 1.5 min Flow rate: 2.5 mL/min Column temp.: 35° C. ABPR: 1500 psi.

The Spectra of Compound 10:

LCMS: $t_R$=2.410 min in 10-80AB_7 min_220 &254_Shimadzu.lcm chromatography (Xtimate C18 2.1*30 mm), MS (ESI) m/z=436.3 $[M+H]^+$.

HPLC: $t_R$=2.98 min in 10-80CD_8 min.met.chromatography (XBridge Shield RP 18 2.1*50 mm 5 μm).

$^1H$ NMR (400 MHz, $CD_3OD$): δ=7.86 (s, 1H), 7.50 (t, J=8.4 Hz, 1H), 7.47-7.41 (m, 2H), 7.26-7.20 (m, 1H), 7.17-7.12 (m, 2H), 6.94 (dd, J=8.4, 2.4 Hz, 1H), 6.88 (dd, J=10.8, 2.4 Hz, 1H), 4.24-4.18 (m, 1H), 3.75 (t, J=11.2 Hz, 1H), 3.68-3.48 (m, 4H), 2.27-2.19 (m, 1H), 2.16-2.04 (m, 1H), 1.84-1.76 (m, 1H), 1.59-1.47 (m, 1H).

SFC: $t_R$=4.405 min, 99.83% optical purity.

Method: Column: Chiralcel OJ-3 150×4.6 mm I.D., 3 μm Mobile phase: A: $CO_2$ B: methanol (0.05% DEA) Gradient: from 5% to 40% of B in 5 min and from 40% to 5% of B in 0.5 min, hold 5% of B for 1.5 min Flow rate: 2.5 mL/min Column temp.: 35° C. ABPR: 1500 psi.

The Spectra of Compound 11:

LCMS: $t_R$=2.365 min in 10-80AB_7 min_220 &254_Shimadzu.lcm chromatography (Xtimate C18 2.1*30 mm), MS (ESI) m/z=436.2 $[M+H]^+$.

HPLC: $t_R$=3.05 min in 10-80CD_8 min.met.chromatography (XBridge Shield RP 18 2.1*50 mm 5 μm).

$^1$H NMR (400 MHz, $CD_3OD$): δ=7.86 (s, 1H), 7.50 (t, J=8.4 Hz, 1H), 7.47-7.41 (m, 2H), 7.26-7.21 (m, 1H), 7.17-7.12 (m, 2H), 6.94 (dd, J=8.4, 2.4 Hz, 1H), 6.88 (dd, J=10.8, 2.4 Hz, 1H), 4.24-4.18 (m, 1H), 3.75 (t, J=10.8 Hz, 1H), 3.68-3.47 (m, 4H), 2.26-2.18 (m, 1H), 2.16-2.04 (m, 1H), 1.84-1.76 (m, 1H), 1.59-1.47 (m, 1H).

SFC: $t_R$=5.802 min, 100% optical purity.

Method: Column: Chiralcel OJ-3 150×4.6 mm I.D., 3 μm Mobile phase: A: $CO_2$ B: methanol (0.05% DEA) Gradient: from 5% to 40% of B in 5 min and from 40% to 5% of B in 0.5 min, hold 5% of B for 1.5 min Flow rate: 2.5 mL/min Column temp.: 35° C. ABPR: 1500 psi.

The following compounds were synthesized according to method B:

| Cpd No. | LC-MS method | LC-MS retention time ($t_R$, min) | HPLC method | HPLC retention time ($t_R$, min) |
|---|---|---|---|---|
| 8 | A | 2.356 | B | 3.00 |
| 9 | A | 2.340 | B | 2.99 |
| 10 | A | 2.410 | B | 2.98 |
| 11 | A | 2.365 | B | 3.05 |
| 12 | A | 2.585 | B | 3.11 |
| 13 | A | 2.588 | B | 3.11 |
| 14 | A | 2.514 | B | 3.13 |
| 15 | A | 2.509 | B | 3.14 |

| Cpd No. | Analytical SFC method | SFC retention time ($t_R$, min) | NMR |
|---|---|---|---|
| 8 | B | 4.059 | $^1$H NMR (400 MHz, $CD_3OD$): δ = 7.84 (s, 1H), 7.54 (t, J = 8.4 Hz, 1H), 7.47-7.41 (m, 2H), 7.26-7.20 (m, 1H), 7.17-7.12 (m, 2H), 6.94 (dd, J = 8.0, 2.0 Hz, 1H), 6.88 (dd, J = 10.8, 2.4 Hz, 1H), 4.56-4.51 (m, 1H), 3.89 (dd, J = 11.6, 3.6 Hz, 1H), 3.65-3.48 (m, 4H), 2.51-2.42 (m, 1H), 2.12-2.02 (m, 1H), 1.99-1.85 (m, 1H), 1.64-1.55 (m, 1H). |
| 9 | B | 4.161 | $^1$H NMR (400 MHz, $CD_3OD$): δ = 7.84 (s, 1H), 7.53 (t, J = 8.4 Hz, 1H), 7.47-7.41 (m, 2H), 7.25-7.19 (m, 1H), 7.17-7.12 (m, 2H), 6.94 (dd, J = 8.4, 2.0 Hz, 1H), 6.87 (dd, J = 11.2, 2.4 Hz, 1H), 4.56-4.50 (m, 1H), 3.88 (dd, J = 12.0, 3.6 Hz, 1H), 3.65-3.48 (m, 4H), 2.50-2.41 (m, 1H), 2.12-2.02 (m, 1H), 1.97-1.86 (m, 1H), 1.64-1.55 (m, 1H). |
| 10 | B | 4.405 | $^1$H NMR (400 MHz, $CD_3OD$): δ = 7.86 (s, 1H), 7.50 (t, J = 8.4 Hz, 1H), 7.47-7.41 (m, 2H), 7.26-7.20 (m, 1H), 7.17-7.12 (m, 2H), 6.94 (dd, J = 8.4, 2.4 Hz, 1H), 6.88 (dd, J = 10.8, 2.4 Hz, 1H), 4.24-4.18 (m, 1H), 3.75 (t, 7 = 11.2 Hz, 1H), 3.68-3.48 (m, 4H), 2.27-2.19 (m, 1H), 2.16-2.04 (m, 1H), 1.84-1.76 (m, 1H), 1.59-1.47 (m, 1H). |
| 11 | B | 5.802 | $^1$H NMR (400 MHz, $CD_3OD$): δ = 7.86 (s, m), 7.50 (t, J = 8.4 Hz, 1H), 7.47-7.41 (m, 2H), 7.26-7.21 (m, 1H), 7.17-7.12 (m, 2H), 6.94 (dd, J = 8.4, 2.4 Hz, 1H), 6.88 (dd, J = 10.8, 2.4 Hz, 1H), 4.24-4.18 (m, 1H), 3.75 (t, J = 10.8 Hz, 1H), 3.68-3.47 (m, 4H), 2.26-2.18 (m, 1H), 2.16-2.04 (m, 1H), 1.84-1.76 (m, 1H), 1.59-1.47 (m, 1H). |
| 12 | C | 1.705 | $^1$H NMR (400 MHz, CD30D): δ = 7.87 (s, 1H), 7.42-7.39 (m, 2H), 7.29-7.25 (m, 1H), 7.20-7.16 (m, 1H), 7.12 (d, J = 8.0 Hz, 2H), 6.98-6.93 (m, 1H), 4.23-4.20 (m, 1H), 3.74 (t, J = 11.2 Hz, 1H), 3.66-3.53 (m, 4H), 2.24-2.21 (m, 1H), 2.14-2.03 (m, 1H), 1.81-1.77 (m, 1H), 1.57-1.48 (m, 1H). $^{19}$FNMR (400 MHz, Methanol-d4): δ = −138.812, −56.777. |
| 13 | C | 3.338 | $^1$H NMR (400 MHz, $CD_3OD$): δ = 7.88 (s, 1H), 7.43-7.39 (m, 2H), 7.30-7.25 (m, 1H), 7.20-7.17 (m, 1H), 7.12 (d, J = 8.0 Hz, 2H), 6.98-6.93 (m, 1H), 4.23-4.20 (m, 1H), 3.74 (t, J = 11.2 Hz, 1H), 3.67-3.60 (m, 1H), 3.57-3.51 (m, 3H), 2.24-2.21 (m, 1H), 2.15-2.04 (m, 1H), 1.81-1.78 (m, 1H), 1.60-1.47 (m, 1H). $^{19}$F NMR (400 MHz, $CD_3OD$): δ = −138.887, −156.792. |
| 14 | C | 3.349 | $^1$H NMR (400 MHz, $CD_3OD$): δ = 7.86 (s, 1H), 7.64 (d, J = 8.8 Hz, 2H), 7.22-7.10 (m, 4H), 7.03-6.99 (m, 1H), 4.21-4.18 (dd, J = 10.8, 2.0 Hz, 1H), 3.76 (t, J = 11.2 Hz, 1H), 3.67-3.59 (m, 1H), 3.58-3.52 (m, 3H), 2.22-2.06 (m, 2H), 1.81-1.78 (m, 1H), 1.57-1.47 (m, 1H). $^{19}$F NMR (400 MHz, $CD_3OD$): δ = −138.647, −157.775. |
| 15 | C | 5.687 | $^1$H NMR (400 MHz, $CD_3OD$): δ = 7.86 (s, 1H), 7.64 (d, J = 8.8 Hz, 2H), 7.22-7.10 (m, 4H), 7.03-6.99 (m, 1H), 4.21-4.18 (dd, J = 10.8, 2.0 Hz, 1H), 3.76 (t, J= 11.2 Hz, 1H), 3.67-3.59 (m, 1H), 3.58-3.52 (m, 3H), 2.22-2.06 (m, 2H), 1.81-1.78 (m, 1H), 1.57-1.47 (m, 1H). $^{19}$F NMR (400 MHz, $CD_3OD$): δ = -138.722, -157.952. |

Biological Data

BTK WT and BTK C481S HTRF Kinase Assay

Recombinant BTK wild type (BTK WT) was purchased from Thermo fisher. Recombinant BTK(C481S) was purchased from SignalChem. The inhibition potency of compounds against BTK and BTK(C481S) was assessed using Homogenous Time Resolved Fluorescence approach.

In brief, recombinant kinases were pre-incubated in the presence or absence of compound at room temperature for 30 minutes. The reaction was initiated by the addition of the ATP and substrate peptide which could be phosphorylated by kinases in the reaction. After 120 minutes incubation, the reaction was stopped by the addition of the detection reagent mix containing EDTA. The fluorescence was measured at 615 nm and 665 nm, respectively with excitation wavelength at 320 nm. The calculated signal ratio of 665 nm/615 nm is proportional to the kinase activity. The concentration of compound producing 50% inhibition of the respective kinase (IC50) was calculated using four-parameter logistic fit with XL-fit.

| Cpd No. | BTK WT $IC_{50}$(nM) | BTK C481S $IC_{50}$ (nM) |
|---|---|---|
| Ibrutinib | 0.22 | 9.26 |
| 1 | 1.16 | 1.06 |
| 2 | 0.60 | 0.66 |
| 3 | 6.29 | 6.59 |
| 4 | 0.49 | 0.61 |
| 5 | 4.92 | 5.42 |
| 6 | 0.62 | 0.42 |
| 7 | 1.59 | 1.53 |
| 8 | 3.45 | 2.80 |
| 9 | 8.64 | 6.42 |
| 10 | 0.90 | 0.95 |
| 11 | 4.51 | 5.03 |
| 12 | 0.27 | 0.27 |
| 13 | 3.29 | 3.81 |
| 14 | 0.70 | 0.86 |
| 15 | 6.72 | 6.11 |

TMD8 Cell Line p-BTK Elisa Assay

TMD-8 cells were plated in 96 well plates at the density of 30000 cells/well with RPMI1640 media with 1.5% foetal bovine serum. The test compounds were added to the cells and cells were incubated for 0.5 hour at 37° C., 5% $CO_2$. Then pervanadate solution was added to the cells to make a final concentration of 100 μM, and cells were incubated for a further 1 hour at 37° C., 5% $CO_2$. After compound treatment, the cells were lysed and p-BTK signal was detected following procedure exactly follow PathScan® Phospho-Btk (Tyr223) Sandwich ELISA kit (#23843). The plate was read on a Multiscan Spectrum reader set to 450 nm wavelengths. This data was processed in GraphPad Prism software.

| Cpd No. | p-BTK $IC_{50}$ (nM) | Maximal Inhibition Level (%) |
|---|---|---|
| Ibrutinib | 3.0 | 100 |
| 1 | 18.9 | 97.9 |
| 2 | 29.1 | 98.4 |
| 3 | 78.4 | 96.2 |
| 4 | 30.7 | 97.4 |
| 5 | 48.7 | 95.8 |
| 6 | 26.2 | 98.8 |
| 7 | 137.5 | 97.9 |
| 8 | 42.1 | 100.9 |
| 9 | 123.5 | 107.7 |
| 10 | 29.0 | 98.5 |
| 11 | 34.7 | 99.3 |

-continued

| Cpd No. | p-BTK $IC_{50}$ (nM) | Maximal Inhibition Level (%) |
|---|---|---|
| 12 | 23.2 | 97.0 |
| 14 | 24.3 | 98.0 |

HEK293-BTK(WT) and HEK293-BTK(C481S)

Full-length cDNAs of BTK containing C481S mutation was generated by mutagenesis using QuikChange II XL Site-Directed Mutagenesis Kit. The mutated BTK cDNAs were confirmed by sequencing. The cDNAs of BTK(WT), BTK-C481S were then cloned into PLVX-Puro lentivirus vector. The lentivirus were packaged in 293T cell by transfected with lentivirus vectors and package mix. BTK(WT), BTK-C481S lentivirus were transfected into HEK293 cells. The transfected cells were selected in 2 μg/mL of puromycin. Stable polyclonal cell lines were confirmed by WB and used for further study. HEK293-BTK(WT), HEK293-BTK (C481S) cells were cultured in DMEM (Gibco; 12430), with 10% FBS (Gibco; 10099), with 1 μg/mL Puromycin. All the cells were maintained in a humidified incubator at 37° C. with 5% $CO_2$.

HEK293-BTK(WT) and HEK293-BTK(C481S) cells were plated in 96 well plates at the density of 5000 cells/well with RPMI1640 media with 1.5% foetal bovien serum. The test compounds were added to the cells and cells were incubated for 1.5 hour at 37° C., 5% $CO_2$. After compound treatment, the cells were lysed and p-BTK signal was detected following procedure exactly follow PathScan® Phospho-Btk (Tyr223) Sandwich ELISA kit (#23843). The plate was read on a Multiscan Spectrum reader set to 450 nm wavelengths. The data were processed in Graph Pad Prism software.

| Cpd No. | HEK293 WT $IC_{50}$ (nM) | HEK293 C481S $IC_{50}$ (nM) |
|---|---|---|
| Ibrutinib | 18.1 | 770.4 |
| 2 | 27.3 | 70.6 |
| 4 | 18.8 | 84.2 |
| 6 | 33.4 | 75.4 |
| 10 | 60.0 | 170.0 |
| 12 | 17.6 | 46.8 |
| 14 | 16.0 | 36.3 |

TMD-8 Anti-Proliferation Assay

TMD-8 cells were prepared in RPMI1640 media containing 10% foetal bovine, and plated in 384 well plates at 1500 cells per well, The cells were incubated overnight at 37° C., 5% $CO_2$. After incubation, compounds with different concentration were added to the assay plates and incubate cells for a further 72 hours at 37° C., 5% $CO_2$. Following 72 hours incubation, 15 μl of CellTiter 96® AQueous One Solution Reagent was added to each well and the plates incubated at room temperature for 30 mins. Cell viability was determined using the CellTiter-Glo (Promega, USA). The CellTiter-Glo assay was performed according to the manufacturer's instructions, and luminescence was determined in a multilabel reader (Envision, PerkinElmer, USA). The data were processed in XLfit software.

| Cpd No. | Anti-proliferation IC50 (nM) |
|---|---|
| Ibrutinib | 1.9 |
| 1 | 24.2 |
| 2 | 22.7 |
| 3 | 106.4 |

-continued

| Cpd No. | Anti-proliferation IC50 (nM) |
|---|---|
| 4 | 16.2 |
| 5 | 102.0 |
| 6 | 27.4 |
| 7 | 219.1 |
| 8 | 77.0 |
| 9 | 160.5 |
| 10 | 32.2 |
| 11 | 70.9 |

In Vitro Rat/Human Hepatocytes Clearance Assay

Rat hepatocytes in male gender and human hepatocytes in mixed gender were obtained from commercial vendors (e.g., BioreclamationIVT) and stored at −150° C. prior to use. 10 mM stock solutions of tested compounds were prepared in DMSO. Thawing medium and supplement incubation medium (serum-free) were placed in a 37° C. water bath for at least 15 minutes prior to use. Stock solutions were diluted to 100 μM by combining 198 μL acetonitrile and 2 μL of 10 mM stock solution.

Vials of cryopreserved hepatocytes were removed from storage, ensured that vials remain at cryogenic temperatures. The vials were thawed in a 37° C. water bath with gently shaking. Vials were kept in a water bath until all ice crystals had dissolved and were no longer visible. Vials were sprayed with 70% ethanol before being transferred to a biosafety cabinet. And then the contents were poured into the 50 mL thawing medium conical tube. Vials were centrifuged at 100 g for 10 minutes at room temperature. Thawing medium was aspirated and hepatocytes were resuspended with serum-free incubation medium to yield ~1.5×106 cells/mL.

Cell viability and density were counted using a Trypan Blue exclusion, and then cells were diluted with serum-free incubation medium to a working cell density of 1×106 viable cells/ml. A portion of the hepatocytes at 1×106 viable cells/mL was boiled for 10 min prior to adding to the plate as negative control to eliminate the enzymatic activity so that little or no substrate turnover should be observed. The inactivated hepatocytes were used to prepare negative samples, which were used to exclude the misleading factor that resulted from instability of chemical itself.

Aliquots of 247.5 μL hepatocytes were dispensed into each well of a 96-well non-coated plate. The plate was placed in the incubator on an orbital shaker for approximately 10 minutes. Aliquots of 2.5 μL of the 100 μM test compounds were added into respective wells of the non-coated 96-well plate to start the reaction. This assay was performed in duplicate. The plate was incubated in the incubator on an orbital shaker for the designed time points. 20 μL of contents were transferred and mixed with 6 volumes (120 μL) of cold acetonitrile with internal standard to terminate the reaction at time points of 5, 15, 30, 45, 60, 80 and 100 minutes. Samples were centrifuges for 20 minutes at 4000 g and aliquots of 100 μl of the supernatants were used for LC-MS/MS analysis for measurement of test compounds.

In vitro hepatocyte clearance was estimated based on determination of elimination half-life (T1/2) of compounds disappearance from their initial concentrations. Peak area ratios of each compound (test or control) to IS was calculated. Ln (% Control) versus Incubation Time (min) curve was plotted, and the slope of a linear fitting line was calculated. Drug elimination rate constant k (min-1), T1/2 (min), and in vitro intrinsic clearance CLint (μL/min/E6) was calculated according to the following equations:

$$k=-\text{slope}$$

$$T1/2=0.693/k$$

$$CL\text{int}=k/\text{Chep}$$

Where Chep (cells×μL-1) is the cell concentration in the incubation system.

Procedure for Log D Determination

10 μL of working solution of each cassette is placed in order into respective 96-well rack position (Log D plate). Add 500 μL of saturated octanol into each vial of the above cap-less Log D plate followed by the addition of 500 μL of saturated phosphate buffer. Seal with a moulded PTFE/SIL 96-Well Plate Cover.

The Log D plate is transferred to the Eppendorf Thermomixer Comfort plate shaker and shaken at 25° C., 2,000 rpm for 2 hours.

The samples are centrifuged at 4,000 rpm at 25° C. for 30 minutes to separate the phases. Pipette and syringe are used to pipette about 100 μL from the octanol and buffer phases to a new 96-well plate, respectively.

5 μL of octanol sample is transferred to a new 96-well plate, followed by addition of 495 μL of a mixture of $H_2O$ and acetonitrile containing internal standard (1:1) as 100 fold octanol samples. Vortex for 5 minutes at 1,000 rpm.

50 μL of 100 fold samples are transferred to new 96-well plate, followed by addition of 450 μL of a mixture of $H_2O$ and acetonitrile containing internal standard (1:1) as 1,000 fold octanol samples. Vortex for 5 minutes at 1,000 rpm.

The 1,000 folds octanol samples are serially diluted into 10,000, 100,000 and 1,000,000 folds with a mixture of $H_2O$ and acetonitrile containing internal standard (1:1).

50 μL of buffer samples are transferred to new 96-well plate, followed by addition of 450 μL of a mixture of $H_2O$ and acetonitrile containing internal standard (1:1) as 10 folds buffer samples. Vortex for 5 minutes at 1,000 rpm.

The 10 folds buffer samples are serially diluted into 100, 1,000 and 10,000 folds with a mixture of $H_2O$ and acetonitrile containing internal standard (1:1). The samples are evaluated by LC/MS/MS analysis. All compounds are tested in singlicate.

All calculations are carried out using Microsoft Excel. The concentrations of test compound in octanol/buffer solution are evaluated by LC/MS/MS. Calculate the Log D value of the test compound as follows:

$$\text{Log}\,D=\frac{1}{n}*\sum\left(Log\left[(\text{Area Ratio }Oct\times DF\ Oct)/(\text{Area Ratio }Buf\times DF\ Buf)\right]\right)$$

DF means the dilution factor.

Procedure for Protein Binding Measurements in Human Plasma by Using Equilibrium Dialysis Add 597 μL of blank plasma into each vial of a new plastic plate or separate plastic tube by addition of 3 μL of the working solution of each cassette, vortex at 1,000 rpm for 5 minutes. The final percent volume of organic solvent is 0.5% and the final concentration for test compound is 5 μM. Immediately transfer 50 μL of the spiked plasma suspension to a 96-well plate to act as T=0 control sample. The samples are treated the same as the samples after incubation. Place all remaining spiked plasma in the incubator for the duration of the study.

Place inserts open end up into the wells of the base plate. Add 500 μL of phosphate buffer (pH 7.4) to the buffer chamber, which is indicated by the white ring. Add 300 µL of spiked plasma sample into the sample chamber, which is indicated by the red ring. Cover the unit with gas permeable lid and incubate for 18 hours at 37° C. at 300 rpm with 5% $CO_2$ on an orbital shaker in the $CO_2$ incubator. At the end of incubation, remove lid and pipette 50 µL of post-dialysis samples from both buffer and plasma chambers into separated 96-well plate for analysis, respectively.

At the same time, the remaining spiked plasma sample in the plastic plate or separate plastic tube is incubated for 18 hours at 37° C. with 5% $CO_2$ in the $CO_2$ incubator. At T=18 hours, transfer 50 µL of the original spiked plasma suspension to the 96-well plate for analysis.

Add 50 µL of Human plasma to the buffer samples, and an equal volume of PBS to the collected plasma samples. Vortex the plate at 1,000 rpm for 2 minutes and add 400 µL of acetonitrile containing an appropriate internal standard (IS) to precipitate protein and release compound. Vortex at 1,000 rpm for 10 minutes. Centrifuge for 30 minutes at 4,000 rpm. Transfer 250 µl of the supernatant to new 96-well plates and centrifuge again (4,000 rpm, 30 minutes). Then transfer 100 µL of the supernatant to new 96-well plates for analysis. Add 100 µL of distilled water to each sample and vortex for 5 minutes at 1,000 rpm for analysis by LC-MS/MS. All compounds are tested in singlicate at 5 µM in human plasma.

All calculations are carried out using Microsoft Excel.

Calculate the percentage of unbound, percentage of bound and recovery of test compound as follows:

$$\%\ \text{Unbound} = (Conc._{buffer\ chamber}/Conc._{plasma\ chamber}) \times 100\%$$

$$\%\ \text{Bound} = 100\% - \%\ \text{Free}$$

$$\%\ \text{Recovery} = (500 \times Conc._{buffer\ chamber} + 300 \times Conc._{plasma\ chamber}) / (300 \times Conc._{Total\ sample}) \times 100$$

$$LogK = Log\left(\frac{\%\ \text{Bound}}{100 - \%\ \text{Bound}}\right)$$

$$\text{Remaining}\ \% = Conc._{18hr}/Conc._{0hr} \times 100\%$$

Results

| Cpd. No. | logD | Hu Mic Clint (µL/min/mg) | Rat Hep Clint (µL/min/10^6 cells) | hPPB (fu %) | DMSO solubility (µM) | Human Hep Clint (µL/min/10^6 cells) |
|---|---|---|---|---|---|---|
| 1 | 3.14 | 44.9 | 12.4 | 9.8 | 51.3 | 28.9 |
| 2 | 3.01 | 12.7 | 6.1 | 10.6 | 15.1 | 4.6 |
| 3 | 2.88 | 23.7 | 8.8 | 11.9 | 34.1 | 12.9 |
| 4 | 3.10 | 7.44 | 7.2 | 8.8 | 63.1 | 5.6 |
| 5 | 2.89 | 13.0 | 9.0 | 9.0 | 61.9 | 9.0 |
| 6 | 3.28 | 8.8 | 8.2 | 7.5 | 43.9 | 2.1 |
| 7 | 3.19 | 13.3 | 4.9 | 7.3 | 45.8 | 3.3 |
| 8 | 3.10 | 41.3 | 48.5 | 9.3 | 21.0 | 6.1 |
| 9 | 3.00 | 34.3 | 27.2 | 5.8 | 20.3 | 5.9 |
| 10 | 3.07 | 7.0 | 17.1 | 8.1 | 20.5 | 1.7 |
| 11 | 3.09 | 9.3 | 11.7 | 8.9 | <1.6 | 3.6 |
| 12 | 3.18 | <3 | 46.8 | 7.4 | 45.7 | 2.0 |
| 13 | 3.21 | <3 | 21.4 | 8.4 | 113 | 5.9 |
| 14 | 3.29 | <3 | 9.48 | 4.9 | 48.0 | 2.5 |
| 15 | 2.98 | <3 | 7.9 | 6.4 | 84.0 | 2.1 |
| 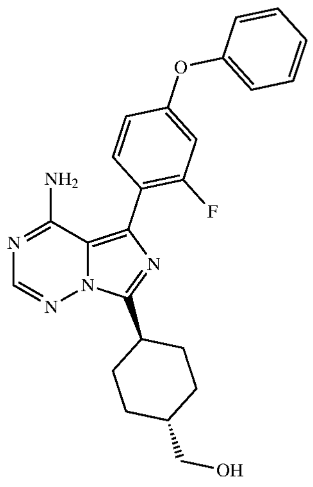 WO2009143051 Example 272 | 3.98 | 19.3 | 254.9 | 2.57 | <1.6 | 123.6 |

-continued

| Cpd. No. | logD | Hu Mic Clint (μL/min/mg) | Rat Hep Clint (μL/min/10/\6 cells) | hPPB (fu %) | DMSO solubility (μM) | Human Hep Clint (μL/min/10/\6 cells) |
|---|---|---|---|---|---|---|
| 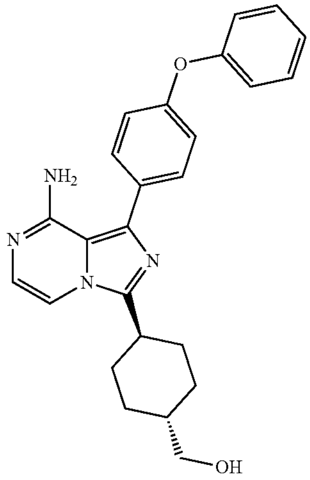 WO2009143051 Example 237 | 4.16 | 140.8 | 119.3 | 2.89 | <1.6 | 92.9 |

Short Oral Absorption (SOA) Assay in Rats.

A Short oral absorption (SOA) model is an in-vivo screening model to identify brain penetration of a compound. To evaluate the potential of a compound to cross the blood-brain barrier in rats, total brain-to-plasma ratio ($K_{p,brain}$) was measured $AUC_{brain}/AUC_{plasma}$. CSF-to-plasma ratio ($K_{p,CSF}$) was determined by either $AUC_{CSF}/AUC_{plasma}$ or the average of CSF-to-plasma ratios at available time points after oral administration, respectively. Free fractions of in biological matrix were determined by in vitro plasma and brain binding assay in a separate study. $K_{p,uu,brain}$ and $K_{p,uu,CSF}$ were calculated by the following equations: (1) $K_{p,uu,brain}=K_{p,\ brain}\times f_{u,brain}/f_{u,plasma}$; (2) $K_{p,uu,CSF}=K_{p,CSF}/f_{u,plasma}$.

| Cpd No. | Rat fu, br (%)/fu, pl (%) | Kp, brain | Kp, uu brain | Kp, uu CSF |
|---|---|---|---|---|
| 2 | 3.3/3.8 | 1.35 | 1.19 | 0.86 |
| 10 | 2.2/3.7 | 0.38 | 0.23 | 0.56 |
| 14 | 1.5/2.0 | 0.32 | 0.23 | 0.59 |

What is claimed is:

1. A compound of formula (I):

(I)

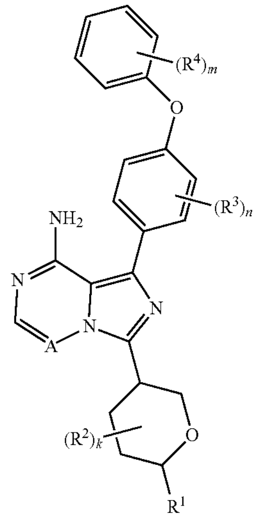

wherein:

$R^1$ is selected from hydrogen, $C_{1-6}$alkyl, $C_{1-6}$alkoxy, N—$C_{1-6}$alkylamino, N,N—$(C_{1-6}alkyl)_2$amino, carbocyclyl and heterocyclyl; wherein $R^1$ may be optionally substituted by one or more $R^5$;

$R^2$ is selected from halo, $C_{1-3}$alkyl, $C_{1-3}$alkoxy, carbocyclyl and heterocyclyl; or two $R^2$, either on the same atom or on adjoining atoms, may together with the atoms to which they are attached form a 3-7 membered ring;

k is 0-4;

$R^3$ is selected from halo, $C_{1-3}$alkyl and $C_{1-3}$alkoxy;

n is 0-4;

$R^4$ is selected from halo, $C_{1-3}$alkyl and $C_{1-3}$alkoxy;

m is 0-5;

A is =N— or =C($R^6$)—;

$R^5$ is selected from halo, hydroxy, $C_{1-6}$alkoxy, amino, N—$C_{1-6}$alkylamino, N,N—($C_{1-6}$alkyl)$_2$amino, carbocyclyl and heterocyclyl; wherein $R^5$ may be independently optionally substituted by one or more $R^7$;

$R^6$ is selected from hydrogen and halo;

$R^7$ is selected from halo, hydroxy, amino, $C_{1-3}$alkyl and $C_{1-3}$alkoxy;

or a pharmaceutically acceptable salt thereof.

2. A compound of formula (I) or a pharmaceutically acceptable salt thereof, as claimed in claim 1, wherein $R^1$ is selected from hydrogen, methyl, hydroxymethyl, methoxymethyl, N,N-dimethylaminomethyl and azetidin-1-ylmethyl.

3. A compound of formula (I) or a pharmaceutically acceptable salt thereof, as claimed in claim 1, wherein k is 0.

4. A compound of formula (I) or a pharmaceutically acceptable salt thereof, as claimed in claim 1, wherein $R^3$ is fluoro.

5. A compound of formula (I) or a pharmaceutically acceptable salt thereof, as claimed in claim 1, wherein n is 0-2.

6. A compound of formula (I) or a pharmaceutically acceptable salt thereof, as claimed in claim 1, wherein $R^4$ is fluoro.

7. A compound of formula (I) or a pharmaceutically acceptable salt thereof, as claimed in claim 1, wherein m is 0-2.

8. A compound of formula (I) or a pharmaceutically acceptable salt thereof, as claimed in claim 1, wherein A is =N— or =C(H)—.

9. A compound of formula (I) or a pharmaceutically acceptable salt thereof, as claimed in claim 1 selected from:

(5-(8-amino-1-(4-phenoxyphenyl)imidazo[1,5-a]pyrazin-3-yl)tetrahydro-2H-pyran-2-yl)methanol; (5-(8-amino-1-(2-fluoro-4-phenoxyphenyl)imidazo[1,5-a]pyrazin-3-yl)tetrahydro-2H-pyran-2-yl)methanol; (5-(8-amino-1-(2,3-difluoro-4-phenoxyphenyl)imidazo[1,5-a]pyrazin-3-yl)tetrahydro-2H-pyran-2-yl)methanol;

(5-(8-amino-1-(4-(2,3-difluorophenoxy)phenyl)imidazo[1,5-a]pyrazin-3-yl)tetrahydro-2H-pyran-2-yl)methanol; (5-(4-amino-5-(2-fluoro-4-phenoxyphenyl)imidazo[5,1-f][1,2,4]triazin-7-yl)tetrahydro-2H-pyran-2-yl)methanol;

(5-(4-amino-5-(2,3-difluoro-4-phenoxyphenyl)imidazo[5,1-f][1,2,4]triazin-7-yl)tetrahydro-2H-pyran-2-yl)methanol;

(5-(4-amino-5-(4-(2,3-difluorophenoxy)phenyl)imidazo[5,1-f][1,2,4]triazin-7-yl)tetrahydro-2H-pyran-2-yl)methanol;

3-(6-((dimethylamino)methyl)tetrahydro-2H-pyran-3-yl)-1-(2-fluoro-4-phenoxyphenyl)imidazo[1,5-a]pyrazin-8-amine;

7-(6-((dimethylamino)methyl)tetrahydro-2H-pyran-3-yl)-5-(2-fluoro-4-phenoxyphenyl)imidazo[5,1-f][1,2,4]triazin-4-amine;

7-(6-(azetidin-1-ylmethyl)tetrahydro-2H-pyran-3-yl)-5-(2-fluoro-4-phenoxyphenyl)imidazo[5,1-f][1,2,4]triazin-4-amine;

5-(2-fluoro-4-phenoxyphenyl)-7-(6-(methoxymethyl)tetrahydro-2H-pyran-3-yl)imidazo[5,1-f][1,2,4]triazin-4-amine;

5-(2-fluoro-4-phenoxyphenyl)-7-(tetrahydro-2H-pyran-3-yl)imidazo[5,1-f][1,2,4]triazin-4-amine; and 5-(2-fluoro-4-phenoxyphenyl)-7-(6-methyltetrahydro-2H-pyran-3-yl)imidazo[5,1-f][1,2,4]triazin-4-amine.

10. A compound of formula (I) or a pharmaceutically acceptable salt thereof, as claimed in claim 1 selected from:

((2R,5R)-5-(8-amino-1-(4-phenoxyphenyl)imidazo[1,5-a]pyrazin-3-yl)tetrahydro-2H-pyran-2-yl)methanol;

((2R,5R)-5-(8-amino-1-(2-fluoro-4-phenoxyphenyl)imidazo[1,5-a]pyrazin-3-yl)tetrahydro-2H-pyran-2-yl)methanol;

((2R,5R)-5-(8-amino-1-(2,3-difluoro-4-phenoxyphenyl)imidazo[1,5-a]pyrazin-3-yl)tetrahydro-2H-pyran-2-yl)methanol;

((2R,5R)-5-(8-amino-1-(4-(2,3-difluorophenoxy)phenyl)imidazo[1,5-a]pyrazin-3-yl)tetrahydro-2H-pyran-2-yl)methanol;

((2R,5R)-5-(4-amino-5-(2-fluoro-4-phenoxyphenyl)imidazo[5,1-f][1,2,4]triazin-7-yl)tetrahydro-2H-pyran-2-yl)methanol;

((2R,5R)-5-(4-amino-5-(2,3-difluoro-4-phenoxyphenyl)imidazo[5,1-f][1,2,4]triazin-7-yl)tetrahydro-2H-pyran-2-yl)methanol;

((2R,5R)-5-(4-amino-5-(4-(2,3-difluorophenoxy)phenyl)imidazo[5,1-f][1,2,4]triazin-7-yl)tetrahydro-2H-pyran-2-yl)methanol;

3-((3R,6R)-6-((dimethylamino)methyl)tetrahydro-2H-pyran-3-yl)-1-(2-fluoro-4-phenoxyphenyl)imidazo[1,5-a]pyrazin-8-amine;

7-((3R,6R)-6-((dimethylamino)methyl)tetrahydro-2H-pyran-3-yl)-5-(2-fluoro-4-phenoxyphenyl)imidazo[5,1-f][1,2,4]triazin-4-amine;

7-((3R,6R)-6-(azetidin-1-ylmethyl)tetrahydro-2H-pyran-3-yl)-5-(2-fluoro-4-phenoxyphenyl)imidazo[5,1-f][1,2,4]triazin-4-amine;

5-(2-fluoro-4-phenoxyphenyl)-7-((3R,6R)-6-(methoxymethyl)tetrahydro-2H-pyran-3-yl)imidazo[5,1-f][1,2,4]triazin-4-amine;

(R)-5-(2-fluoro-4-phenoxyphenyl)-7-(tetrahydro-2H-pyran-3-yl)imidazo[5,1-f][1,2,4]triazin-4-amine; and 5-(2-fluoro-4-phenoxyphenyl)-7-((3R,6R)-6-methyltetrahydro-2H-pyran-3-yl)imidazo[5,1-f][1,2,4]triazin-4-amine;

((2S,5S)-5-(8-amino-1-(4-phenoxyphenyl)imidazo[1,5-a]pyrazin-3-yl)tetrahydro-2H-pyran-2-yl)methanol;

((2S,5S)-5-(8-amino-1-(2-fluoro-4-phenoxyphenyl)imidazo[1,5-a]pyrazin-3-yl)tetrahydro-2H-pyran-2-yl)methanol;

((2S,5S)-5-(8-amino-1-(2,3-difluoro-4-phenoxyphenyl)imidazo[1,5-a]pyrazin-3-yl)tetrahydro-2H-pyran-2-yl)methanol;

((2S,5S)-5-(8-amino-1-(4-(2,3-difluorophenoxy)phenyl)imidazo[1,5-a]pyrazin-3-yl)tetrahydro-2H-pyran-2-yl)methanol;

((2S,5S)-5-(4-amino-5-(2-fluoro-4-phenoxyphenyl)imidazo[5,1-f][1,2,4]triazin-7-yl)tetrahydro-2H-pyran-2-yl)methanol;

((2S,5S)-5-(4-amino-5-(2,3-difluoro-4-phenoxyphenyl)imidazo[5,1-f][1,2,4]triazin-7-yl)tetrahydro-2H-pyran-2-yl)methanol;

((2S,5S)-5-(4-amino-5-(4-(2,3-difluorophenoxy)phenyl)imidazo[5,1-f][1,2,4]triazin-7-yl)tetrahydro-2H-pyran-2-yl)methanol;

3-((3S,6S)-6-((dimethylamino)methyl)tetrahydro-2H-pyran-3-yl)-1-(2-fluoro-4-phenoxyphenyl)imidazo[1,5-a]pyrazin-8-amine;

7-((3S,6S)-6-((dimethylamino)methyl)tetrahydro-2H-pyran-3-yl)-5-(2-fluoro-4-phenoxyphenyl)imidazo[5,1-f][1,2,4]triazin-4-amine;

7-((3S,6S)-6-(azetidin-1-ylmethyl)tetrahydro-2H-pyran-3-yl)-5-(2-fluoro-4-phenoxyphenyl)imidazo[5,1-f][1,2,4]triazin-4-amine;

5-(2-fluoro-4-phenoxyphenyl)-7-((3S,6S)-6-(methoxymethyl)tetrahydro-2H-pyran-3-yl)imidazo[5,1-f][1,2,4]triazin-4-amine;

(S)-5-(2-fluoro-4-phenoxyphenyl)-7-(tetrahydro-2H-pyran-3-yl)imidazo[5,1-f][1,2,4]triazin-4-amine; and 5-(2-fluoro-4-phenoxyphenyl)-7-((3S,6S)-6-methyltetrahydro-2H-pyran-3-yl)imidazo[5,1-f][1,2,4]triazin-4-amine;

((2S,5R)-5-(8-amino-1-(4-phenoxyphenyl)imidazo[1,5-a]pyrazin-3-yl)tetrahydro-2H-pyran-2-yl)methanol;

((2S,5R)-5-(8-amino-1-(2-fluoro-4-phenoxyphenyl)imidazo[1,5-a]pyrazin-3-yl)tetrahydro-2H-pyran-2-yl)methanol;

((2S,5R)-5-(8-amino-1-(2,3-difluoro-4-phenoxyphenyl)imidazo[1,5-a]pyrazin-3-yl)tetrahydro-2H-pyran-2-yl)methanol;

((2S,5R)-5-(8-amino-1-(4-(2,3-difluorophenoxy)phenyl)imidazo[1,5-a]pyrazin-3-yl)tetrahydro-2H-pyran-2-yl)methanol;

((2S,5R)-5-(4-amino-5-(2-fluoro-4-phenoxyphenyl)imidazo[5,1-f][1,2,4]triazin-7-yl)tetrahydro-2H-pyran-2-yl)methanol;

((2S,5R)-5-(4-amino-5-(2,3-difluoro-4-phenoxyphenyl)imidazo[5,1-f][1,2,4]triazin-7-yl)tetrahydro-2H-pyran-2-yl)methanol;

((2S,5R)-5-(4-amino-5-(4-(2,3-difluorophenoxy)phenyl)imidazo[5,1-f][1,2,4]triazin-7-yl)tetrahydro-2H-pyran-2-yl)methanol;

3-((3S,6R)-6-((dimethylamino)methyl)tetrahydro-2H-pyran-3-yl)-1-(2-fluoro-4-phenoxyphenyl)imidazo[1,5-a]pyrazin-8-amine;

7-((3S,6R)-6-((dimethylamino)methyl)tetrahydro-2H-pyran-3-yl)-5-(2-fluoro-4-phenoxyphenyl)imidazo[5,1-f][1,2,4]triazin-4-amine;

7-((3S,6R)-6-(azetidin-1-ylmethyl)tetrahydro-2H-pyran-3-yl)-5-(2-fluoro-4-phenoxyphenyl)imidazo[5,1-f][1,2,4]triazin-4-amine;

5-(2-fluoro-4-phenoxyphenyl)-7-((3S,6R)-6-(methoxymethyl)tetrahydro-2H-pyran-3-yl)imidazo[5,1-f][1,2,4]triazin-4-amine; AND 5-(2-fluoro-4-phenoxyphenyl)-7-((3S,6R)-6-methyltetrahydro-2H-pyran-3-yl)imidazo[5,1-f][1,2,4]triazin-4-amine;

((2R,5S)-5-(8-amino-1-(4-phenoxyphenyl)imidazo[1,5-a]pyrazin-3-yl)tetrahydro-2H-pyran-2-yl)methanol;

((2R,5S)-5-(8-amino-1-(2-fluoro-4-phenoxyphenyl)imidazo[1,5-a]pyrazin-3-yl)tetrahydro-2H-pyran-2-yl)methanol;

((2R,5S)-5-(8-amino-1-(2,3-difluoro-4-phenoxyphenyl)imidazo[1,5-a]pyrazin-3-yl)tetrahydro-2H-pyran-2-yl)methanol;

((2R,5S)-5-(8-amino-1-(4-(2,3-difluorophenoxy)phenyl)imidazo[1,5-a]pyrazin-3-yl)tetrahydro-2H-pyran-2-yl)methanol;

((2R,5S)-5-(4-amino-5-(2-fluoro-4-phenoxyphenyl)imidazo[5,1-f][1,2,4]triazin-7-yl)tetrahydro-2H-pyran-2-yl)methanol;

((2R,5S)-5-(4-amino-5-(2,3-difluoro-4-phenoxyphenyl)imidazo[5,1-f][1,2,4]triazin-7-yl)tetrahydro-2H-pyran-2-yl)methanol;

((2R,5S)-5-(4-amino-5-(4-(2,3-difluorophenoxy)phenyl)imidazo[5,1-f][1,2,4]triazin-7-yl)tetrahydro-2H-pyran-2-yl)methanol;

3-((3R,6S)-6-((dimethylamino)methyl)tetrahydro-2H-pyran-3-yl)-1-(2-fluoro-4-phenoxyphenyl)imidazo[1,5-a]pyrazin-8-amine;

7-((3R,6S)-6-((dimethylamino)methyl)tetrahydro-2H-pyran-3-yl)-5-(2-fluoro-4-phenoxyphenyl)imidazo[5,1-f][1,2,4]triazin-4-amine;

7-((3R,6S)-6-(azetidin-1-ylmethyl)tetrahydro-2H-pyran-3-yl)-5-(2-fluoro-4-phenoxyphenyl)imidazo[5,1-f][1,2,4]triazin-4-amine;

5-(2-fluoro-4-phenoxyphenyl)-7-((3R,6S)-6-(methoxymethyl)tetrahydro-2H-pyran-3-yl)imidazo[5,1-f][1,2,4]triazin-4-amine; and 5-(2-fluoro-4-phenoxyphenyl)-7-((3R,6S)-6-methyltetrahydro-2H-pyran-3-yl)imidazo[5,1-f][1,2,4]triazin-4-amine.

11. A compound of formula (I) or a pharmaceutically acceptable salt thereof, as claimed in claim 1, wherein the compound is ((2S,5S)-5-(8-amino-1-(2-fluoro-4-phenoxyphenyl)imidazo[1,5-a]pyrazin-3-yl)tetrahydro-2H-pyran-2-yl)methanol.

12. A compound of formula (I) or a pharmaceutically acceptable salt thereof, as claimed in claim 1, wherein the compound is ((2S,5S)-5-(8-amino-1-(2,3-difluoro-4-phenoxyphenyl)imidazo[1,5-a]pyrazin-3-yl)tetrahydro-2H-pyran-2-yl)methanol.

13. A compound of formula (I) or a pharmaceutically acceptable salt thereof, as claimed in claim 1, wherein the compound is ((2S,5S)-5-(8-amino-1-(4-(2,3-difluorophenoxy)phenyl)imidazo[1,5-a]pyrazin-3-yl)tetrahydro-2H-pyran-2-yl)methanol.

14. A compound of formula (I) or a pharmaceutically acceptable salt thereof, as claimed in claim 1, wherein the compound is ((2S,5S)-5-(4-amino-5-(2-fluoro-4-phenoxyphenyl)imidazo[5,1-f][1,2,4]triazin-7-yl)tetrahydro-2H-pyran-2-yl)methanol.

15. A compound of formula (I) or a pharmaceutically acceptable salt thereof, as claimed in claim 1, wherein the compound is ((2S,5S)-5-(4-amino-5-(2,3-difluoro-4-phenoxyphenyl)imidazo[5,1-f][1,2,4]triazin-7-yl)tetrahydro-2H-pyran-2-yl)methanol.

16. A compound of formula (I) or a pharmaceutically acceptable salt thereof, as claimed in claim 1, wherein the compound is ((2S,5S)-5-(4-amino-5-(4-(2,3-difluorophenoxy)phenyl)imidazo[5,1-f][1,2,4]triazin-7-yl)tetrahydro-2H-pyran-2-yl)methanol.

17. A pharmaceutical composition which comprises a compound of formula (I) or a pharmaceutically acceptable salt thereof, as claimed in claim 1, in association with a pharmaceutically-acceptable diluent or carrier.

18. A method of inhibiting BTK by using one or more compound of formula (I) or a pharmaceutically acceptable salt thereof, as claimed in claim 1.

19. A method of inhibiting BTK, as claimed in claim 18, wherein the BTK is wild-type BTK or BTK with a C481 mutation.

20. A method of inhibiting BTK, as claimed in claim 19, wherein the BTK with a C481 mutation is selected from the group consisting of: BTK with a C481S mutation, BTK with a C481Y mutation, BTK with a C481R mutation and BTK with a C481F mutation.

21. A method of treating diseases or disorders in a warm-blooded animal thereof, which comprises administering to said animal an effective amount of a compound of formula (I) or a pharmaceutically acceptable salt thereof, as claimed in claim 1, wherein the disease or disorder is selected from: small lymphocytic lymphoma (SLL), follicular lymphoma, Richter's transformation, mantle cell lymphoma, chronic lymphocytic leukaemia (CLL), Waldenström's macroglobulinemia, non-Hodgkin lymphoma, primary central nervous system lymphoma, secondary central nervous system lymphoma, diffuse large B-cell lymphoma, Urticaria/Sjogren's syndrome, rheumatoid arthritis, osteoporosis, vasculitis, idiopathic thrombocytopenic purpura (ITP), myasthenia gravis, allergic rhinitis, asthma, multiple sclerosis or systemic lupus erythematosus, and wherein the warm-blooded animal is human.

22. A method of treating diseases or disorders in a warm-blooded animal thereof, as claimed in claim 21, wherein the disease or disorder is multiple sclerosis.

23. A compound of ((2S,5S)-5-(8-amino-1-(2-fluoro-4-phenoxyphenyl)imidazo[1,5-a]pyrazin-3-yl)tetrahydro-2H-pyran-2-yl)methanol.

24. A pharmaceutical composition which comprises a compound of claim 23 and a pharmaceutically-acceptable diluent or carrier.

25. A compound of ((2S,5S)-5-(8-amino-1-(2,3-difluoro-4-phenoxyphenyl)imidazo[1,5-a]pyrazin-3-yl)tetrahydro-2H-pyran-2-yl)methanol.

26. A pharmaceutical composition which comprises a compound of claim 25 and a pharmaceutically-acceptable diluent or carrier.

27. A compound of ((2S,5S)-5-(8-amino-1-(4-(2,3-difluorophenoxy)phenyl)imidazo[1,5-a]pyrazin-3-yl)tetrahydro-2H-pyran-2-yl)methanol.

28. A pharmaceutical composition which comprises a compound of claim 27 and a pharmaceutically-acceptable diluent or carrier.

29. A compound of (2S,5S)-5-(4-amino-5-(2-fluoro-4-phenoxyphenyl)imidazol[5,1-f][1,2,4]triazin-7-yl)tetrahydro-2H-pyran-2-yl)methanol.

30. A pharmaceutical composition which comprises a compound of claim 29 and a pharmaceutically-acceptable diluent or carrier.

31. A compound of ((2S,5S)-5-(4-amino-5-(2,3-difluoro-4-phenoxyphenyl)imidazo[5,1-f][1,2,4]triazin-7-yl)tetrahydro-2H-pyran-2-yl)methanol.

32. A pharmaceutical composition which comprises a compound of claim 31 and a pharmaceutically-acceptable diluent or carrier.

33. A compound of ((2S,5S)-5-(4-amino-5-(4-(2,3-difluorophenoxy)phenyl)imidazo[5,1-f][1,2,4]triazin-7-yl)tetrahydro-2H-pyran-2-yl)methanol.

34. A pharmaceutical composition which comprises a compound of claim 33 and a pharmaceutically-acceptable diluent or carrier.

* * * * *